(12) United States Patent
Szesko et al.

(10) Patent No.: US 8,215,540 B2
(45) Date of Patent: Jul. 10, 2012

(54) AUTOMATED LABEL VERIFY SYSTEMS AND METHODS FOR DISPENSING PHARMACEUTICALS

(75) Inventors: Michael J. Szesko, Freehold, NJ (US); Bradley Carson, Maumee, OH (US); Derek C. Campbell, Cambridge (CA); Richard A. Lees, Cambridge (CA)

(73) Assignee: Omnicare, Inc., Covington, KY (US)

( * ) Notice: Subject to any disclaimer, the term of this patent is extended or adjusted under 35 U.S.C. 154(b) by 687 days.

(21) Appl. No.: 12/235,173

(22) Filed: Sep. 22, 2008

(65) Prior Publication Data
US 2009/0173779 A1 Jul. 9, 2009

Related U.S. Application Data

(60) Provisional application No. 60/974,181, filed on Sep. 21, 2007, provisional application No. 61/076,905, filed on Jun. 30, 2008.

(51) Int. Cl.
*G06F 17/00* (2006.01)
(52) U.S. Cl. .......................... 235/375; 235/376; 235/475
(58) Field of Classification Search .................. 235/375, 235/376, 475, 483, 481
See application file for complete search history.

(56) References Cited

U.S. PATENT DOCUMENTS

| | | |
|---|---|---|
| 3,606,014 A | 9/1971 | Linn |
| 3,656,616 A | 4/1972 | Wallington |
| 3,882,316 A | 5/1975 | Garris et al. |
| 4,011,155 A | 3/1977 | Feurstein et al. |
| 4,053,056 A | 10/1977 | Day |
| 4,530,199 A | 7/1985 | Manservisi et al. |
| 5,101,609 A | 4/1992 | Cook |
| 5,406,770 A | 4/1995 | Fikacek |
| 5,568,715 A | 10/1996 | Ebel et al. |
| 5,593,267 A | 1/1997 | McDonald et al. |
| 5,660,305 A | 8/1997 | Lasher et al. |
| 5,720,154 A | 2/1998 | Lasher et al. |
| 5,771,657 A | 6/1998 | Lasher et al. |
| 5,880,443 A | 3/1999 | McDonald et al. |
| 5,883,370 A | 3/1999 | Walker et al. |
| 5,963,453 A | 10/1999 | East |
| 6,158,193 A | 12/2000 | Focke et al. |
| 6,317,648 B1 | 11/2001 | Sleep et al. |
| 6,373,520 B1 | 4/2002 | Cadieux, Jr. et al. |
| RE37,829 E | 9/2002 | Charhut et al. |

(Continued)

FOREIGN PATENT DOCUMENTS

CA 2509120 A1 2/2006
(Continued)

OTHER PUBLICATIONS

European Patent Office, International Search Report issued in corresponding PCT Application serial No. PCT/US2008/077184 dated Jan. 9, 2009.

(Continued)

*Primary Examiner* — Edwyn Labaze
(74) *Attorney, Agent, or Firm* — Wood, Herron & Evans, LLP

(57) ABSTRACT

Apparatus and methods for filling a customer order with plurality of products each containing a pharmaceutical. The apparatus and method automatically verify a product barcode on each of the product, print a patient label with a patient barcode for each product, apply the patient labels to at least some of the products, and independently verify that the product barcode matches the proper patient barcode.

54 Claims, 31 Drawing Sheets

U.S. PATENT DOCUMENTS

| | | |
|---|---|---|
| 6,449,927 B2 | 9/2002 | Hebron et al. |
| 6,471,089 B2 | 10/2002 | Liff et al. |
| 6,522,945 B2 | 2/2003 | Sleep et al. |
| 6,575,216 B2 | 6/2003 | Yang |
| 6,655,015 B2 | 12/2003 | Kraenzle |
| 6,776,304 B2 | 8/2004 | Liff et al. |
| 6,814,254 B2 | 11/2004 | Liff et al. |
| 6,814,255 B2 | 11/2004 | Liff et al. |
| 6,892,512 B2 | 5/2005 | Rice et al. |
| 6,970,769 B2 | 11/2005 | Rice et al. |
| 6,971,213 B2 | 12/2005 | Battisti |
| 6,983,579 B2 | 1/2006 | Rice et al. |
| 7,006,893 B2 | 2/2006 | Hart et al. |
| 7,010,899 B2 | 3/2006 | McErlean et al. |
| 7,047,706 B2 | 5/2006 | Kraenzle |
| 7,185,477 B2 | 3/2007 | Rice et al. |
| 7,334,379 B1 | 2/2008 | Siegel et al. |
| 7,386,965 B2 | 6/2008 | McErlean et al. |
| RE40,453 E | 8/2008 | Lasher et al. |
| 7,409,977 B2 | 8/2008 | Rice et al. |
| 7,412,814 B2 | 8/2008 | Rice et al. |
| RE40,510 E | 9/2008 | Lasher et al. |
| 7,427,002 B2 | 9/2008 | Liff et al. |
| 7,430,838 B2 | 10/2008 | Rice et al. |
| 7,467,093 B1 | 12/2008 | Newton et al. |
| 2001/0027634 A1 | 10/2001 | Hebron et al. |
| 2002/0026768 A1 | 3/2002 | Duncan et al. |
| 2002/0100762 A1 | 8/2002 | Liff et al. |
| 2002/0117405 A1 | 8/2002 | Wang et al. |
| 2002/0173875 A1 | 11/2002 | Wallace et al. |
| 2003/0055531 A1 | 3/2003 | Liff et al. |
| 2003/0121929 A1 | 7/2003 | Liff et al. |
| 2003/0125837 A1 | 7/2003 | Walace et al. |
| 2003/0176942 A1 | 9/2003 | Sleep et al. |
| 2003/0189058 A1 | 10/2003 | Liff et al. |
| 2003/0216831 A1 | 11/2003 | Hart et al. |
| 2004/0040975 A1 | 3/2004 | Hunter et al. |
| 2004/0123564 A1 | 7/2004 | McErlean et al. |
| 2004/0210341 A1 | 10/2004 | Wallace et al. |
| 2004/0215486 A1 | 10/2004 | Braverman |
| 2006/0161294 A1 | 7/2006 | DiMaggio |
| 2006/0161298 A1 | 7/2006 | DiMaggio |
| 2006/0185322 A1 | 8/2006 | Kraenzle |
| 2006/0191239 A1 | 8/2006 | Moodley |
| 2006/0277269 A1 | 12/2006 | Dent et al. |
| 2007/0084150 A1 | 4/2007 | Siegel et al. |
| 2007/0093935 A1 | 4/2007 | Fu |
| 2007/0102109 A1 | 5/2007 | Katritzky et al. |
| 2007/0125046 A1 | 6/2007 | Siegel et al. |
| 2007/0125442 A1 | 6/2007 | Tribble et al. |
| 2008/0229718 A1 | 9/2008 | Feehan et al. |
| 2009/0048712 A1 | 2/2009 | Rosenblum |
| 2009/0173779 A1 | 7/2009 | Szesko et al. |
| 2009/0179072 A1 | 7/2009 | Szesko et al. |

FOREIGN PATENT DOCUMENTS

| | | |
|---|---|---|
| EP | 1388336 A1 | 11/2004 |
| EP | 1889802 A2 | 2/2008 |

OTHER PUBLICATIONS

European Patent Office, International Search Report issued in corresponding PCT Application serial No. PCT/US2008/077200 dated Jan. 29, 2009.

USPTO, Office Action issued in related U.S. Appl. No. 12/235,173 dated Jan. 28, 2011.

USPTO, Search Report and Written Opinion issued in related international application No. PCT/US10/60968 dated Apr. 19, 2011.

USPTO, Office Action issued in related U.S. Appl. No. 12/640,065 dated Mar. 12, 2012.

USPTO, Office Action issued in related U.S. Appl. No. 12/640,065 dated Nov. 16, 2011.

USPTO, Office Action issued in related U.S. Appl. No. 12/234,985 dated Mar. 7, 2012.

USPTO, Office Action issued in related U.S. Appl. No. 12/234,985 dated Oct. 3, 2011.

U.S. Patent and Trademark Office, Notice of Allowance issued in corresponding U.S. Appl. No. 12/640,065 mailed May 16, 2012, 8 pages.

AUTOMATED LABEL VERIFY SYSTEMS AND METHODS FOR DISPENSING PHARMACEUTICALS

CROSS-REFERENCE TO RELATED APPLICATIONS

The present application claims the benefit of U.S. Provisional Patent Application Ser. No. 60/974,181, filed Sep. 21, 2007, and U.S. Provisional Patent Application Ser. No. 61/076,905, filed Jun. 30, 2008, the disclosures of which are hereby incorporated by reference herein in their entireties. The present application is also related to co-pending U.S. application Ser. No. 12/234,985, filed Sep. 22, 2008 and entitled "AUTOMATED LABEL VERIFY SYSTEMS AND METHODS FOR DISPENSING PHARMACEUTICALS," the disclosure of which is hereby incorporated by reference herein in its entirety.

BACKGROUND

This disclosure relates to systems and methods for dispensing pharmaceuticals and, in particular, to automated systems and dispensing methods for filling pharmaceutical orders.

Historically, pharmacies have filled large quantities of customer orders for skilled nursing facilities, assisted living facilities, independent living facilities, group homes, hospice facilities and other configurations of the nursing home industry and institutionalized long term care industry with a labor-intensive, pharmacist-based assembly line method. The customer orders are comprised of patient prescriptions, issued by a physician and fulfilled under close pharmacist supervision. The filling of prescriptions consists of executing the customer order by associating the correct pharmaceutical product with the correct prescription label. This is done by pharmacists, technicians, or combinations of these individuals. Products, in the form of a variety of packages (e.g., 7-day, 14-day, 15-day, 30-day dosages, and individually by form and strength), are removed from bulk inventory and, thereafter, a prescription label is printed and manually applied to the appropriate product.

This act of application may then be verified in one of many ways. It can be checked against a master order sheet (MAR), visually checked by the technician, pharmacist, or a combination of these individuals, or can be verified by manually scanning the information on the prescription label with that of the product label. Once each product is labeled, then the labeled products are grouped and presorted into containers. The presorted containers are broken down in a sortation area where the products are individually scanned and placed into the shipping containers (e.g., boxes, bags, bins, or totes). Typically at this point, the label application is re-verified and the product's association with the particular shipping container is checked. This is a barcode-scanning step where the package label, the prescription label, and the shipping tote (or a combination of any number of these items) are confirmed to be correct.

By the time a labeled and verified product is correctly placed in a shipping tote, it has typically been handled, or touched, by an individual approximately 11-13 times. The large number of touches required to process products represents inefficiencies and increases the potential for human error. Therefore, there remains significant room for improvement in the methodologies used by pharmacies to fill prescriptions against customer orders. What is needed are improved systems and methods for automatically labeling, verifying, and handling products that constitute the customer orders.

SUMMARY

An apparatus and method for filling a customer order with plurality of products each containing a pharmaceutical are described below. In one embodiment, the apparatus comprises a machine defining a workflow path for products shaped with at least two different form factors. A plurality of stations are configured to automatically label each of the products shaped with the at least two different form factors and to verify that each of the products belongs in the customer order.

In another embodiment, each of the products is marked with a product barcode. The apparatus of this embodiment comprises a conveyor defining a workflow path for processing the products, a label application station in the workflow path of the conveyor and configured to print and apply a patient label onto each of the products, a vision inspection station configured to independently verify that the product barcode on each of the products matches a patient barcode on the patient label (i.e., that the product barcode is associated with the proper patient barcode) after application to the product, and an unloading station configured to transfer labeled and verified products away from the conveyor. The conveyor may be, for example, a dial conveyor defining a circular workflow path about which the label application station and the vision inspection station are arranged.

In a further embodiment, the apparatus also includes at least one product loading station configured to receive batches of the products and to singulate the products in each of the batches. Multiple product loading stations are provided in embodiments of the apparatus that process products shaped with different form factors. In one specific embodiment, a card loading station is configured to receive and singulate batches of the products shaped with a card form factor, and a box loading station is configured to receive and singulate batches of the products shaped with a box form factor.

An apparatus for filling a customer order with a plurality of the products according to another embodiment generally comprises a product loading station, a first verification station, a label printing station, and a second verification station. The product loading station is configured to receive batches of the products and to singulate the products for subsequent movement along a workflow path. The first verification station is configured to receive the products singulated by the product loading station. A barcode reader in the first verification station is configured to read a product barcode on each of the products, and a transfer arm is configured to remove the products from the workflow path. The label printing station is configured to receive the products not removed from the workflow path by the transfer arm and includes a label printer configured to print patient labels and an applicator configured to apply each patent label on one of the products. The second verification station is configured to receive the products from the label printing station. Additionally, the second verification station includes a barcode reader configured to read the product barcode on each of the products and a patient barcode on each of the patient labels and a transfer arm configured to remove the products from the workflow path.

In one specific embodiment of this apparatus, the product loading station, the first verification station, the labeling station, and the second verification station are configured to process products shaped with at least two different form factors. In another specific embodiment, the apparatus further includes a dial conveyor configured to serially transfer the products to the label printing station and the second verification station along the workflow path.

A method of filling a customer order with a plurality of the products, with the products loaded into a machine for processing, is also provided. The method comprises automatically verifying a product barcode on each of the products, printing a patient label for each of the products processed in the machine, applying the patient labels to at least some of the products, and, thereafter, independently verifying that the product barcode matches a patient barcode on the patent label (i.e., that the product barcode is associated with the proper patient label). In one specific embodiment, the independent verification is accomplished by reading the product barcode and the patient barcode on each product with one or more barcode readers, comparing the product barcode read from each product to tracking data to verify that the product belongs in the customer order being filled, and comparing the patient barcode read from each product to tracking data to verify that the correct patient label has been applied to the correct product. In another specific embodiment, the method further comprises singulating batches of the products loaded into the machine so that the products can be individually processed by the machine.

Another method of filling a customer order with a plurality of the products comprises generating pick requests for the products with a pharmacy host server, transmitting the pick requests to an automated dispensing system, and managing the pick requests with the automated dispensing system to generate pick batches for containers to be filled with products. The pick batches represent products to be loaded into the automated dispensing system. To this end, the method further comprises operating the automated dispensing system to automatically process the products and place the products into the containers.

In a further embodiment of this method, managing the pick requests with the automated dispensing system comprises applying sortation rules to the pick requests to generate the pick batches and controlling the operation of the automated dispensing system based upon the pick batches. The operation of the automated dispensing system is controlled by switching the automated dispensing system between a mode of operation wherein the products are placed into shipping totes for delivery to a customer facility, a mode of operation wherein the products are placed into processing totes that represent partial orders for the customer facility, and a mode of operation wherein the products are placed into containers representing a storage area in a pharmacy.

DETAILED DESCRIPTION

Figure 1:
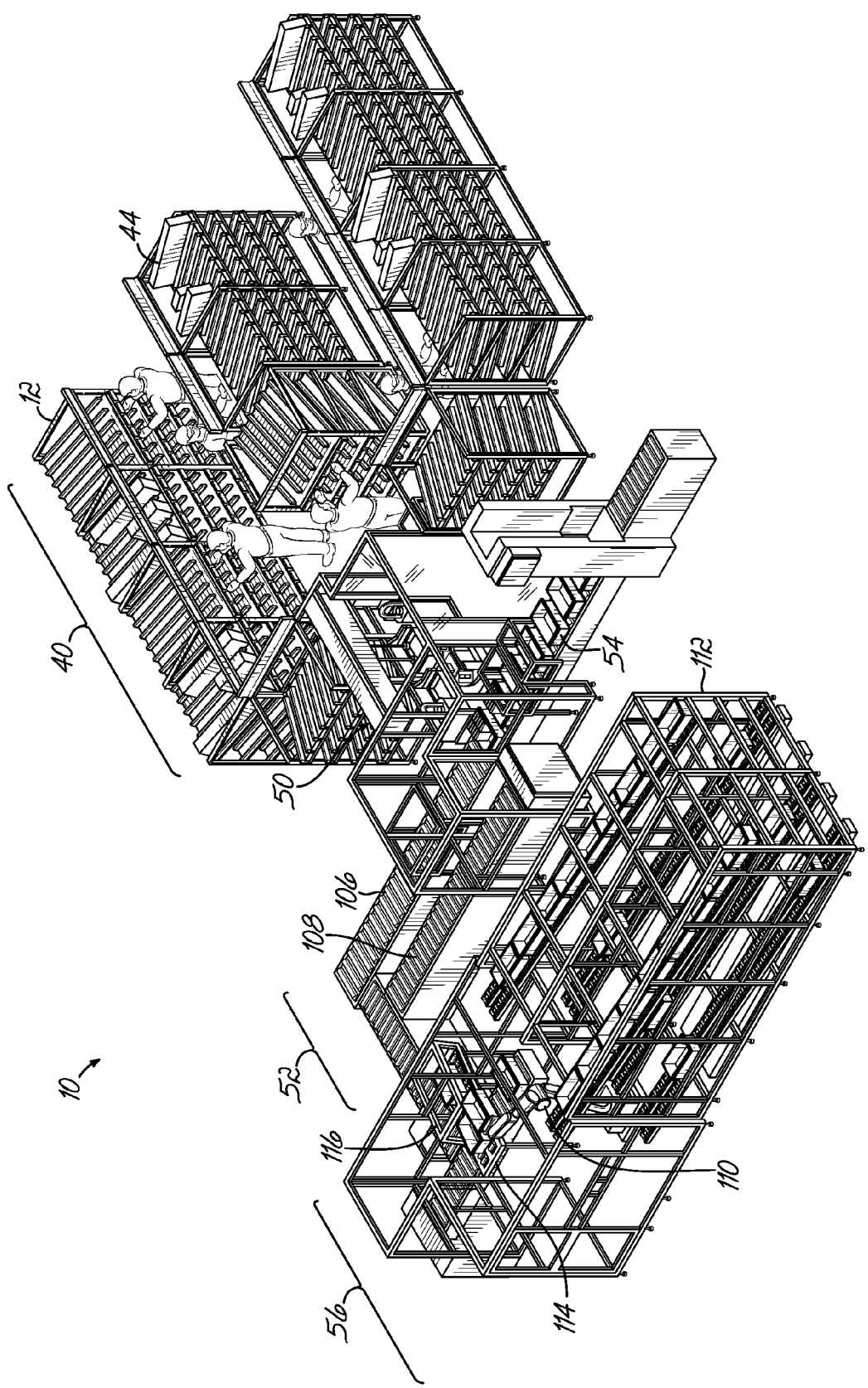
FIG. 1 is a perspective view of an embodiment of an ALV (auto-label-verify) system.
Figure 2:
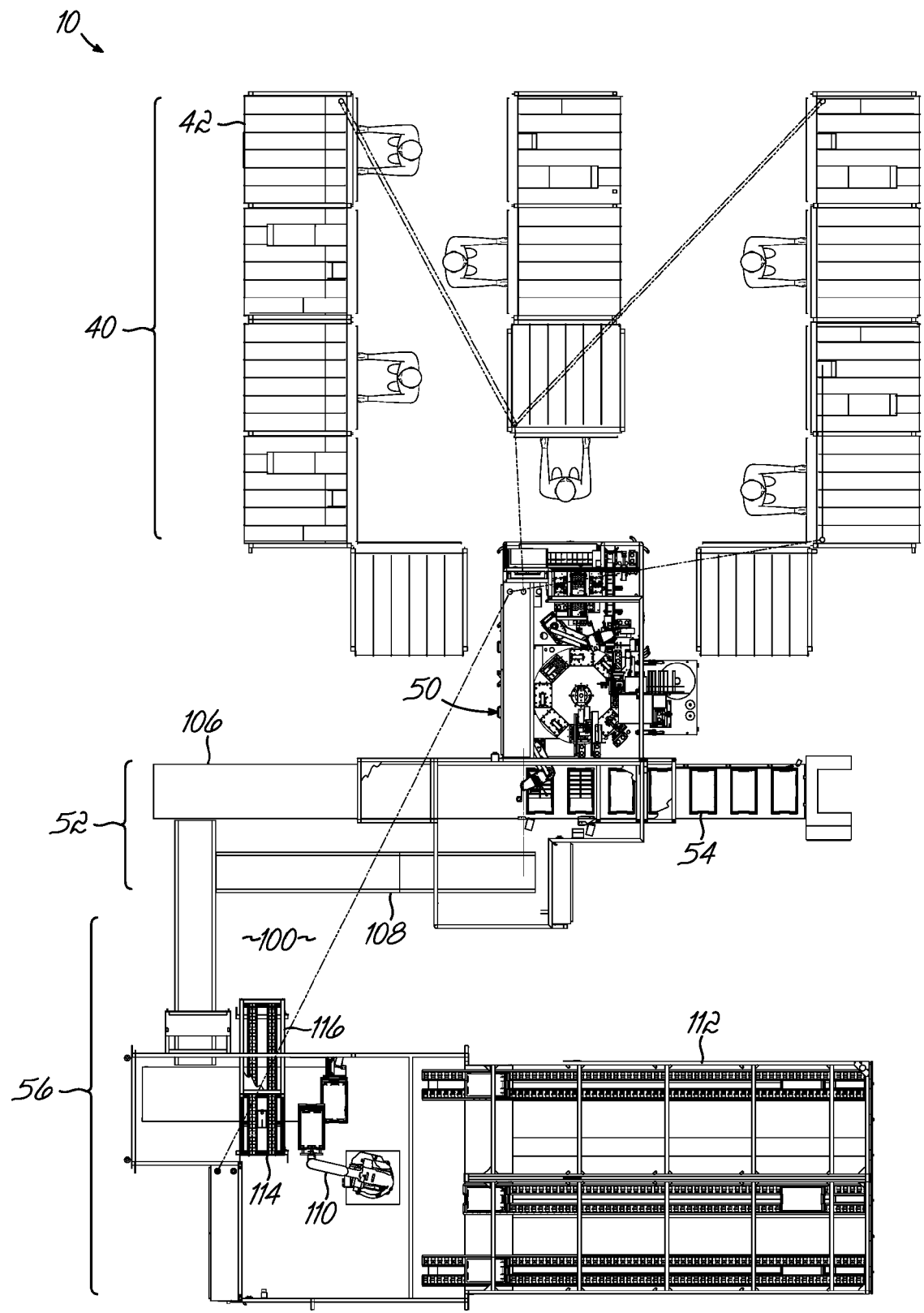
FIG. 2 is a top plan view of the ALV system shown in FIG. 1.

FIGS. 1 and 2 show one embodiment of an Auto Label Verify (ALV) system 10. The ALV system 10 is an automated pharmacy order dispensing system that enables pharmacy orders to be processed in an efficient manner using new methodologies. To facilitate discussion of the ALV system 10 and these methodologies, a general overview of the ALV system 10 is provided below, followed by a discussion of the methodologies for fulfilling pharmacy orders, before describing components of the ALV system 10 in considerable detail.

I. Overview of the ALV System

By way of background, the ALV system 10 may be used to dispense and fulfill prescriptions in products 12 of at least two different form factors. The products 12 are shown in the form of blister cards 20 (FIG. 6) that hold a number of pills (i.e., dosages of pharmaceuticals in oral solid form) and boxes 22 (FIG. 7) that may be prepackaged with individual thermoformed blister strips (not shown) or other packaged of pharmaceuticals. However, those skilled in the art will appreciate that aspects of the invention described below—especially the methodologies discussed in connection with the operation of the ALV system 10—are not necessarily limited to such form factors. Thus, reference number 12 will be used to generically refer to both blister cards 20 and boxes 22, along with other potential form factors, where appropriate to facilitate discussion.

Figure 6:
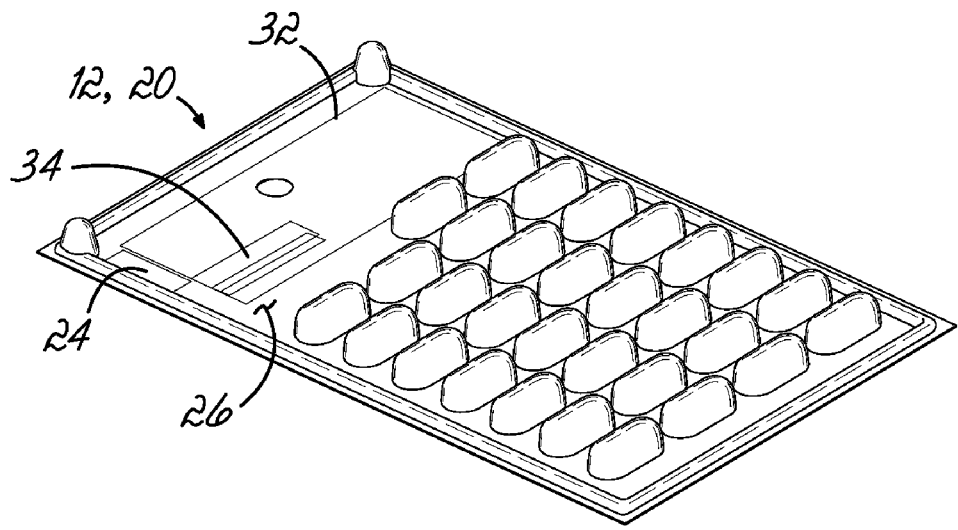
FIG. 6 is a perspective view of a product having a blister card form factor.
Figure 7:
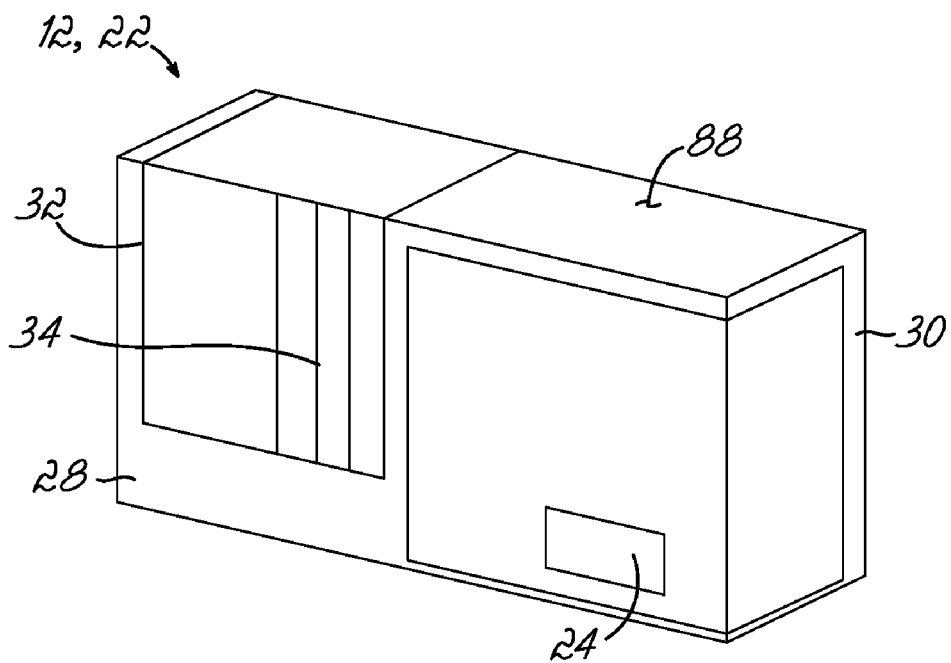
FIG. 7 is a perspective view of a product having a box form factor.

A product barcode 24 on each product 12 reflects the contents of the product 12. Groups of products 12 in a common bulk shipper case supplied to the pharmacy typically share the same mutual product barcode 24. The product barcode 24 may be printed directly on a surface of the product 12 or, alternatively, may be printed on a label that is affixed to a surface of the product 12. The product barcode 24 is positioned on the different products 12 of the same form factor in a consistent manner (i.e., at substantially the same location on the products 12) so that it can be brought into the field of view of readers used by the ALV system 10 to read the product barcode 24. To that end, as shown in FIG. 6, the product barcode 24 on each of the blister cards 20 may be positioned on a front surface 26 near one corner of the blister card 20 and inset slightly from the card perimeter. As shown in FIG. 7, the product barcode 24 on each of the boxes 22 may be positioned on one of two sidewalls 28, 30 of the box 22. Regardless of the form factor, the positioning of the product barcode 24 on the products 12 is chosen such that the product barcode 24 is not obscured or obstructed after a patient label 32 is applied to the product 12 by components within the ALV system 10.

The patient label 32 (outlined schematically in FIGS. 6 and 7) is printed on conventional label stock and includes an adhesive backing for adhesively bonding to the product 12. A patient barcode 34, which encodes information relating the prescription, is situated within a given spatial window or footprint inside the perimeter of the patient label 32. The ALV system 10 is tolerant of slight inaccuracies in the precise location of the patient barcode 34 on the patient label 32 and of the patient label 32 on the product 12 for purposes of reading the patient barcode 34. The positioning of the patient barcode 34 on the labeled products 12 is reproducible to an extent necessary for the field of view of readers used by the ALV system 10 to read the patient barcode 34. The patient label 32 may further include human-readable information relating to the drug or pharmaceutical contained in the product 12 and/or the customer for the pharmaceutical contained in the product 12.

With this general understanding of the products 12 processed by the ALV system 10, an overview of the ALV system 10 will now be explained with reference to FIGS. 1-5. The ALV system 10 includes a pick-to-light system 40 having pick-to-light racks 42 that hold bulk shipper cases 44 containing the products 12, an ALV machine 50 that processes the products 12, a tote conveyor system 52 that supplies containers 54 for receiving the products 12 processed by the ALV machine 50, and a tote handling system 56 that handles filled containers 54 from the tote conveyor system 52. One aspect of the ALV machine 50 is its ability to interchangeably handle products 12 of different form factors without any reconfiguration or alteration to the ALV machine 50.

An ALV Order Manager (AOM) control system interfaces with a pharmacy host server to manage information sent to and from the ALV machine 50 and pick-to-light system 40. The ALV machine 50 processes products 12 pulled by an operator from the racks 42 of the pick-to-light system 40 by passing them through various stations designed to serve one or more specific functions. To this end, the ALV machine 50 includes both a card loading station 60 and a box loading station 62 for receiving the products 12 pulled by an operator from the racks 42 of the pick-to-light system 40. The card loading station 60 and box loading station 62 are each configured to read the product barcode 24 (FIGS. 6 and 7) on the associated type of products 12 (i.e., blister cards 20 and boxes 22) to verify and track the products 12. This verification task is achieved while delivering the products 12 in an organized manner to a transfer station 64, which includes a transfer arm in the form of a robot 66 for transferring the products 12 to designated locations on a rotary or dial conveyor 68. The robot 66 also transfers the products 12 to a first reject bin 70 (instead of the dial conveyor 68) under certain conditions, such as when a product 12 cannot be verified. Thus, aspects of the card loading station 60 and box loading station 62, together with the transfer station 64, serve as a first product verification and rejection (PVR1) station.

The dial conveyor 68 rotates to deliver or bring the products 12 to a labeling station 76. At this station, the ALV machine 50 prints the patient labels 32 (FIGS. 6 and 7) having patient-specific information in the form of the patient barcode 34, verifies that the patient barcode 34 is printed on each patient label 32, and applies each successfully-verified patient label 32 to the corresponding product 12. More specifically, a label printer 78 associated with the ALV machine 50 prints the patient labels 32 to apply the patient-specific information. A label applicator 80 verifies the patient barcode 34 and applies the associated patient label 32 to the corresponding product 12. Patient labels 32 that fail verification are applied to label reject device 82 rather than to one of the products 12. Thus, the labeling station 76 serves as a label print, verify, and apply (LPVA) station.

When products 12 in the form of boxes 22 are being processed, the labeling station 76 applies the associated patient label 32 to a front surface 88 (FIG. 7, viewed from above and looking downwardly) of each box 22. The patient label 32 has a width greater than that of the front surface 88 such that projecting portions of the patient label 32 extend outwardly above the sidewalls 28, 30 when the patient label 32 is applied to the front surface 88. To complete the label application process, the dial conveyor 68 further rotates to bring the box 22 to a label wipe station 90 that pushes these projecting portions flat onto the opposed sidewalls 28, 30 of the box 22. The blister cards 20 are not processed by the label wipe station 90 because the patient labels 32 are initially applied entirely flat onto the front surface 26 (FIG. 6) of this form factor.

The next station associated with the circular workflow path of the dial conveyor 68 is a vision inspection station 92 that performs another verification step. At this station 92, the ALV machine 50 re-verifies both the product barcode 24 on the product 12 and the patient barcode 34 on the patient label 32. If either of the barcodes 24, 34 cannot be read or do not match/correlate with product tracking data, the product 12 is flagged as a reject. If the barcodes 24, 34 do match/correlate with product tracking data, the product 12 is flagged as an accepted item.

Finally, the dial conveyor 68 brings the product 12 to an unloading station 94. A robot 96 at the unloading station 94 transfers the products 12 flagged as rejects into a second reject bin 98 and transfers the products 12 flagged as accepted items into one of the containers 54 on the tote conveyor system 52. Thus, the vision inspection station 92 and unloading station 94 serve as a second product verification and rejection (PVR2) station.

The tote conveyor system 52, which is tightly integrated with the operation of the ALV machine 50, sends the containers 54 filled with verified and labeled products 12 along a main conveyor 106 to the tote handling system 56. The tote conveyor system 52 also includes a parallel conveyor 108 so that the filled containers 54 can alternatively be sent to an audit station 100 whenever an audit is desired for quality assurance. At the audit station 100, an operator uses a handheld barcode scanner and operator's interface (neither of which are shown) to verify the contents of the container 54 before passing the container 54 to the tote handling system 56. A tote load robot 110 in the tote handling system 56 places the containers 54 onto a tote rack 112 or, when an audit is to be performed, onto a tote return conveyor 114 leading to an escapement 116 where an operator at the audit station 100 can pick up the container 54. Thus, a filled container 54 may be transferred to the audit station 100 by either the tote conveyor system 52 or the tote handling system 56.

Although only one ALV system 10 is shown, a pharmacy can house multiple ALV systems (not shown) each identical or substantially similar to ALV system 10. The ALV system 10 may constitute stand-alone stations in a non-integrated pharmacy, each having their own tote conveyors systems 52 and tote handling systems 56, or components of an integrated (i.e., automated) pharmacy in which the individual ALV systems 10 are linked together by a shared tote conveyor system and/or tote handling system. In the latter instance, multiple ALV systems 10 inside the same pharmacy may be logically connected to one of the ALV systems 10 (designated as the primary ALV system 10) via a communications channel, such as an Ethernet communications channel, and physically connected to the tote conveyor system and/or tote handling system shared by the multiple ALV systems 10. The AOM control system of the primary ALV system 10 may be used to control one or more of the additional ALV systems 10 housed in the pharmacy.

II. Using the ALV System to Fulfill Pharmacy Orders

The ALV system 10 represents an automated order dispensing system situated within the pharmacy that is used to fulfill prescriptions specified by customer orders. A customer order represents prescriptions delivered to a customer location (e.g., nursing facility) in a particular shipment from the pharmacy. As such, the customer order may thus comprise a collection of individual patient orders for the patients at the customer location. Each patient order may include one or more prescriptions, and each individual prescription may include one or more products 12 of the blister card 20 or box 22 form factor. The products 12 of each prescription have a unique drug stock keeping unit (SKU) representing medication type, strength, form factor for the product packaging, etc. Drug SKUs are assigned and serialized for inventory management at the source of the products 12. The products 12 may also include printed or labeled human-readable information, such as the manufacturer or supplier name, medication type, medication strength and description, lot number, expiration date, etc.

A pharmacy host server (i.e., computer system) communicates with, and gives tasks to, the ALV system 10. The pharmacy host may be, for example, a warehouse management system or a warehouse control system. This pharmacy host tracks inventory in the pharmacy and tracks and directs orders through the pharmacy. Orders from the pharmacy host are sent to the ALV system 10 in the form of "pick requests" for the products 12.

The AOM control system applies various sort rules/logic to manage the pick requests received from the pharmacy host server. For example, the AOM control system may group incoming picks by customer facility, order the picks by priority, group by drug, group by patient, etc. The number of orders processed by the pharmacy host server, and, thus, the number of pick requests sent to the AOM control system, typically varies depending on the time of day. There may be high volumes of orders received at certain peak times (e.g., at the beginning and end of normal working hours) and low volumes at other times (e.g., the late evening hours). Advantageously, the AOM control system manages pick requests received from the pharmacy host server so that customer orders are processed in an opportunistic manner.

More specifically, the ALV system 10 operates in three different modes of operation to optimize efficiency. During high-volume times of the day, the ALV system 10 operates in an on-demand mode. The containers 54 processed by the ALV system 10 in this mode of operation are shipping totes that will be delivered to a customer facility. The large number of pick requests at these times enables the AOM control system to sort the pick requests into large pick batches for each facility. The products 12 corresponding to the pick batches fill, or substantially fill, the shipping totes. As briefly described above, the ALV system 10 automatically prints and applies patient labels 32, verifies the product and patient barcodes 24, 34, and deposits the labeled and verified products 12 into the containers 54. The containers 54 are verified as well (by barcode readers associated with the tote conveyor system 52, as will be discussed below). Because the containers 54 are shipping totes that will be delivered to the customer facility, no further processing or verification steps are required during this mode of operation.

During other times of the day when there are moderate volumes of customer orders, the on-demand mode begins to lose some of its efficiency. The pick batches produced by the on-demand sort rules of the AOM control system are smaller and do not fill the shipping totes. As a result, the ALV system 10 switches to a mode of operation in which the containers 54 are work-in-process (WIP) totes that are less cumbersome to work with and that remain inside the pharmacy. This WIP tote mode of operation involves automatically filling the WIP totes with the labeled and verified products 12 corresponding to the smaller pick batches. Thus, the WIP totes are loaded with the products 12 in a manner similar to the shipping totes.

The WIP totes may even be transferred to the tote racks 112 of the tote handling system 56 after receiving the products 12. The difference, however, is that an additional processing step takes place during this mode of operation.

Specifically, the products 12 in two or more WIP totes associated with a customer order must later be combined/ transferred into a common shipping tote. Each WIP tote includes a barcode so that the products 12 placed therein can be verified for proper association with the WIP tote (similar to the verification of the shipping totes). Because of this WIP tote verification, the products 12 can be transferred to the shipping totes and verified for proper association with the shipping totes without having to individually scan each product 12. Instead, an operator simply scans the WIP tote and the shipping tote before transferring all of the products 12 from the WIP tote into the shipping tote. This scanning step is performed for each WIP tote whose contents are transferred to a particular shipping tote.

During times of the day when there are the lowest volumes of customer orders, the pick batches generated by the AOM control system using the on-demand sort rules become even smaller. This results in operators walking more between the pick-to-light racks 42 and the ALV machine 50. Additionally, the number of WIP totes whose products 12 must be combined to fill a single shipping tote increases, resulting in more scanning steps. Because of these inefficiencies, the ALV system 10 switches to an "aisle tote" mode of operation. In this mode of operation, the AOM control system groups incoming picks by SKU and sorts them by aisle or section of the pharmacy where they are to be temporarily stored. This allows for larger pick batches to be generated. The aisle totes are filled with labeled and verified products 12 and then taken to their temporary storage locations. Operators then fill shipping totes in a conventional manner by selecting individual products 12 from the various storage locations and scanning each product 12 for verification as it placed in the shipping tote.

As can be appreciated, the ALV system 10 significantly automates the process of fulfilling pharmacy orders. The automation enables a large number of pick requests to be processed quickly and reliably with little human intervention, representing significant cost savings. Indeed, in on-demand mode, the products 12 are labeled, verified, and ready to ship to a customer facility after being "touched," or handled, only once by an operator (the touch occurs during transfer from the pick-to-light system 40 to the ALV machine 50). In WIP tote mode, the products 12 are "touched" twice because of the additional handling step when transferring the products 12 from the WIP totes to the shipping totes. However, WIP tote mode still avoids the need to individually scan each labeled and verified product 12 during transfer to the shipping totes. Although operators must still manually perform such steps in aisle tote mode, the ALV system 10 still provides several advantages. In all modes of operation, the steps of manually applying the patient label 32 to the product and verifying the patient barcode 34 and product barcode 24 immediately after label application is automated by the ALV system 10. Thus, the ALV system 10 still provides significant cost-saving opportunities even when operating in aisle tote mode.

Having described the methodologies used by the ALV system 10 to fulfill pharmacy orders, the various components of the ALV system 10 will now be described in the further detail.

III. Components of the ALV System (a) Controls

Figure 5:
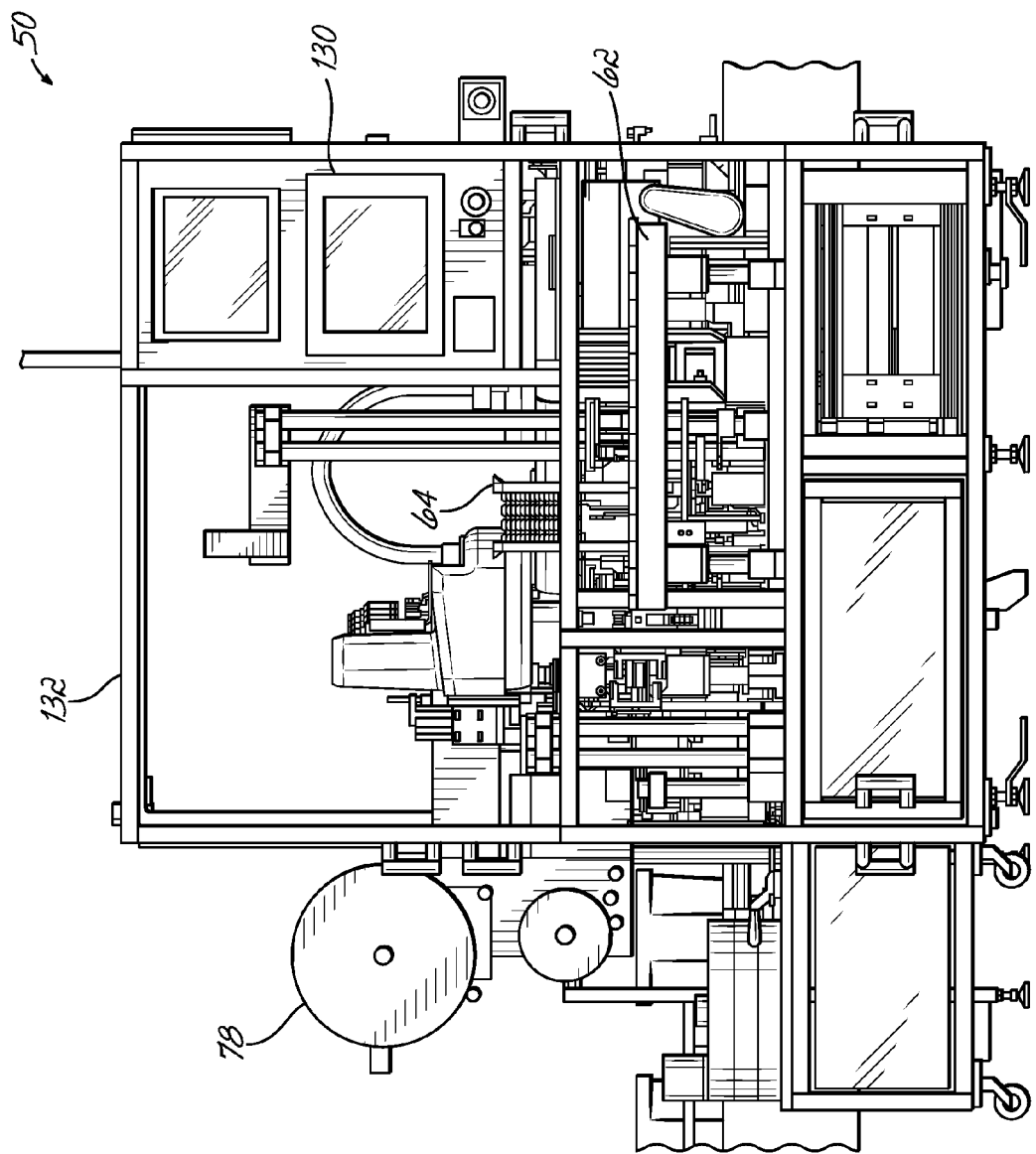
FIG. 5 is a front elevation view of the ALV machine of FIG. 3.

The ALV machine 50 of the ALV system 10 is controlled by a controller (not shown), such as a programmable logic controller (PLC) or, in a specific embodiment, an Allen-Bradley CompactLogix PLC. The controller may include one or more central processing units (CPUs) for processing programmable components contained in a memory card or extendable memory, a power supply unit, an input/output control module, and other components recognized by a person having ordinary skill in the art. The controller is programmed with a series of program components having a series of algorithms for controlling the mechanical functions of the ALV machine 50, as well as operating as an input/output interface to the various barcode readers, motors, and movable components contained in the ALV machine 50 and an input/output interface to a human machine interface (HMI) computer 130 (FIG. 5). These program components may be stored in memory and executed by one of the CPUs within the controller.

The controller is used to coordinate and orchestrate the mechanical functions of the ALV machine 50. The communications interface(s) may comprise any common communications channel technology recognized by a person having ordinary skill in the art, including but not limited to Ethernet, Fieldbus (CAN/CAN OPEN), or Serial (RS-232) protocols. The controller tracks product data associated with each of the products 12 processed by the various stations of the ALV machine 50. Product information and status from the tracking data can be displayed and updated on demand at the HMI computer 130.

With reference to FIG. 5, the HMI computer 130 is supported by framework 132 of the ALV machine 50 at an elevated location near the card loading station 60 and box loading station 62. The HMI computer 130 may run any conventional operating system and may execute different software applications that cooperate with the operation of the controller for controlling the processing of products 12 in the ALV machine 50. The HMI computer 130, which permits the operator to interact with the ALV machine 50, may comprise a touch sensitive display or computer screen that promotes operator interactions. The HMI computer 130 may implement a Graphical User Interface (GUI) on the computer screen that features frames and panes with buttons and specific interface components for operator interaction in connection with test, set up, and run procedures of the ALV system 10.

The HMI computer 130 communicates over a communications channel, such as Ethernet, with the pharmacy host. As mentioned above, the pharmacy host is a computer system that communicates with, and gives tasks to, the ALV system 10.

The AOM control system of the ALV system 10 includes multiple processors that implement software applications and collectively process orders and pick requests received from the pharmacy host. The computers, which are coupled together by a communications channel such as Ethernet, include a pick server, a real time pick-to-light computer (PickPC), a statistics computer (StatPC), and an order reconciliation computer. The PickServer, PickPC, and StatPC may be rack-mounted servers physically mounted in the ALV machine 50 or housed in the pharmacy, as appropriate. The PickServer, PickPC, and StatPC may be constructed with fault tolerant redundant power supplies and hot swappable Redundant Array of Independent Disks (RAID) drives. The order reconciliation computer may comprise a desktop personal computer and an interfaced hand-held barcode scanner that can be mounted anywhere in the pharmacy.

(b) Pick-to-Light System

Orders in the form of pick requests are communicated from the pharmacy host to the ALV system 10. As discussed above, the pick requests are stored by the AOM control system for logical grouping based on user-defined parameters and retrieval. The logical grouping process results in pick batches for the operator to pick from the pick-to-light racks 12. Each pick batch can contain one or more products 12 destined for a placement into one of the containers 54.

Figure 8:
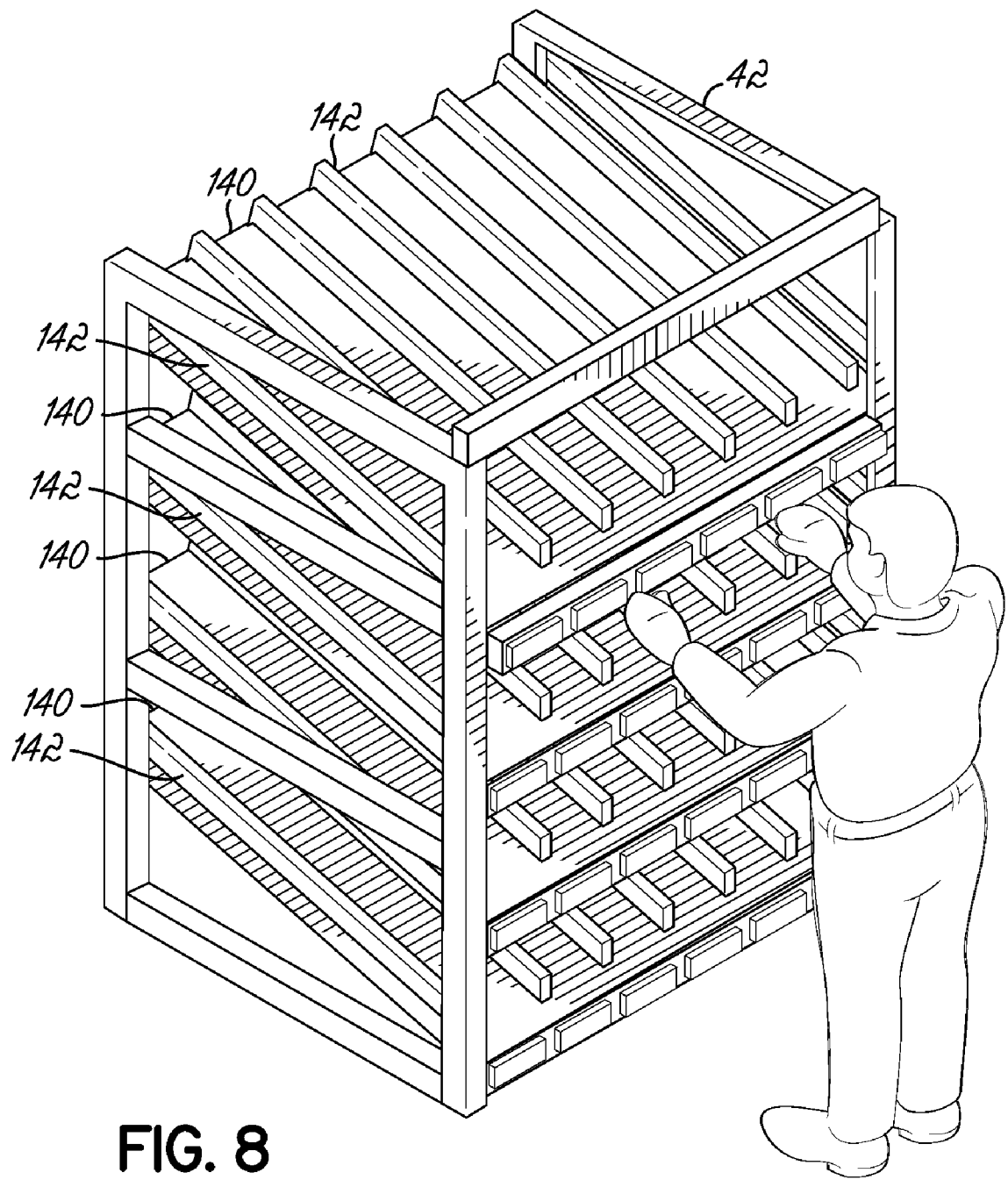
FIG. 8 is a perspective view of a pick-to-light rack used in the ALV system of FIG. 1.

A representative pick-to-light rack of the pick-to-light system 40 is shown in FIG. 8. Each of the pick-to-light racks 12 includes a bay controller (not shown) and multiple shelves 140 arranged in levels. Each of the shelves 140 is partitioned by dividers 142 to define multiple bins or inventory locations that are within arms-reach of a technician and stocked with one or more bulk shipper cases 44 (FIG. 1). Each bulk shipper case 44 holds products 12 characterized by a unique drug SKU. More than one inventory location, typically adjacent inventory locations, in the pick-to-light racks 12 can hold bulk shipper cases 44 holding products 12 with the same drug SKU, which are managed as a single unit by the ALV system 10. Most drug SKUs have a single inventory location on the shelves 140 of the pick-to-light racks 12, although products 12 with faster moving drug SKUs can be assigned to multiple inventory locations.

As shown in FIGS. 1 and 2, the pick-to-light racks 12 can be arranged to surround one or more operators. Some or all of the individual racks 42 of the pick-to-light system 40 may be supported on castors (not shown) that ease re-configuration of the arrangement relative to the ALV machine 50. The peripheral pick-to-light racks 42 may be arranged in, for example, a U-shape to minimize the walking distance along the aisles from the inventory locations of the pick-to-light system 40 to the ALV machine 50. However, the pick-to-light racks 12 may have another configuration chosen to accommodate spatial constraints in the pharmacy or a design choice. The vertical position and inclination angle of the shelves 140 in the pick-to-light racks 12 may be adjustable. The pick-to-light racks 12 may be arranged to locate specific inventory locations for products 12 of faster moving drug SKUs closer to the card loading station 60 and box loading station 62 of the ALV machine 50.

In a manner not shown herein, each inventory location in the pick-to-light racks 12 has a dedicated pick-to-light module with a pick face that includes an indication light, one or more buttons, and an alphanumeric display module. The alphanumeric display indicates to the operator the number of products 12 to be picked for an order, and the buttons permit the operator to adjust the quantity up, or down, if there are inventory issues. The adjustments provide a means for the operator to update the database of the AOM control system with real-time, accurate inventory counts of products 12. Each of the pick-to-light racks 12 may include other types of pick-to-light modules, such as an order control module, that are operated under the control of the bay controller.

In the workflow sequence for the ALV system 10, an operator is instructed to pick individual products 12 from the pick-to-light system 40 with visual queues supplied by the indication lights associated with the inventory locations. The indication lights on the pick-to-light modules assist the operator to quickly and accurately identify the inventory locations in the pick-to-light racks 12 for each pick batch. The operator picks products 12 from the lighted inventory locations, adjusts for any inventory (if needed) using the buttons on the pick face, and presses a pick complete button on the pick face of the inventory locations. The operator repeats this process until all lighted inventory locations in the pick-to-light racks 12 are acknowledged, which indicates to the controller that the operator has completed the pick batch.

If the products 12 collected by the operator are in the form of blister cards 20, the operator delivers the blister cards 20 to the card loading station 60 of the ALV machine 50. If the products 12 are boxes 22, the operator delivers the boxes 22 to the box loading station 62 of the ALV machine 50.

(c) Card Loading Station

Figure 9:
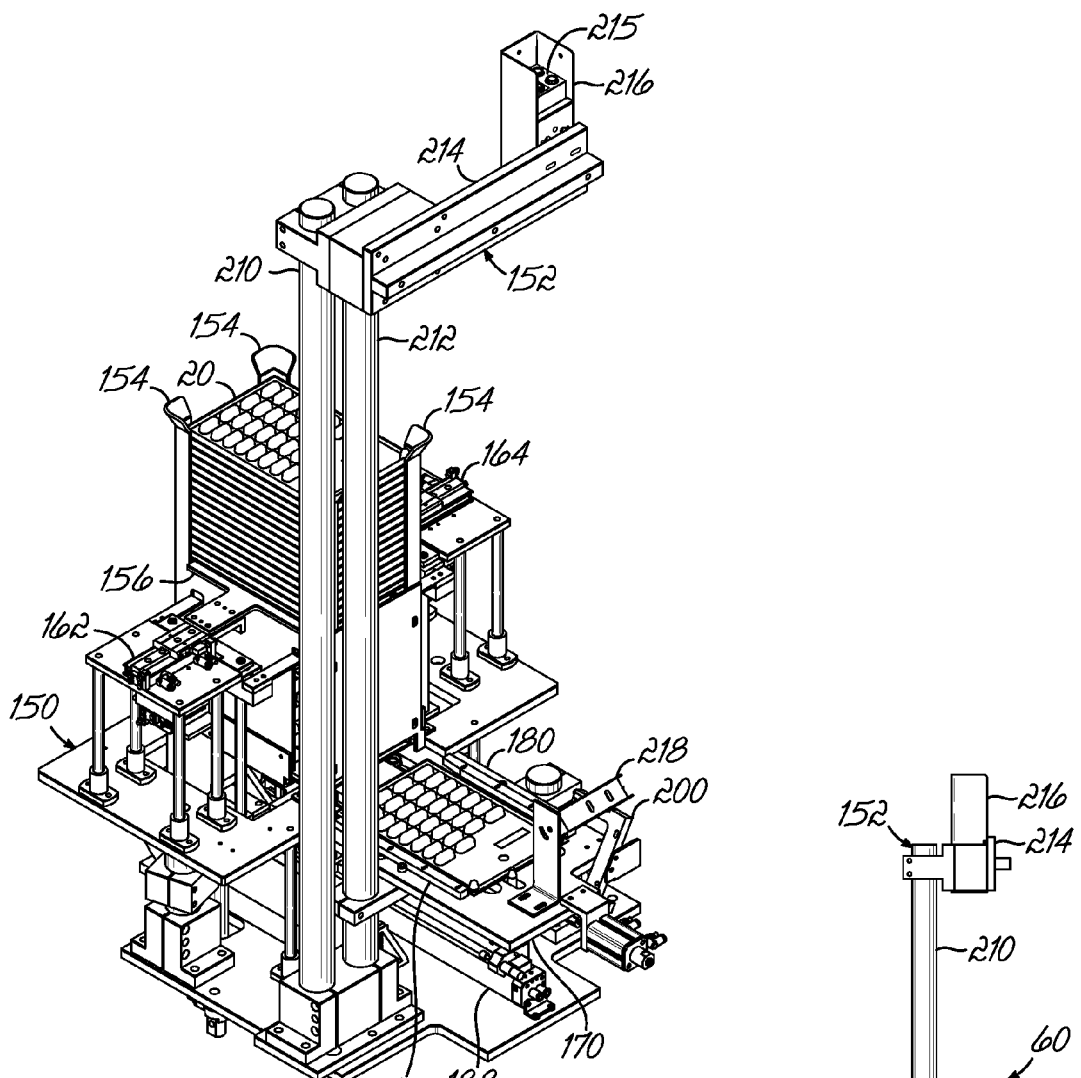
FIGS. 9, 10, and 11 are respective perspective, side elevation, and top plan views of a product induction magazine for singulating a stack of the blister cards and a camera assembly for reading product barcodes on the blister cards.
Figure 11:
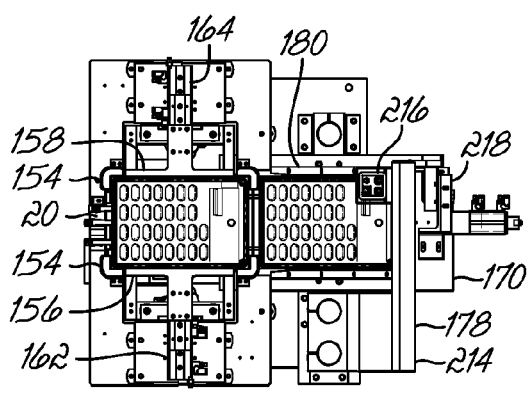
Figure 10:
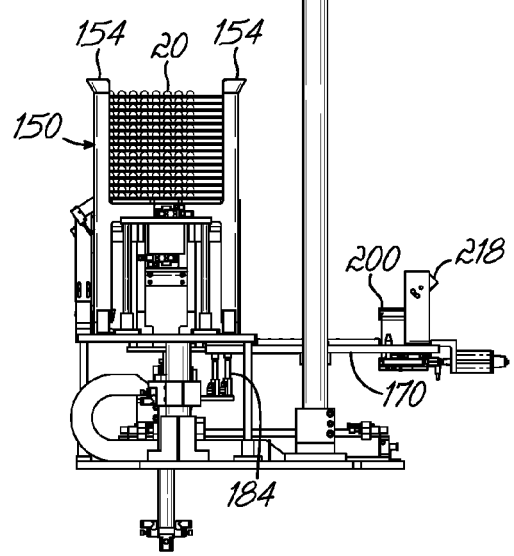
Figure 12:
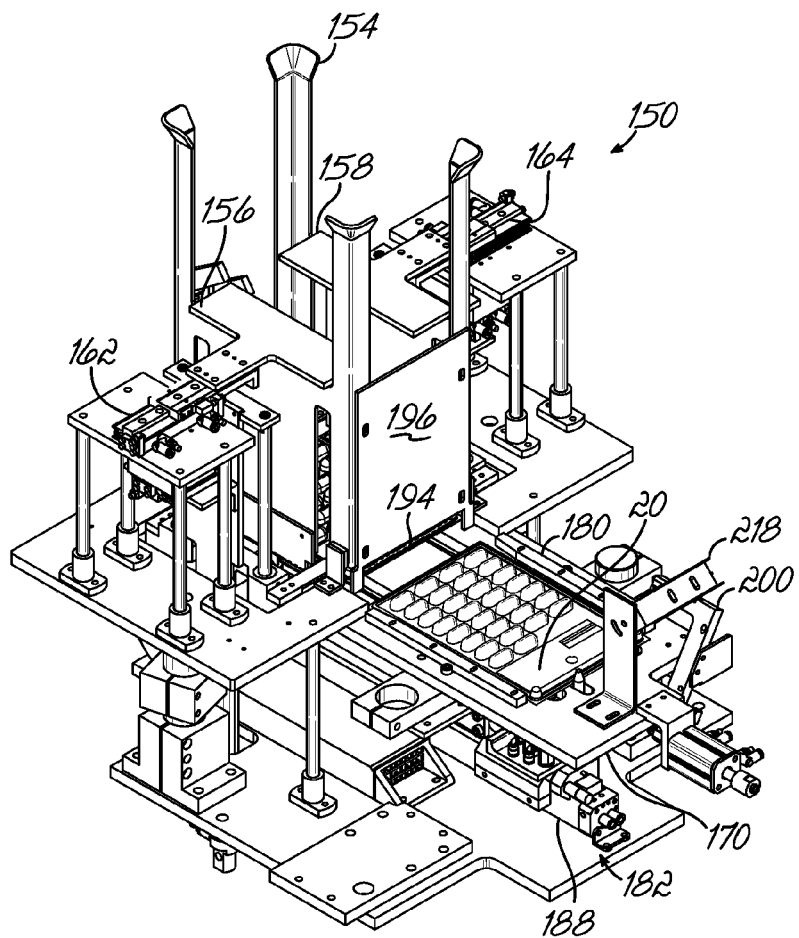
FIGS. 12 and 14 are perspective and side elevation views, respectively, of the product induction magazine.
Figure 13:
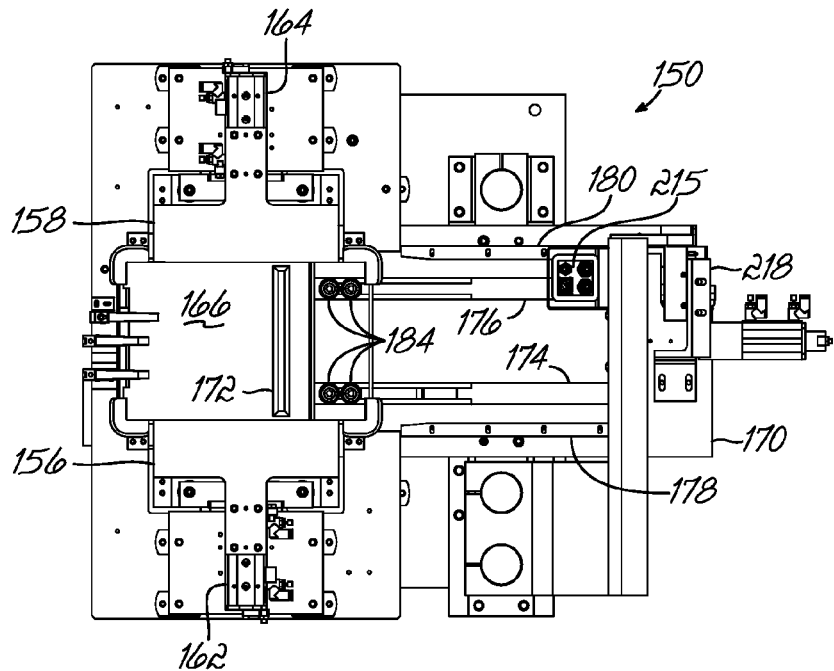
FIG. 13 is a top plan view of the product induction magazine of FIGS. 12 and 14 with the blister cards omitted for clarity.
Figure 14:
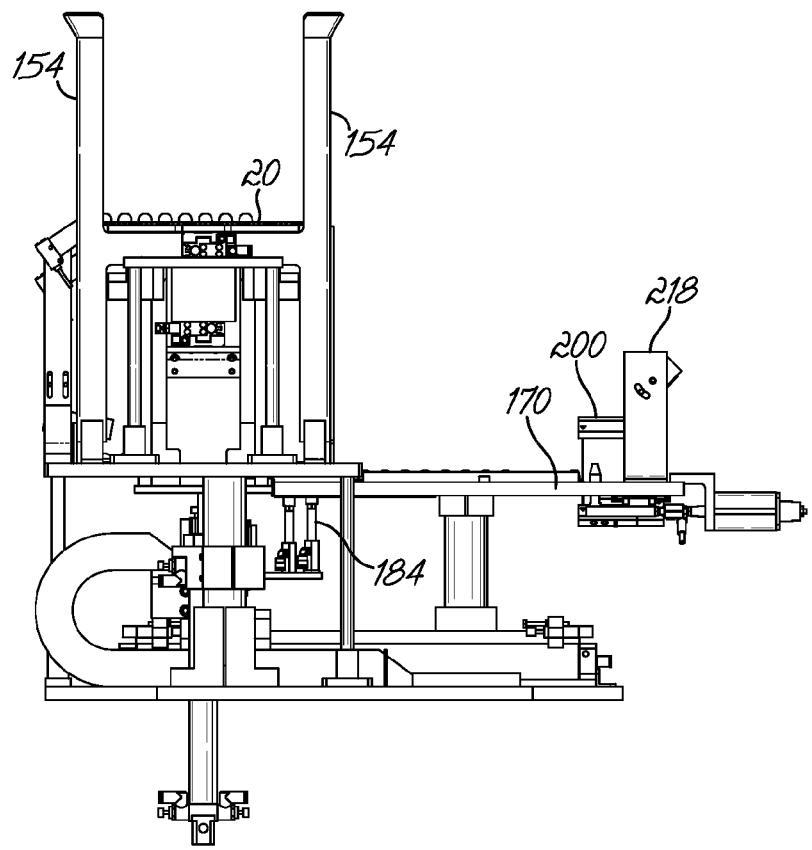
Figure 15:
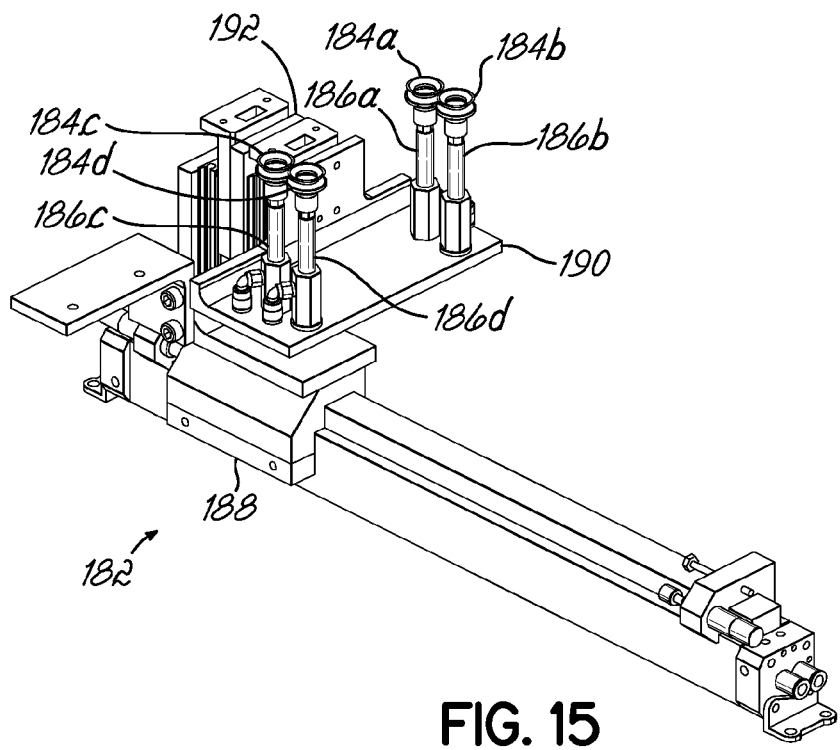
FIG. 15 is a perspective view of a gripping device of the product induction magazine of FIGS. 9-14.
Figure 16:
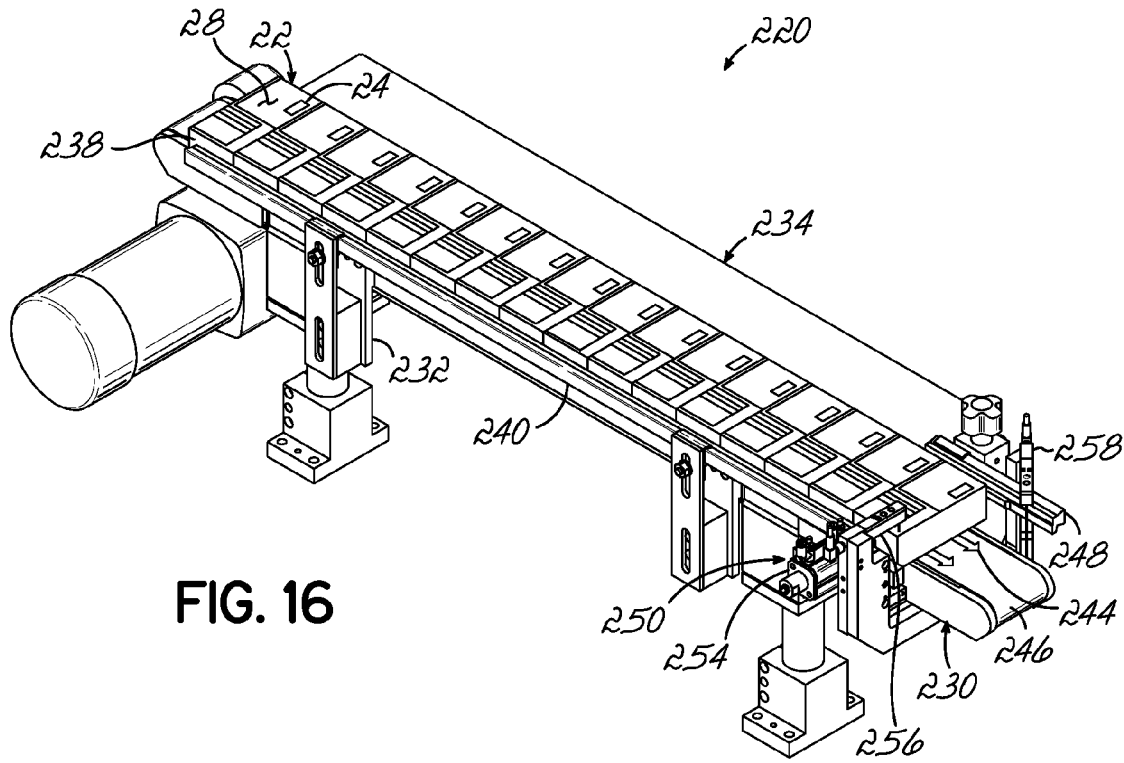
FIGS. 16 and 17 are perspective and top plan views, respectively, of a box loading conveyor of the ALV machine.
Figure 17:
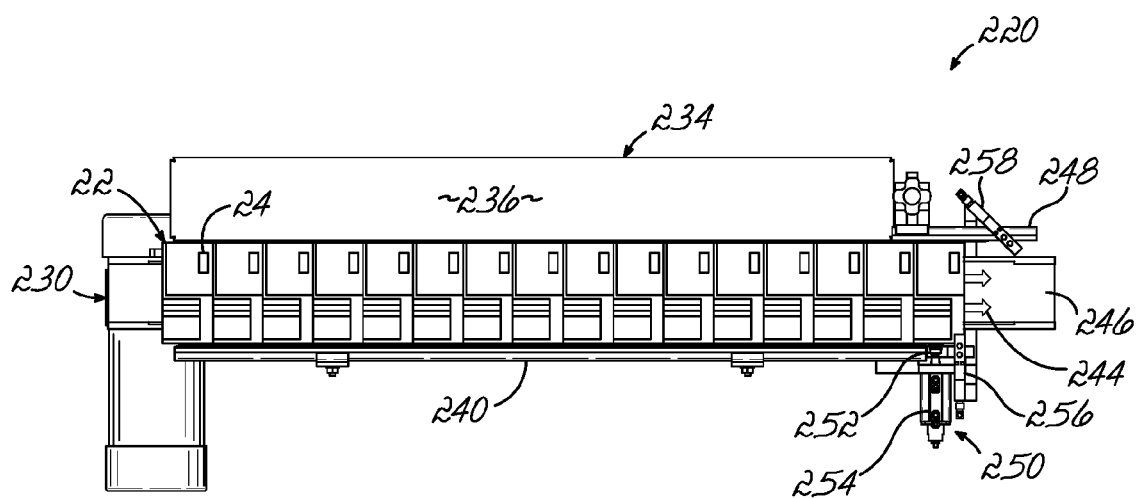
Figure 18:
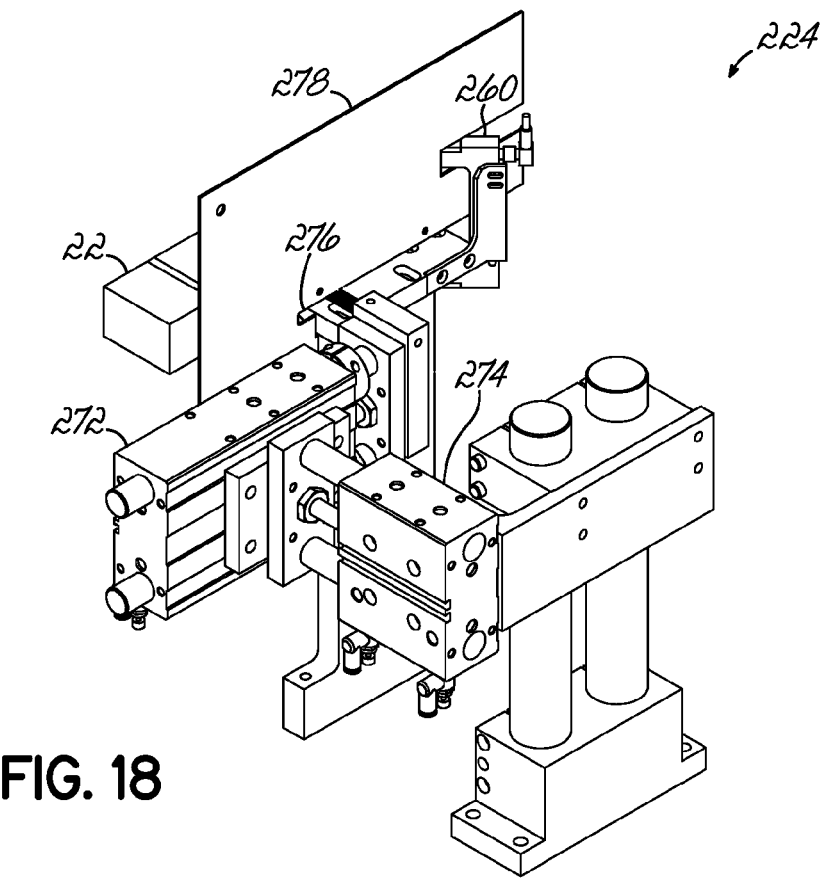
FIGS. 18 and 19 are perspective and top plan views, respectively, of a box transfer assembly of the ALV machine.
Figure 19:
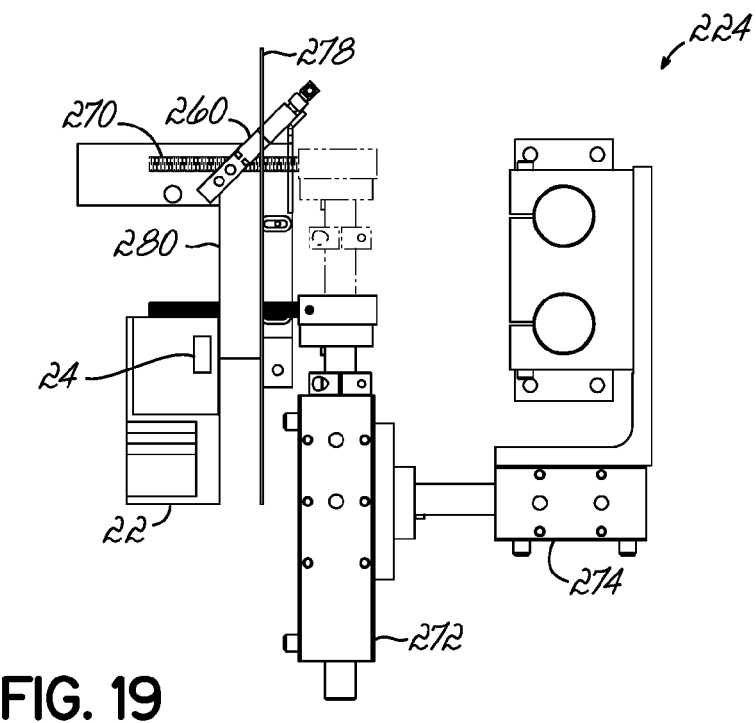
Figure 20:
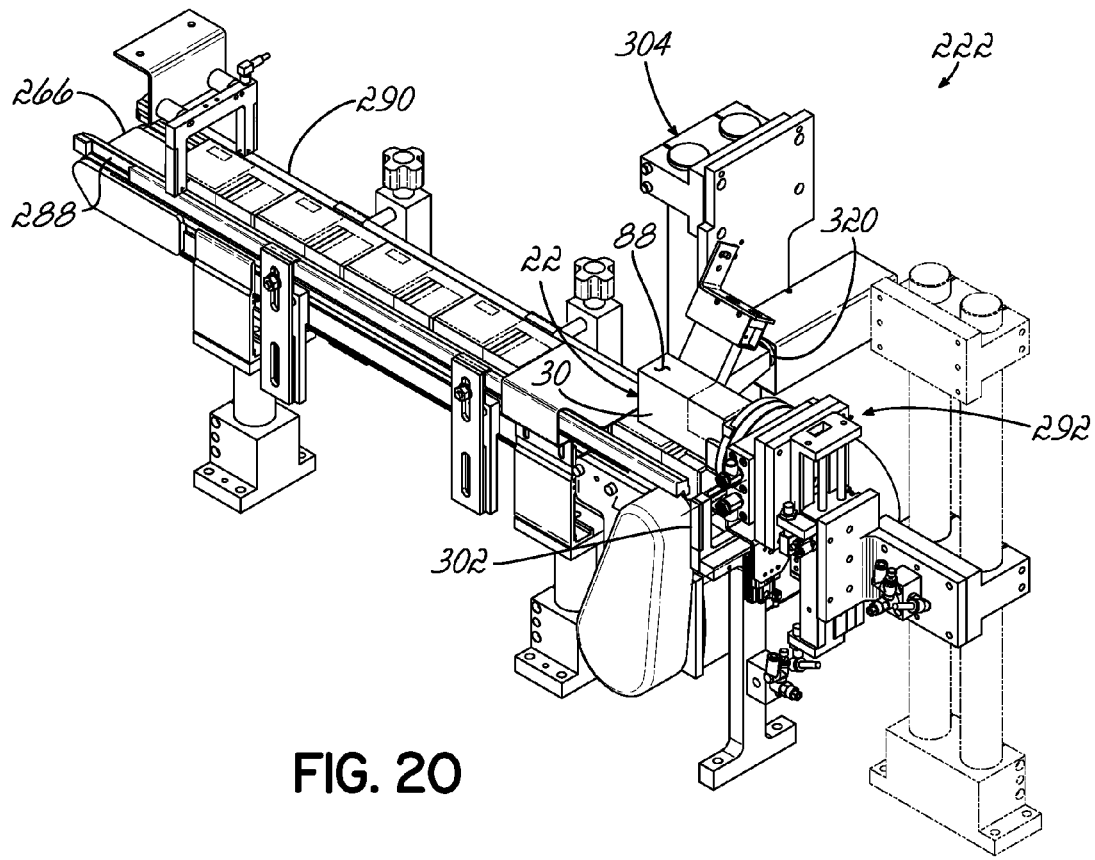
FIGS. 20 and 21 are perspective and top plan views, respectively, of a box infeed conveyor of the ALV machine.
Figure 21:
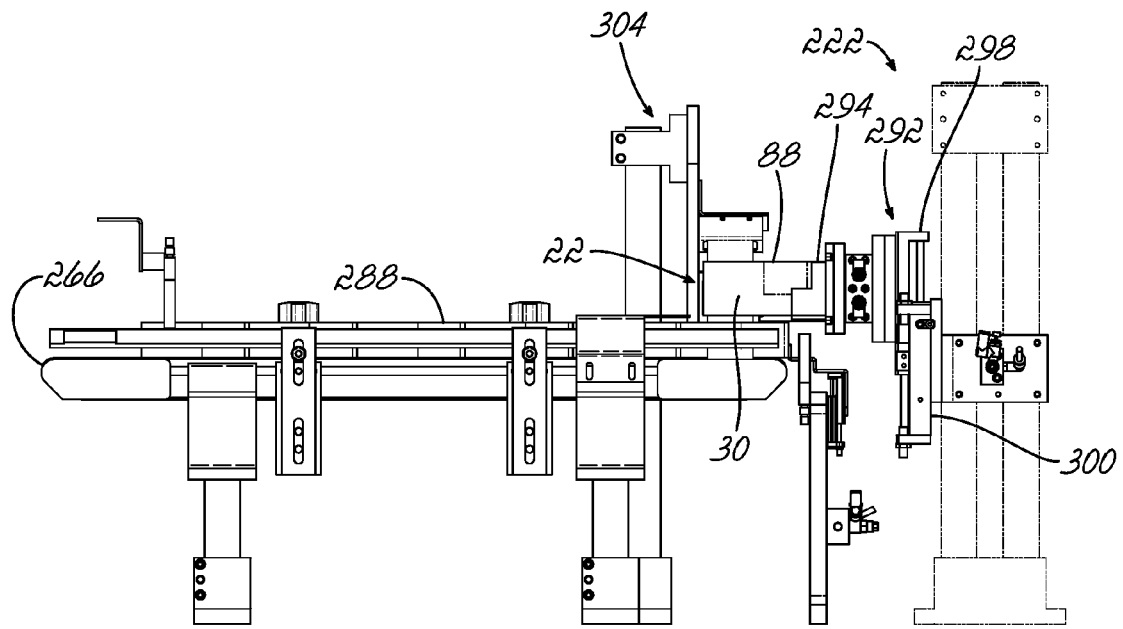
Figure 22:
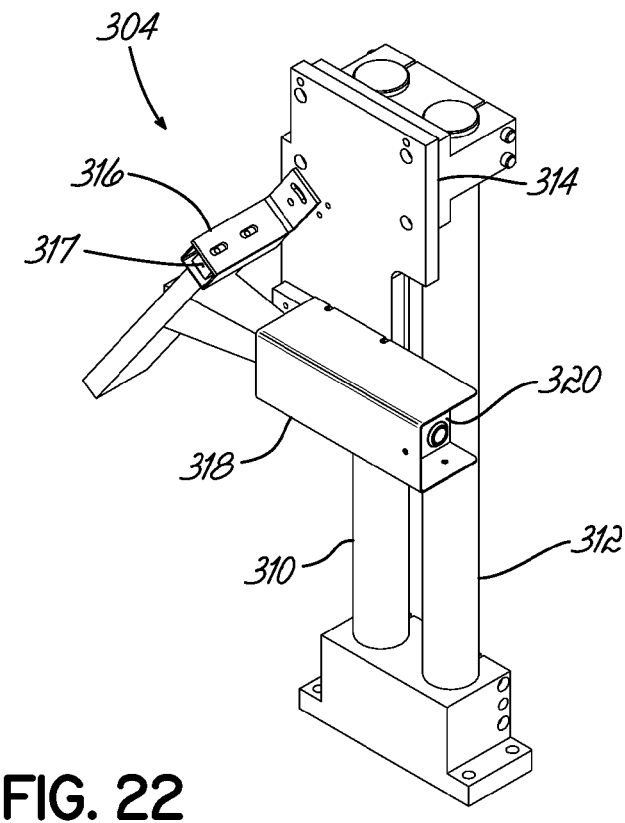
FIG. 22 is a perspective view of a camera assembly associated with the box infeed conveyor of the ALV machine.
Figure 23:
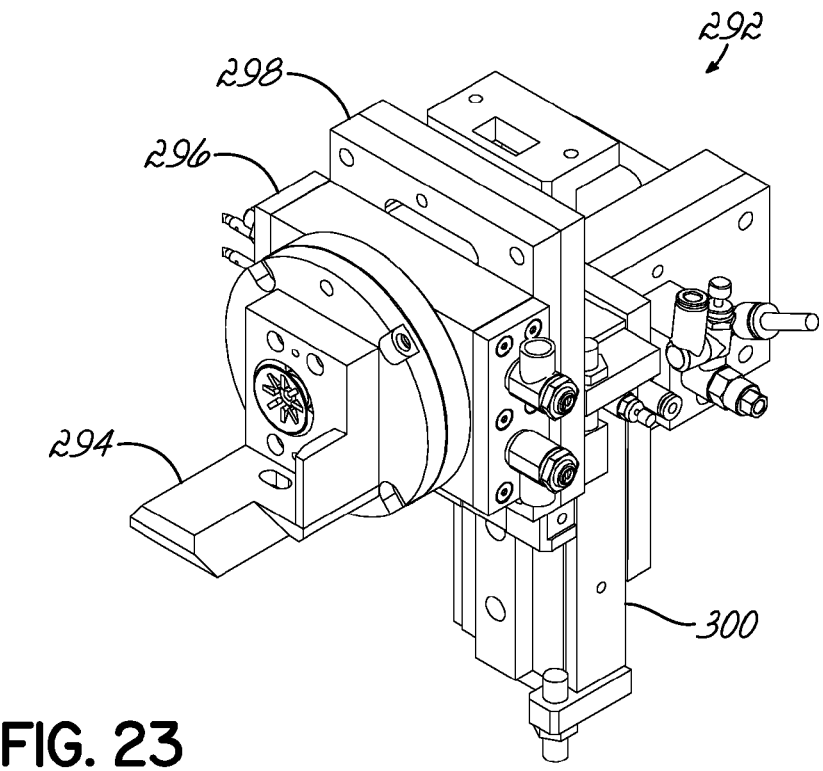
FIG. 23 is a perspective view of a box rotation mechanism associated with the box infeed conveyor of the ALV machine.

FIGS. 9-15 illustrate the components of the card loading station 60 in further detail. The card loading station 60 includes a product induction magazine 150 for feeding blister cards 20 picked by the operator to the loading station of the ALV machine 50 and a camera assembly 152 for verifying the product barcode 24 (FIG. 6) on the blister cards 20. In FIGS. 9-11, the product induction magazine 150 is loaded with numerous blister cards 20. In FIGS. 12-14, the product induction magazine 150 is in a substantially empty condition and the camera assembly 152 hidden for clarity.

The product induction magazine 150 includes a feed chute defined by a set of columnar guide posts 154 and a pair of movable arms 156, 158 that are arranged to extend and retract through respective gaps between an adjacent pair of guide posts 154 into the space inside the chute. The guide posts 154, which are formed from right angle bar stock, have concave L-shaped vertical channels arranged relative to each other to correlate with the shape of blister cards 20 so that the outside corners of the blister cards 20 project into the concave vertical channel of the nearest guide post 154. At the top entrance of the chute, the channel of each of the guide posts 154 is flared outwardly to increase the cross-sectional area available to receive the blister cards 20, which eases introduction of blister cards 20 dropped by the operator into the chute.

Each of the arms 156, 158 is coupled mechanically with a respective linear motion mechanism in the form of a linear actuator 162, 164, for movement relative to the chute between extended and retracted positions. When the arms 156, 158 are placed in the extended position, a portion of each of the arms 156, 158 contacts and supports opposite sides of the bottom blister card 20 in a stack of blister cards 20 manually dropped by the operator into the chute of the product induction magazine 150. The channels of the guide posts 154 collectively guide the vertical movement of the blister cards 20 from the top of the feed chute downward so that the bottom blister card 20 in the stack rests on the arms 156, 158. When the controller instructs both linear actuators 162, 164 to withdraw the arms 156, 158 outwardly to the retracted position, the group of blister cards 20 is no longer supported and falls under the influence of gravity. The guide posts 154 collectively guide this downward movement until the bottom blister card 20 in the stack rests on a landing plate 166 located beneath the arms 156, 158. The stack of blister cards 20 resting on the landing plate 166 is then singulated by the product induction magazine 150, as described below.

When positioned on the landing plate 166, a portion of the bottom blister card 20 overhangs a portion of a nesting plate 170 located adjacent to, and in a plane slightly below, the landing plate 166. A riser 172 may be provided on the landing plate 166 to further elevate the overhanging portion of the blister card 20 relative to the nesting plate 170. The nesting plate 170 includes a pair of parallel slots 174, 176 and guide rails 178, 180 running along its length. To move the bottom blister card 20 away from the stack in the chute and along the nesting plate 170, the product induction magazine 150 further includes a gripping device 182 having a set of suction members 184a-d carried on respective vertical spacer posts 186a-d, a linear motion mechanism 188 for laterally shifting a base plate 190 that supports the vertical spacer posts 186a-d, and a vertical motion mechanism 192 for vertically shifting the base plate 190. The gripping device 182 is positioned so that the suction members 184a-d are configured to extend through the slots 174, 176 in the nesting plate 170. Initially the linear motion mechanism 188, which is in the form of a linear actuator in the representative embodiment, positions the base plate 190 under the portion of the nesting plate 170 proximate the landing plate 166. The vertical motion mechanism 192, which is also in the form of a linear actuator in the representative embodiment, raises the base plate 190 until the suction members 184*a-d* are immediately adjacent to and/or in contact with the overhanging portion of the blister card 20 on the landing plate 166.

Suction is supplied to the suction members 184*a-d* from a vacuum source (not shown) so that the suction members 184*a-d* aspirate the air from any space between the suction members 184*a-d* and the blister card 20 on the landing plate 166 to apply an attractive force that engages the overhanging portion of the blister card 20 with the suction members 184*a-d*. With the blister card 20 so grasped, the vertical motion mechanism 192 moves the base plate 190 and suction members 184*a-d* downward by a distance sufficient for the leading end of the blister card 20 to clear a bottom edge 194 of a blocking plate 196. The linear motion mechanism 188 then shifts the base plate 190 horizontally by a distance sufficient to move the blister card 20 past the blocking plate 196 and out of the chute. The guide rails 178, 180 provided on the nesting plate 170 help guide this horizontal movement.

The blister card 20 is brought to a "dead area" location on the nesting plate 170 accessible by the robot 66 (FIG. 3) of the transfer station 64. At this point, the suction members 184*a-d* are vented to release the attractive force applied to the singulated blister card 20. The linear motion mechanism 188 and vertical motion mechanism 192 then return to their initial positions, ready to singulate the next blister card 20 in the stack. The solenoid valves for the linear motion mechanism 188, vertical motion mechanism 192, and vacuum source for the suction members 184*a-d* are electrically coupled with, and controlled by, the controller. Sensors (not shown) are provided that detect the presence of one or more blister cards 20 captured by the arms 156, 158 and one of the blister cards 20 residing on the landing plate 166. These sensors supply feedback to the controller for operating the solenoid valves for the linear motion mechanism 188, vertical motion mechanism 192, and vacuum source for the suction members 184*a-d*. A sensor 200 is also mounted to the nesting plate 170 to detect when a blister card 20 has been delivered to the dead area.

Before being transferred to the dial conveyor 68, the product barcode 24 on each of the singulated blister cards 20 is verified by the camera assembly 152. The camera assembly 152 includes a pair of vertical shafts 210, 212 that support a camera mount 214 and camera cover 216 above the nesting plate 170. A camera 215 held by the camera cover 216 is configured to take one or more images of the product barcode 24 on the blister card 20 singulated onto the nesting plate 170. The controller activates the camera 215 when the sensor 200 detects the presence of the blister card 20. To aid in capturing the images, a lighting assembly 218 is mounted to the nesting plate 170 and configured to emit light toward the product barcode 24. The controller analyzes the images captured by the camera 215 using machine vision software. In alternative embodiments, the card loading station 60 may include a laser scanner (not shown) configured to read the product barcode 24 and communicate a corresponding string of characters to the controller using electrical signals.

Regardless of which type of barcode reader is used in the card loading station 60, the controller of the ALV machine 50 individually verifies the product barcode 24 of the singulated blister card 20 against the expected pick requests from the pharmacy host. This aids in ensuring that each of the blister cards 20 processed by the card loading station 60 matches any one of the expected products 12 in the tracking data for the pick batch introduced into the product induction magazine 150.

(d) Box Loading Station

FIGS. 16-23 illustrate the components of the box loading station 62 (FIG. 3) in further detail. The box loading station 62 includes three main component assemblies: a loading conveyor assembly 220 onto which boxes 22 collected by an operator are deposited, an infeed conveyor assembly 222 for delivering the boxes 22 to the transfer station 64, and a transfer assembly 224 for transferring boxes 22 from the loading conveyor assembly 220 to the infeed conveyor assembly 222. The loading conveyor assembly 220 includes a load conveyor 230 supported by a frame 232 and readily accessible by an operator. Because the load conveyor 230 is arranged generally across the front of the ALV machine 50 (see FIG. 5), the operator can deposit a number of the boxes 22 along the length of the load conveyor 230.

A transfer stand 234 with a top surface 236 adjacent the load conveyor 230 is provided to increase the amount of available area for receiving the boxes 22. The transfer stand 234 also provides an area for arranging the boxes 22 to have the same orientation before sliding them onto the load conveyor 230. For example, the operator may drop the collected boxes 22 onto the transfer stand 234 and then arrange each of them so that a top surface 238 faces a first guide rail 240 that runs along the length of the load conveyor 230 and so that their sidewall 28 with the product barcode 24 faces upwardly. The boxes 22 can then be slid across the top surface 236 of the transfer stand 234 and onto the load conveyor 230 until their top surface 238 abuts the first guide rail 240. Alternatively, the operator may properly orient each box 22 before depositing them directly on the load conveyor 230. Arranging the boxes 22 to have the same orientation ensures that their product barcodes 24 follow the same workflow path.

The load conveyor 230 moves the boxes 22 in the direction generally indicated by arrows 244. Before reaching an end 246 of the load conveyor 230, the boxes 22 are pushed against a second guide rail 248 by a pusher assembly 250. The pusher assembly 250 is located in line with the first guide rail 240 and includes a contact member 252 driven by a linear actuator 254 in a direction transverse to the direction 244 of the load conveyor 230. By pushing each box 22 against the second guide rail 248, the pusher assembly 250 ensures that the boxes 22 are similarly positioned when they reach the end 246 of the load conveyor 230. Sensors 256, 258, 260 verify the position and orientation of each box 22 at the end 246 of the load conveyor 230.

The infeed conveyor assembly 222 includes an infeed conveyor 266 generally arranged perpendicular to the load conveyor 230. Thus, as the boxes 22 reach the end 246 of the load conveyor 230, they must be pushed forward onto the infeed conveyor 266. This transfer step is accomplished by the transfer assembly 224, which includes transfer arm 270 generally parallel to the direction 244, a first linear actuator 272 coupled to the transfer arm 270 and generally aligned in a direction perpendicular to the direction 244, and a second linear actuator 274 coupled to the first linear actuator 272 and generally aligned in a direction parallel to the direction 244. The transfer arm 270 extends through a slot 276 provided in a frame 278, which includes one or more spacer plates 280 positioned above the load conveyor 230 at the end 246. Boxes 22 that reach the end 246 of the load conveyor 230 momentarily rest against the spacer plate 280 as the load conveyor 230 continues to move underneath the boxes 22.

In an initial position, the first and second linear actuators 272, 274 are in extended states with transfer arm 270 is positioned adjacent the second guide rail 248. The transfer arm 270 does not interfere with movement of the boxes 22 to the end 246 of the load conveyor 230. After the sensors 256, 258, 260 verify the box 22 position and orientation, the first linear actuator 272 retracts to move the transfer arm 270 in a direction transverse to the direction 244 thereby pushing the box 22 onto the infeed conveyor 266. The second linear actuator 274 then retracts to move the first linear actuator 272 and transfer arm away 270 from the infeed conveyor 266. At this point, the first linear actuator 272 moves back to an extended state so that the transfer arm 270 is generally aligned with the second guide rail 248 again. Finally, the second linear actuator 274 moves back into an extended state as well so that the transfer arm 270 is adjacent the second guide rail 248 and ready to push the next box 22 that has moved to the end 246 of the load conveyor 230. The transfer process described above is repeated for each successive box 22 on the load conveyor 230. As a result, the arrangement of the boxes 22 is transformed from a side-by-side arrangement on the load conveyor 230 to an end-by-end arrangement on the infeed conveyor 266.

The infeed conveyor 266 is supported by a frame 286 having guide rails 288, 290 for directing the boxes 22 as they move in the machine direction of the infeed conveyor 266. The boxes 22 move along the infeed conveyor 266 until they reach a box rotation mechanism 292, which includes a bracket 294 configured to support a portion of the box 22, a rotary actuator 296 coupled to the bracket 294, a frame 298 supporting the rotary actuator 296, and a linear actuator 300 for moving the frame 298 vertically. The bracket 294 initially forms a product stop for the box 22 at the end of the infeed conveyor 266. Once a sensor 302 determines that a box 22 has reached the end of the infeed conveyor 266, the linear actuator 300 raises the frame 298 and the rotary actuator 296 rotates the bracket 294. This results in the box 22 being raised and rotated so that the front surface 88 is aligned in a horizontal plane (i.e., faces up) and the sidewalls 28, 30 are aligned in vertical planes. This also results in the box 22 being elevated to a position where the product barcode 24 on the sidewall 28 can be easily read by a camera assembly 304.

To this end, the camera assembly 304 includes a pair of shafts 310, 312 that support a camera mount 314 having a lighting assembly 316 and camera cover 318 attached thereto. The lighting assembly 316 is positioned so that a lighting device 317 emits light onto the product barcode 24 of the box 22 after it has been raised and rotated by the box rotation mechanism 292. The camera cover 318 is configured to support a camera 320 that faces the product barcode 24 in this position. Similar to the camera assembly 152 of the card loading station 60, the camera 320 takes images of the product barcode 24 that are analyzed by the controller using machine vision software. The camera 320 may also be replaced with a laser scanner (not shown) in alternative embodiments. Regardless of which type of barcode reader is used, the ALV machine 50 individually verifies the product barcode 24 of the boxes 22 against the expected pick requests from the pharmacy host. This aids in ensuring that each of the boxes 22 processed by the box loading station 62 matches any one of the expected products 12 in the tracking data for the pick batch.

(e) Transfer Station and Dial Conveyor

Figure 3:
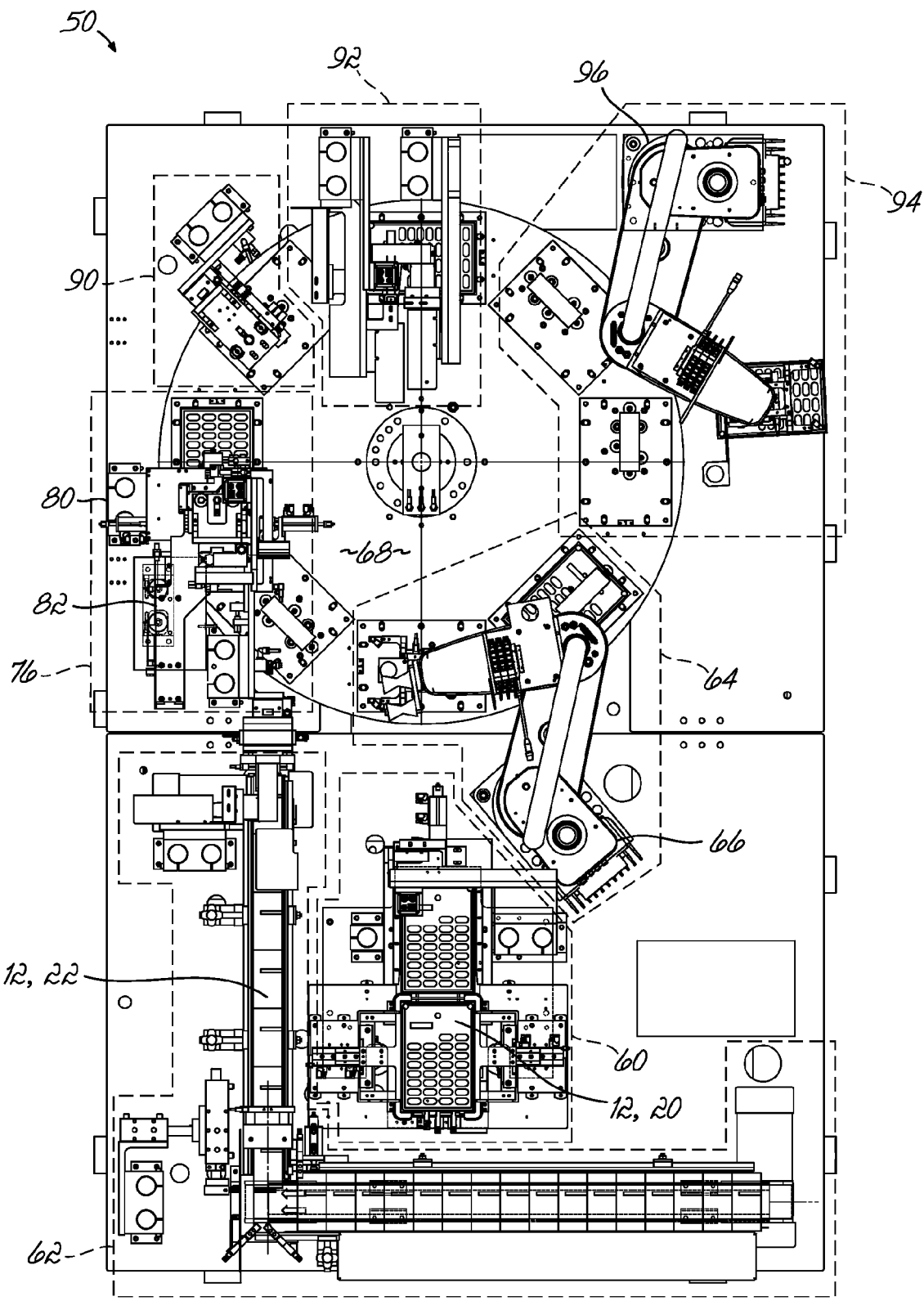
FIG. 3 is a top plan view showing the layout of an ALV machine in the ALV system of FIG. 1.
Figure 4:
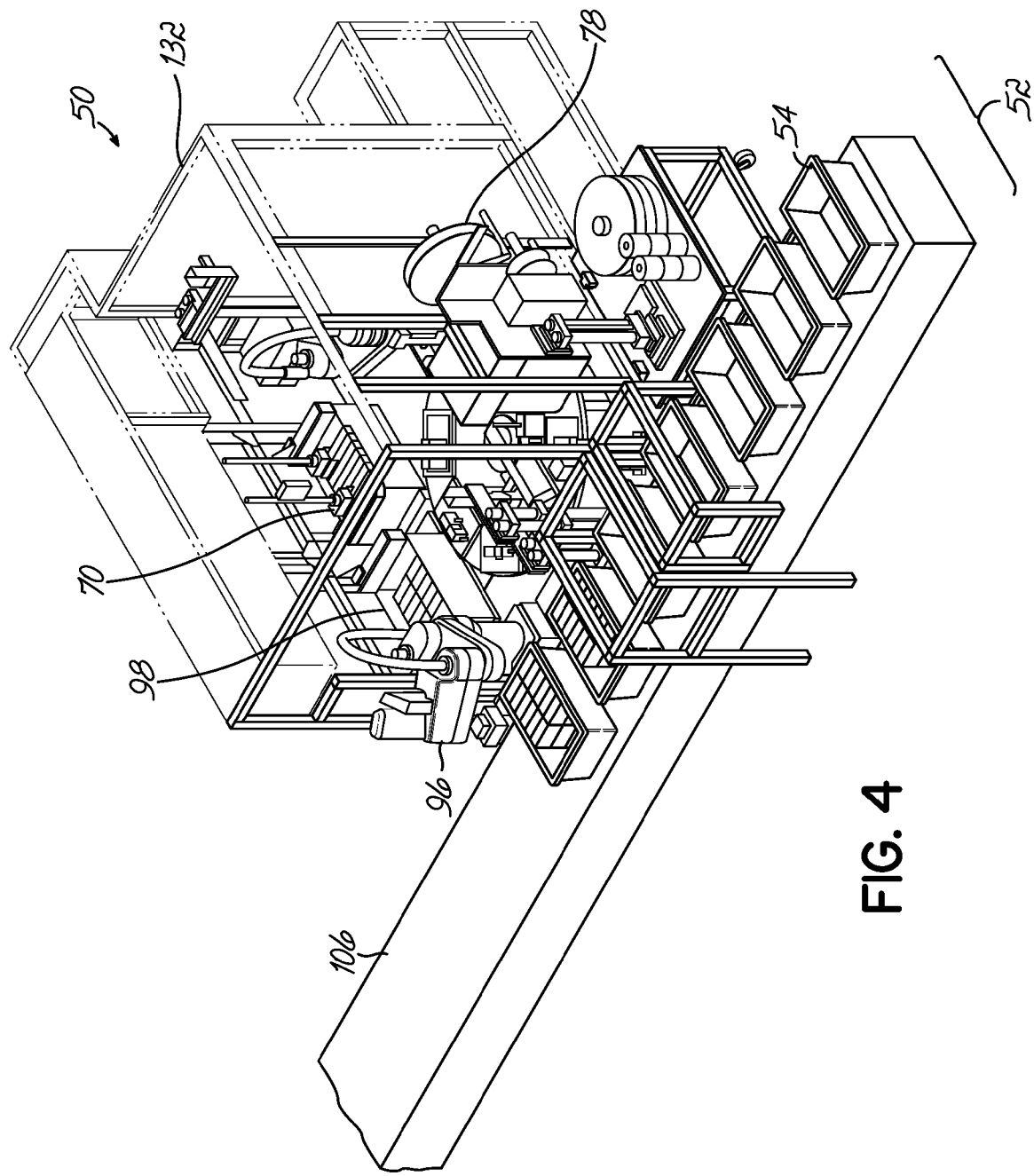
FIG. 4 is a perspective view of the ALV machine and a portion of a tote conveyor system of the ALV system.
Figure 24:
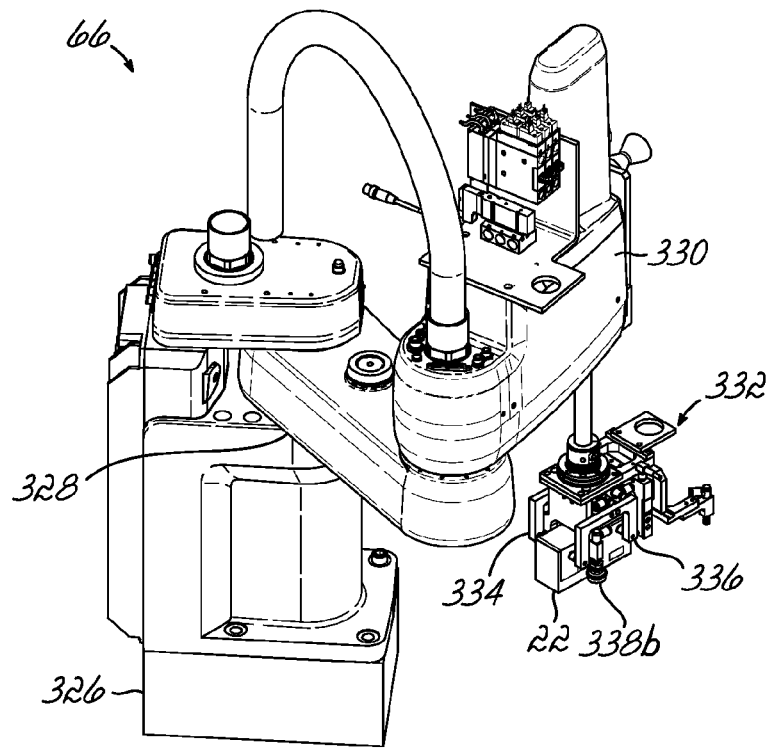
FIGS. 24 and 25 are perspective and side elevation views, respectively, of a robot used to transfer products from the product induction magazine and box infeed conveyor to the ALV machine.
Figure 25:
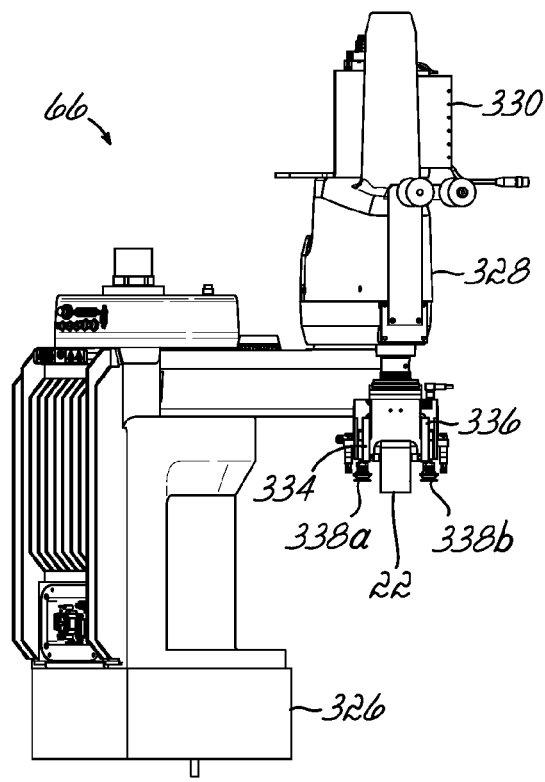

With reference to FIGS. 3, 24, and 25, the transfer station 64 is generally represented by the robot 66, which is illustrated as having a SCARA (selective compliance assembly robot arm) configuration. The robot 66 includes a base 326, a first arm 328 pivotally coupled to the base 326 in an X-Y direction, and a second arm 330 pivotally coupled to the first arm 328 in the X-Y direction. An end effector or wrist 332 associated with the first arm 328 is configured to move in a Z-direction and pick up products 12 having the different form factors. More specifically, the end effector 332 includes gripping members 334, 336 that move toward each other to grasp the sidewalls 28, 30 of one of the boxes 22 and suction members 338*a*, 338*b* that are operated by a vacuum source (not shown) to establish and maintain engagement with the front surface 26 of one of the blister cards 20. In one specific embodiment, the robot 66 may be an Adept Cobra™ SCARA robot available from Adept Technologies, Inc. Other robot configurations, such as a Cartesian configuration, may be used in alternative embodiments. Those skilled in the art will appreciate that regardless of the configuration, the robot 66 may include various motion controller and electronic system devices, such as limit switches, sensors, input/output terminals, amplifiers, pneumatic valves, fittings, solenoids, power supplies, programmable controllers, servo motors, and belt pulley drives for performing the required movements.

Figure 45:
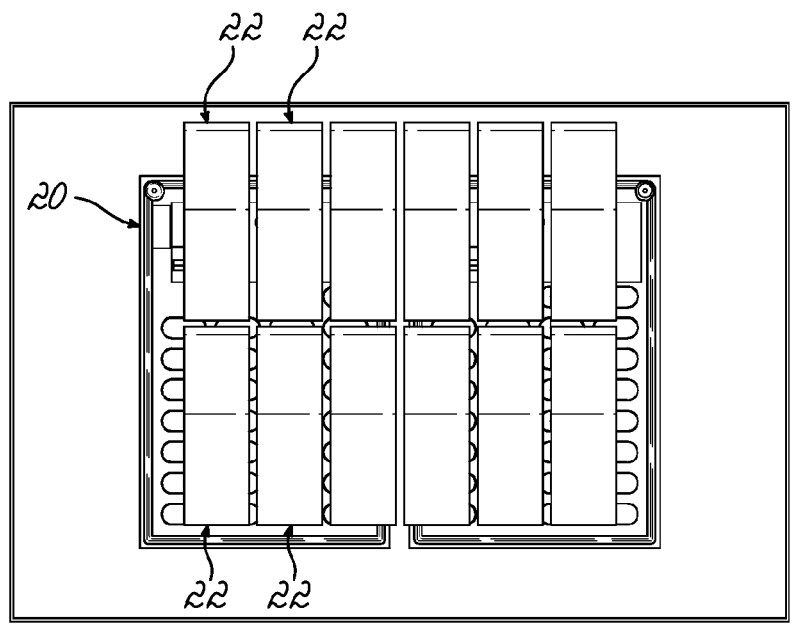
FIG. 45 is a schematic view illustrating how products may be deposited into a container in an organized manner.
Figure 46:
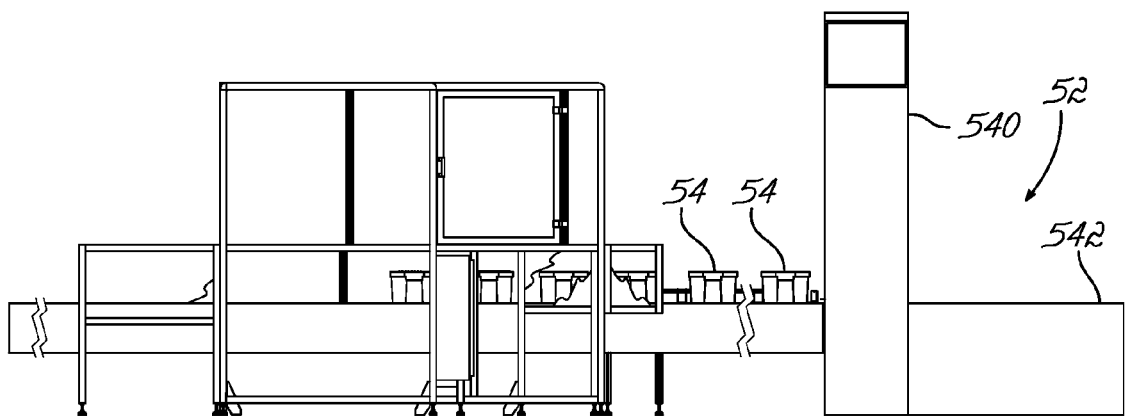
FIG. 46 is a rear elevation view of a tote conveyor system of the ALV system.
Figure 47:
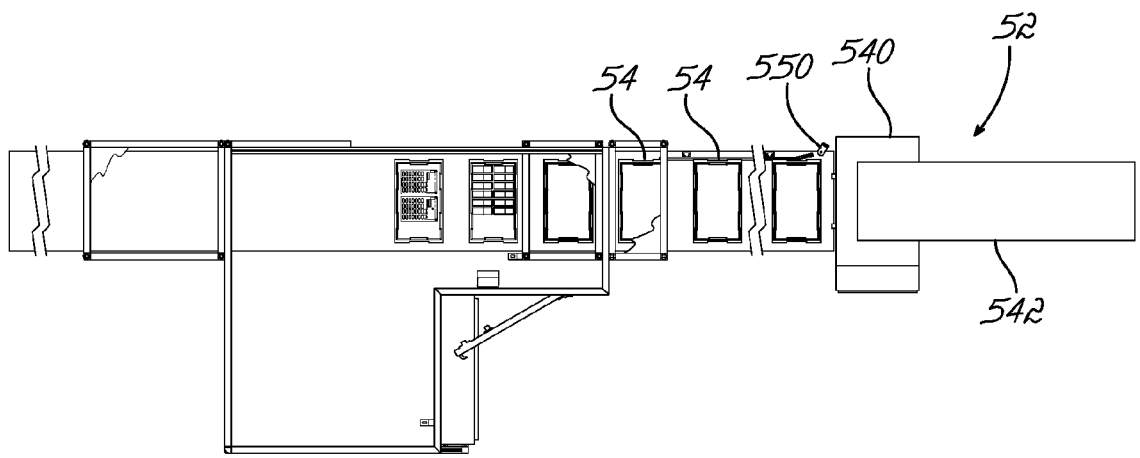
FIG. 47 is a top plan view of the tote conveyor system of FIG. 46.
Figure 48:
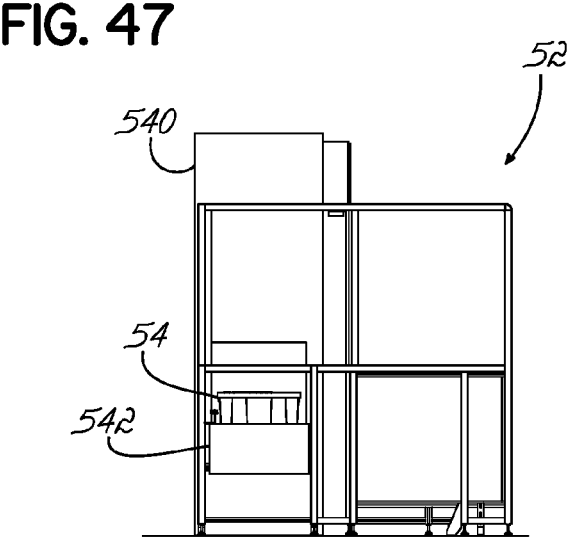
FIG. 48 is a side elevation view of the tote conveyor system of FIG. 46.
Figure 49:
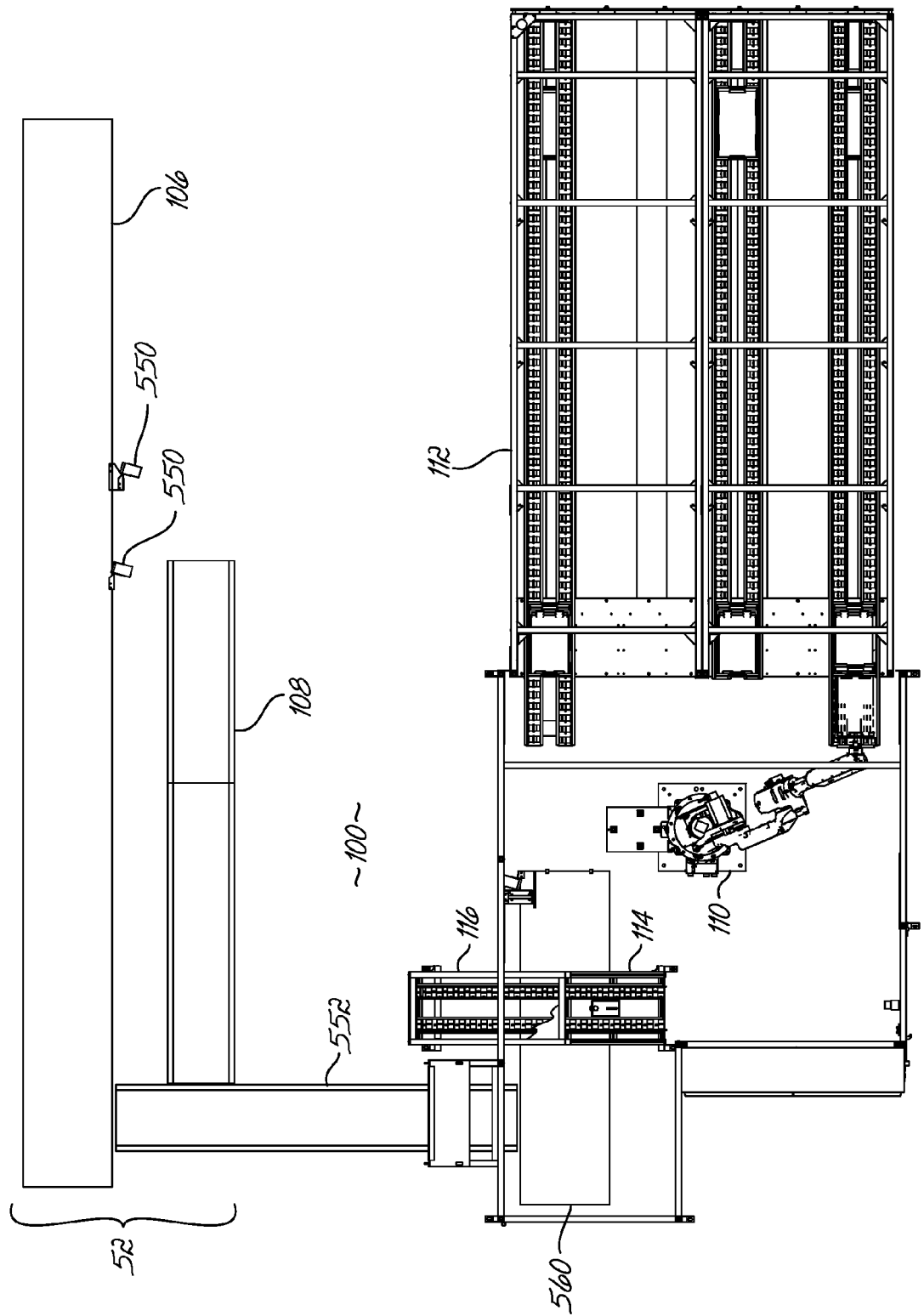
FIG. 49 is a top plan view of a tote handling system of the ALV system.
Figure 49A:
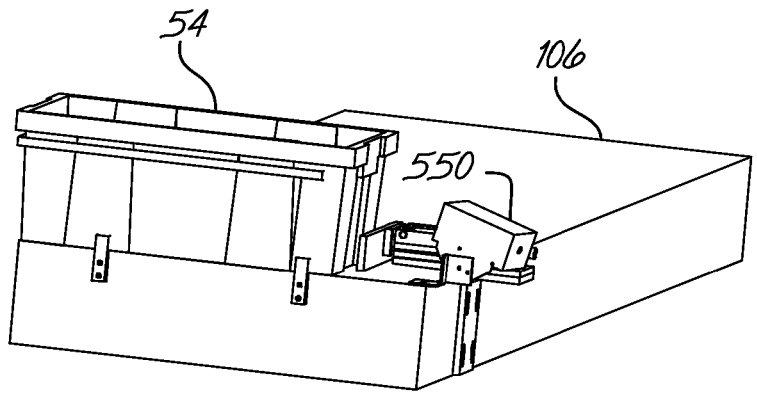
FIG. 49A is a perspective view schematically illustrating a barcode reader of the tote conveyor system of FIG. 46.
Figure 50:
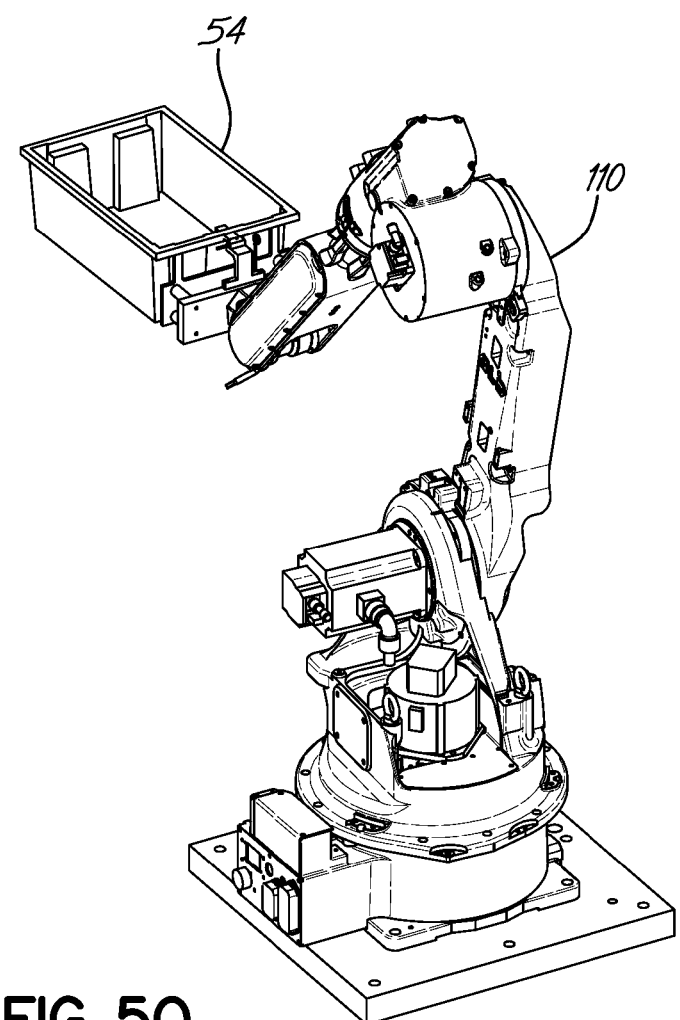
FIG. 50 is a perspective view of a tote load robot of the tote handling system of FIG. 49.
Figure 51:
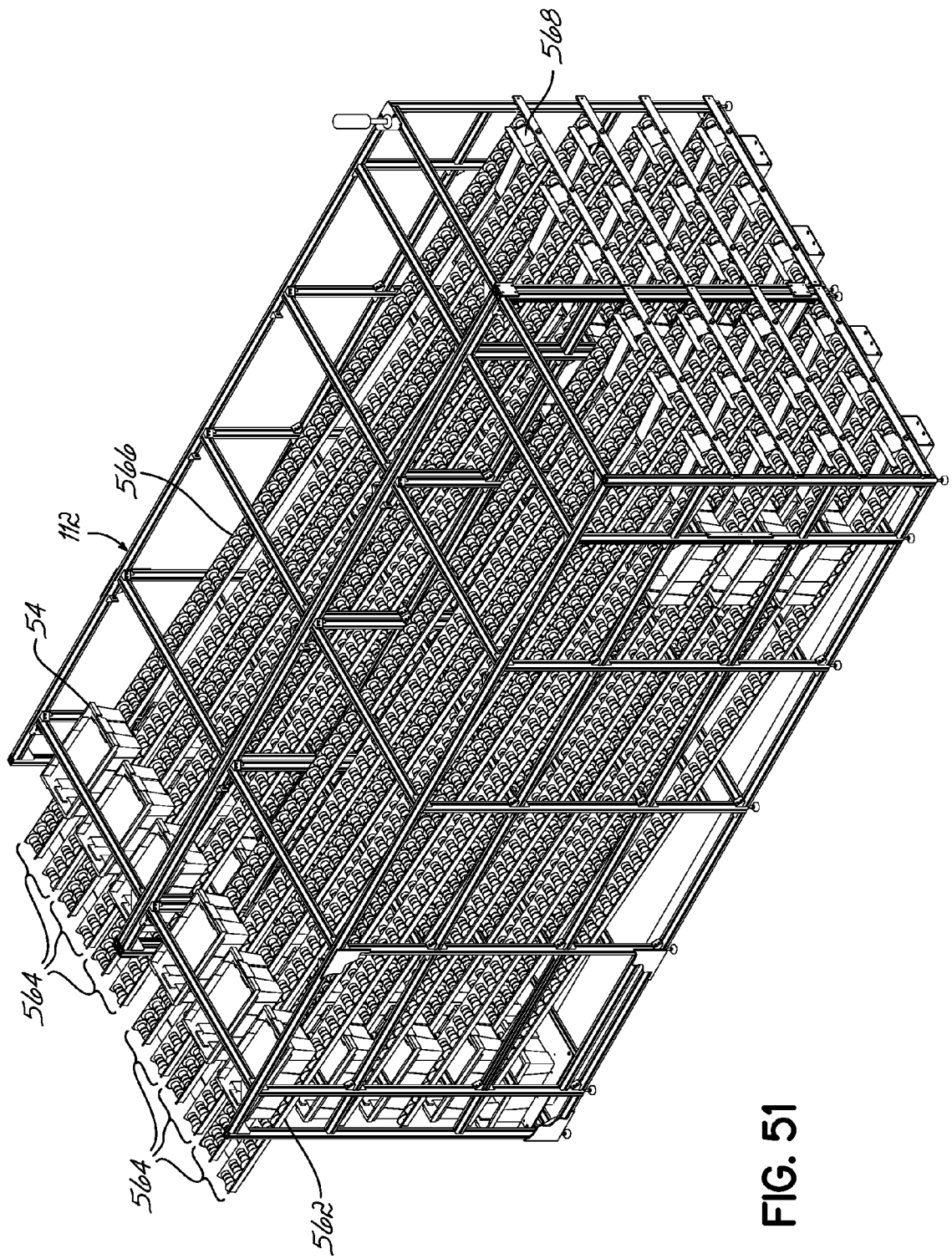
FIG. 51 is a perspective view of a tote rack of the tote handling system of FIG. 49.
Figure 52:
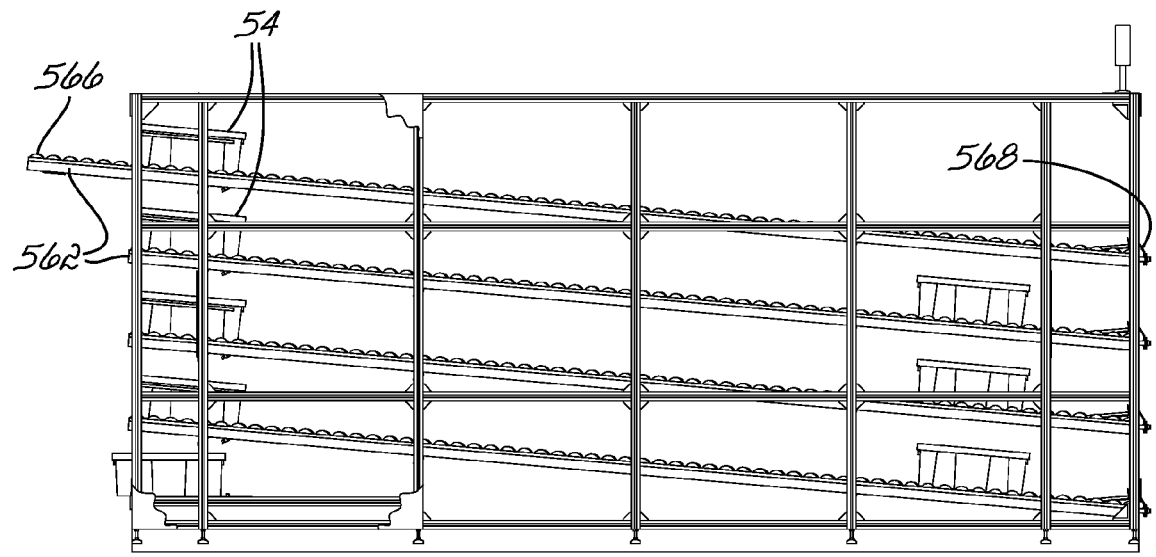
FIG. 52 is a side elevation view of the tote rack of FIG. 51.
Figure 53:
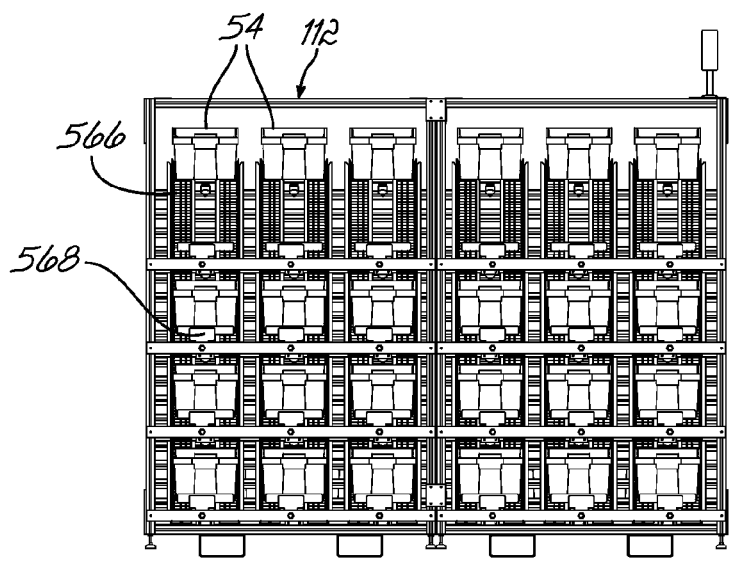
FIG. 53 is a front elevation view of the tote rack of FIG. 51.

As discussed above, the card loading station 60 delivers blister cards 20 and the box loading station 62 delivers boxes 22 to respective locations that are readily accessible by the robot 66. Products 12 that have failed verification and been signaled as rejects are gripped and transferred by the robot 66 into the first reject bin 70 (FIG. 5). The robot 66 deposits rejected products 12 in an organized manner that makes efficient use of available space. For example, as shown in FIG. 45, blister cards 20 and boxes 22 (shown as overlapping for the purpose of explanation) placed by the robot 66 may be stacked on top of or deposited immediately adjacent to other blister cards 20 or boxes 22. An increased number of blister cards 20 and boxes 22 can be deposited into the first reject bin 70 when providing such an organized arrangement than when randomly depositing rejected blister cards 20 and boxes 22 into the first reject bin 70.

Products 12 that have been successfully verified at either the card loading station 60 or box loading station 62 are gripped and transferred by the robot 66 onto a base plate 344 (FIG. 26) of a product nesting assembly 346 carried by the dial conveyor 68. There are a total of eight base plates 344 (and corresponding product nesting assemblies 346) on the dial conveyor 68 so that the ALV machine 50 can simultaneously process multiple products 12, with different products 12 undergoing different processing steps. The dial conveyor 68 rotates so that the base plates 344 follow a circular workflow path, but pauses after each $\frac{1}{8}^{th}$ turn to allow time to process the products 12 at the various stations located in the workflow path. Thus, there are a total of eight indexed locations associated with the workflow path of the dial conveyor 68. The two locations within the transfer station 64 schematically outlined in FIG. 3 are where the robot 66 deposits the verified products 12.

As shown in FIGS. 27-30, each nesting assembly 346 is advantageously configured to support and stabilize products 12 having different form factors. The nesting assemblies 346 each include the base plate 344 supported on the dial conveyor 68 and a pin plate 350 hanging below the dial conveyor 68. The base plate 344 is generally planar, but has several card locating pins 352 spaced about its periphery and extending upwardly. The card locating pins 352 help define a bounded area on the base plate 344 for containing blister cards 20 deposited by the robot 66. Thus, the robot 66 places blister cards 20 into the area between the card locating pins 352, which prevent the deposited blister card 20 from shifting on the base plate 344 as it is processed in the workflow path of the dial conveyor 68.

The pin plate 350 is configured to be received in a window or opening (not shown) of the dial conveyor 68 below the base plate 344. In an initial position, however, the pin plate 350 hangs below the window and rests on opposed supports 358, 360 suspended from the base plate 344 by respective pairs of guide shafts 362, 364. The pin plate 350 is movable along the guide shafts 362, 364 and includes box locating pins 366 of various sizes extending upwardly toward the base plate 344. The box locating pins 366 are configured to extend through holes 368 in the base plate 344 when the pin plate 350 is moved upwardly along the pairs of guide shafts 362, 364 and into the window of the dial conveyor 68. When moved to such a position, the box locating pins 366 help define a bounded area on the base plate 344 for containing boxes 22 placed by the robot 66. Thus, the box locating pins 366 are analogous to the card locating pins 352 in that they prevent the deposited box 22 from shifting on the base plate 344 as it is processed in the workflow path of the dial conveyor 68. The pin plate 350 also includes a downwardly extending shaft 370 that terminates in a flange 372.

Figure 26:
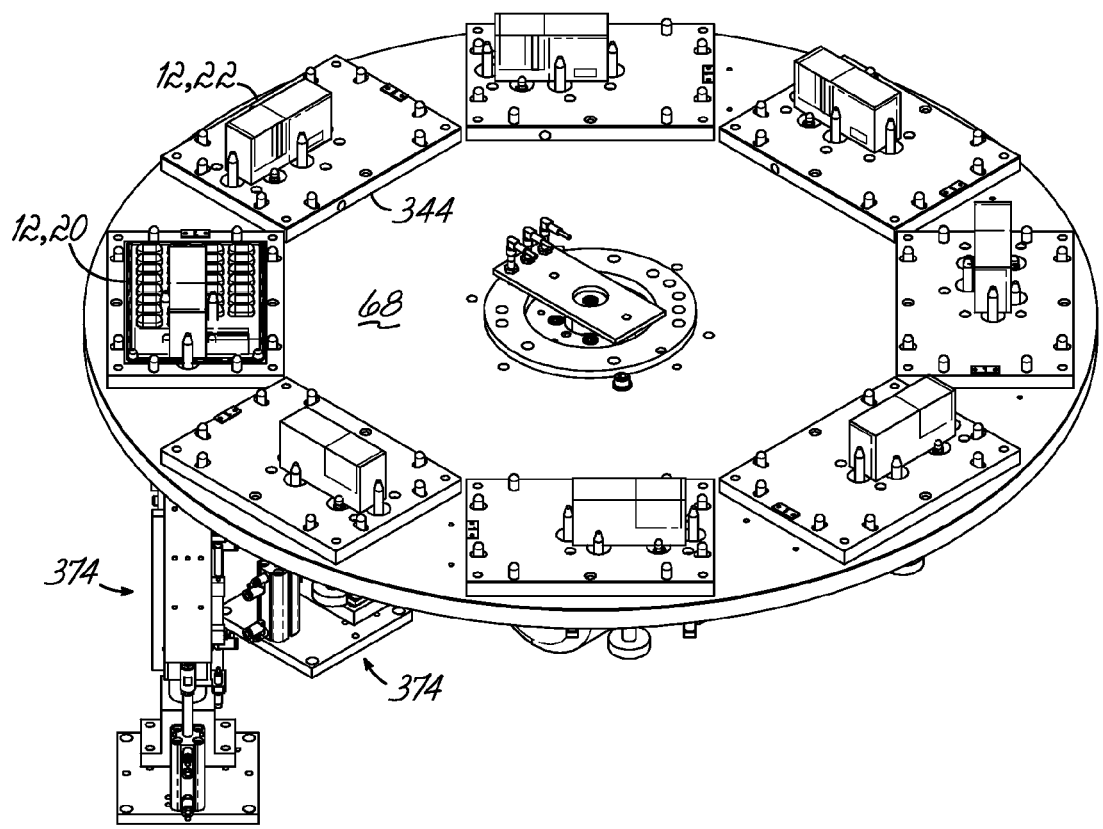
FIG. 26 is a perspective view of a dial conveyor of the ALV machine.
Figure 27:
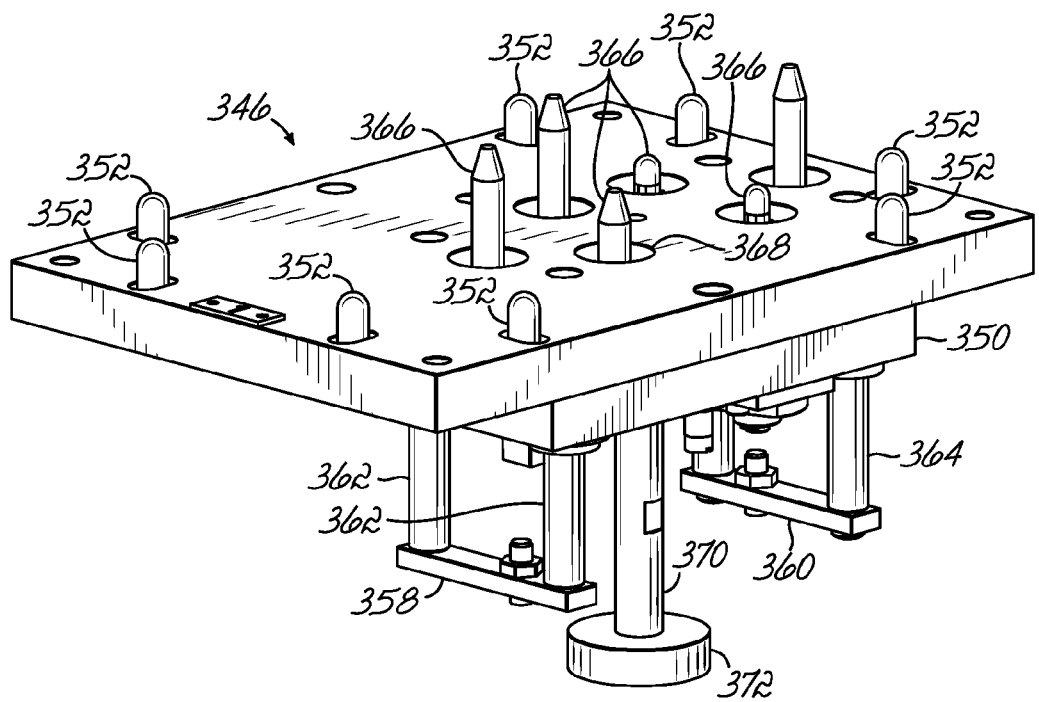
FIG. 27 is a perspective view of a nesting assembly supported by the dial conveyor of FIG. 26.
Figure 28:
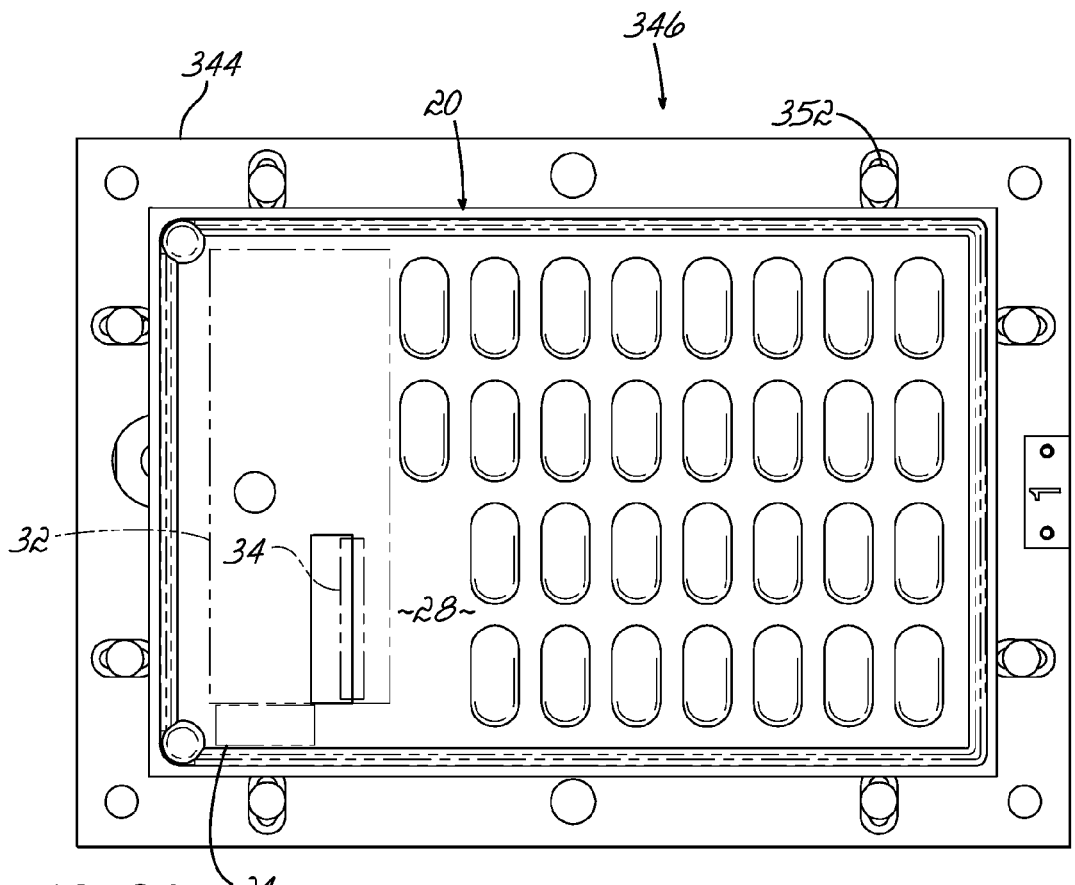
FIG. 28 is a top plan view of the nesting assembly with a blister card positioned on a nesting plate.
Figure 29:
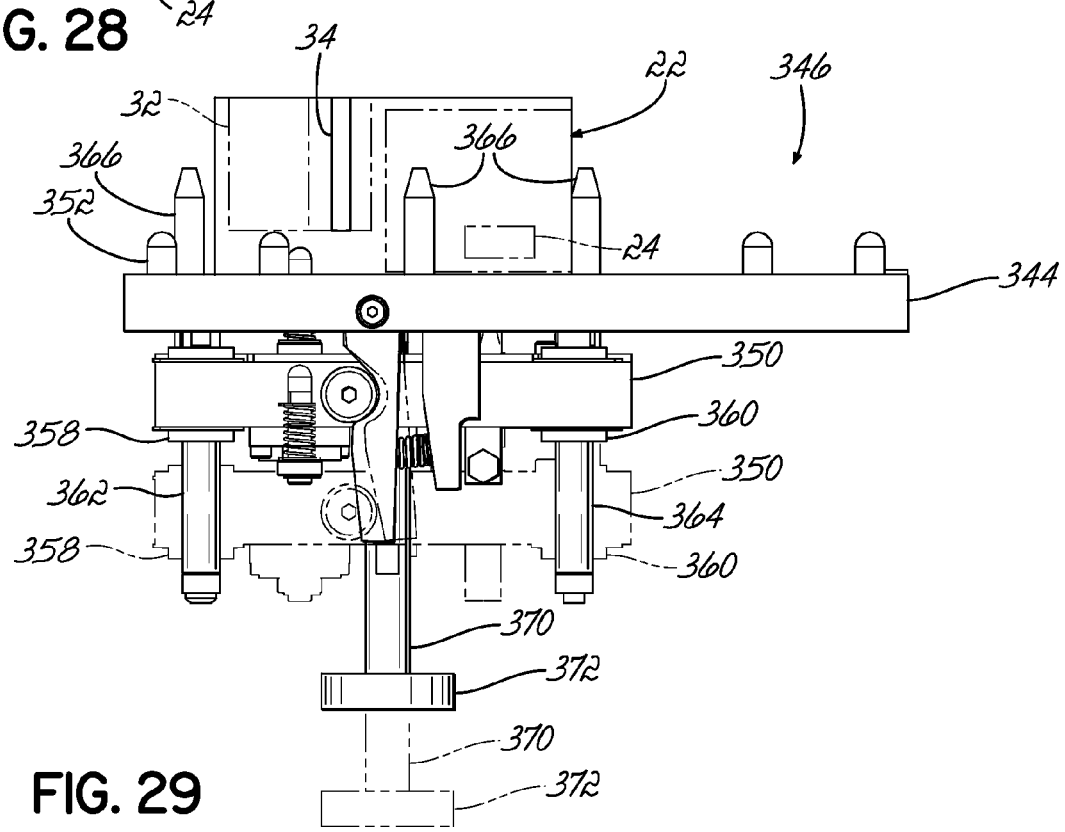
FIGS. 29 and 30 are side and front elevation views, respectively, of the nesting assembly with a box positioned on the nesting plate.
Figure 30:
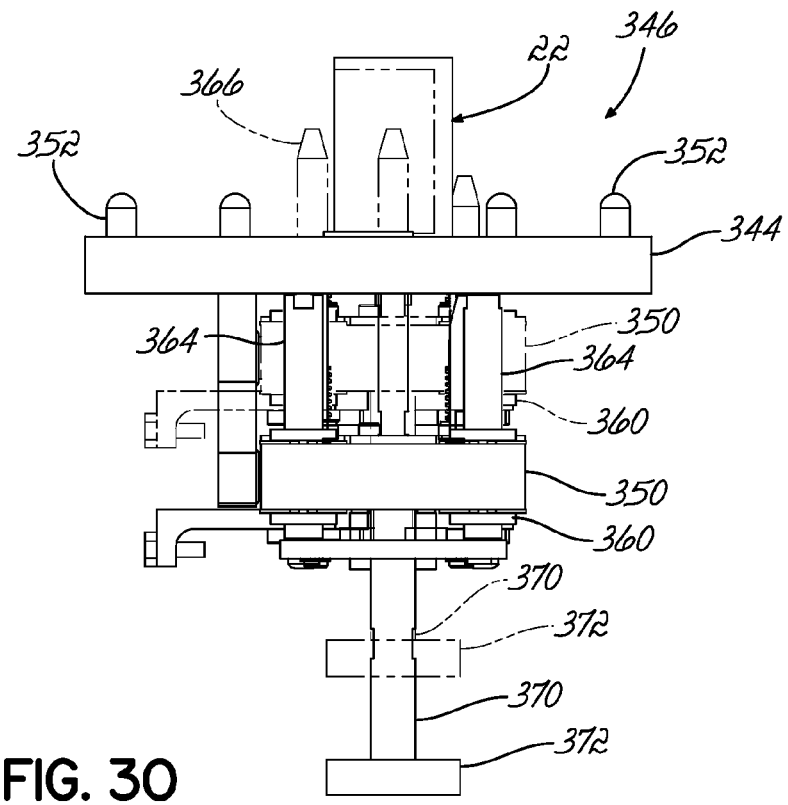
Figure 31:
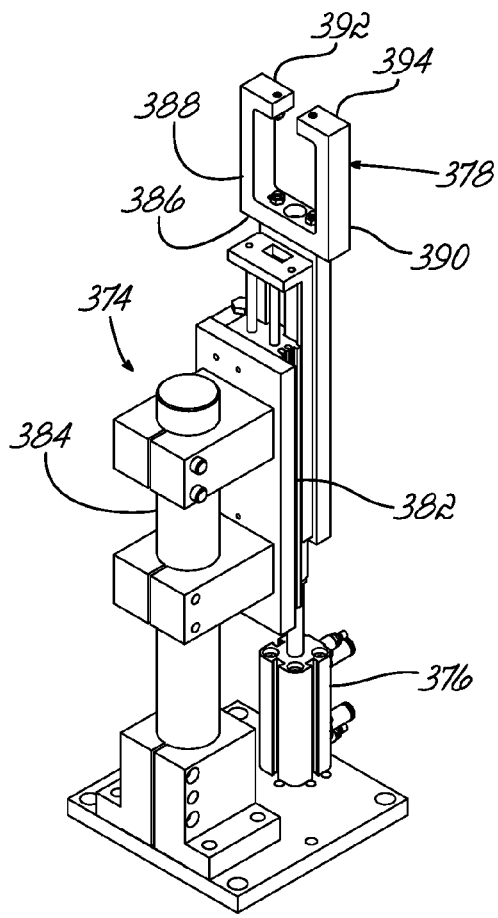
FIG. 31 is a perspective view of a lifting assembly configured to raise and lower the nesting assembly of FIG. 27.
Figure 32:
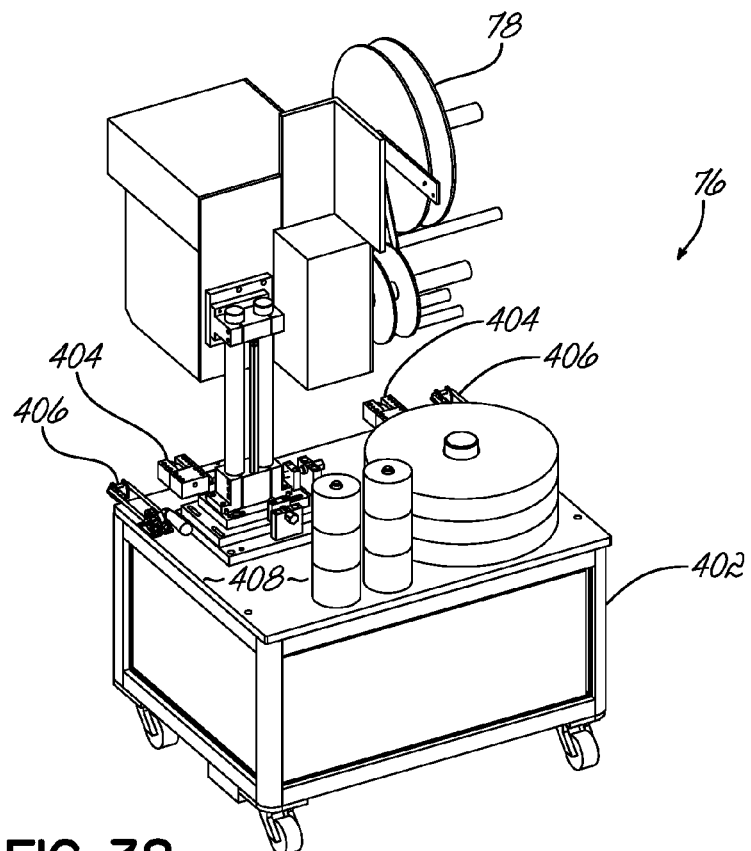
FIGS. 32 and 33 are perspective and side elevation views, respectively, of one embodiment of a label printer used with the ALV machine.
Figure 33:
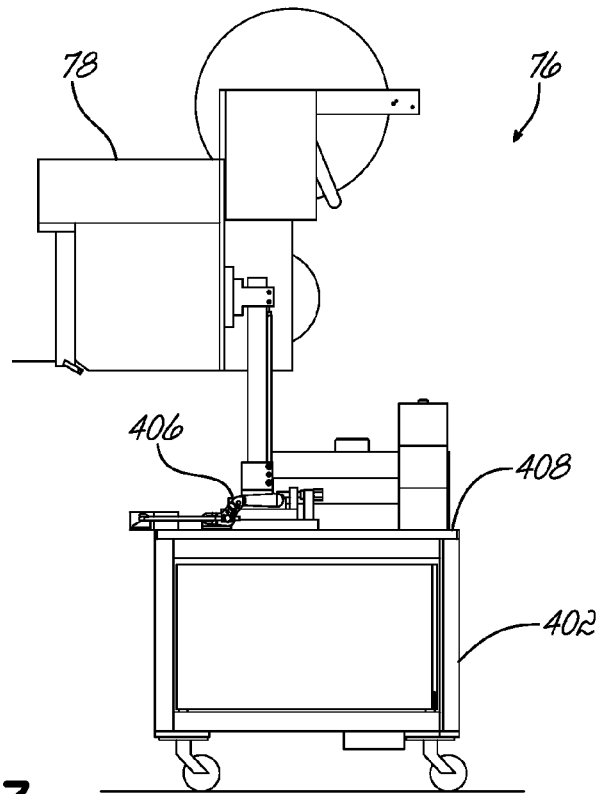

With reference to FIGS. 26 and 31, the ALV machine 50 includes two lifting assemblies 374 for controlling the vertical movement of the pin plates 350 at the two indexed locations associated with the transfer station 64. Each lifting assembly 374 includes a vertical motion mechanism 376 in the form of a linear actuator, an adaptor collar 378 driven by the vertical motion mechanism 376, and a guide plate 382 mounted to a support post 384 for guiding movement of the vertical motion mechanism 376. The adaptor collar 378 is generally a U-shaped bracket having a base 386, opposed arms 388, 390 extending upwardly from the base 386, and opposed upper portions 392, 394 extending inwardly from the opposed arms 388, 390. A gap exists between the opposed upper portions 392, 394 to accommodate the downwardly extending shaft 370 of each nesting assembly 346, and the width between the opposed arms 388, 390 is greater than the flange 372 of each nesting assembly 346. Therefore, when the dial conveyor 68 has moved a nesting assembly 346 to one of the indexed locations in the workflow path where the lifting assembly 374 is present, the shaft 370 of the nesting assembly 346 extends through the gap of the associated adaptor collar 378 so that the flange 372 is positioned between the opposed arms 388, 390. The flange 372 is located near the base 386 of the adaptor collar 378 when the pin plate 350 is in an initial, lower position. If one of the verified boxes 22 is going to be placed onto the associated base plate 344, the vertical motion mechanism 376 drives the adaptor collar 378 upwardly. As a result, the base 386 of the adaptor collar 378 contacts the flange 372 and, through the shaft 370, pushes the pin plate 350 toward the base plate 344 until the box locating pins 366 extend through the holes 368 and define the area for containing the box 22.

The nesting assembly 346 includes various components that maintain the pin plate 350 in a raised position even after the dial conveyor 68 moves it to another indexed location. The nesting assembly 346 is able to freely move away from the lifting assembly 374 because of the adaptor collar 378 returns to a home position. More specifically, in the raised position of the pin plate 350 and adaptor collar 378, the flange 372 remains positioned below a plane including the opposed supports 358, 360. The vertical motion mechanism 376 retracts the adaptor collar 378 to a home position in which the upper portions 392, 394 are vertically positioned between the supports 358, 360 and the flange 372. The nesting assembly 346 is then free to move without interference from the lifting assembly 374, with the shaft 370 and flange 372 passing through the adaptor collar 378 because of its open configuration.

After the box 22 has been processed and removed from the dial conveyor 68, the pin plate 350 remains in the raised position. If a blister card 20 is to be deposited on the nesting assembly 346 during the next cycle of the dial conveyor 68, the box locating pins 366 must be retracted from the base plate 344. This is accomplished by moving the adaptor collar 378 to a lowered position. In particular, when the nesting assembly 346 is returned to one of the two indexed locations in the workflow path of the dial conveyor 68 where verified products 12 may be deposited, the shaft 370 and flange 372 are received between the arms 388, 390 of the adaptor collar 378. This is once again the result of the open configuration of the adaptor collar 378. At this point, the vertical motion mechanism 376 moves the adaptor collar 378 downwardly to the lowered position. The opposed upper portions 392, 394 of the adaptor collar 378 engage the flange 372 during this downward movement to pull the pin plate 350 away from the base plate 344 and into its lowered position. The vertical motion mechanism 376 can then return the adaptor collar 378 to its home position without the base 386 contacting the flange 372.

(f) Labeling Station

The first station located in the workflow path of the dial conveyor 68 that processes the products 12 once they are positioned on one of the base plates 344 is the labeling station 76. With reference to FIGS. 32-42, the labeling station 76 includes the label printer 78, the label applicator 80, the label reject device 82, and a flattening device 400. The label printer 78 may comprise any commercial type of label printer 78, and is an ACCRAPLY S8400 Series label printer available from Barry-Wehmiller Companies, Inc. in one specific embodiment. The label printer 78 is mounted on a table 408 and includes a large capacity label feed roll and a large capacity backing take-up roll. The table 408 is supported by a cart 402 that enables the label printer 78 to be moved to various locations without the need for physical lifting. Releasable clamp mechanisms 406 fix the table 408 to the cart 402, and releasable clamp mechanisms 404 fix the cart 402 to the ALV machine 50.

The label printer 78 features a "Plug-and-Play" design so that, in the event of a printer failure or malfunction, the label printer 78 can be easily and quickly replaced with a spare label printer 78. The electrical connections for the label printer 78 with the ALV machine 50 feature releasable connectors (not shown) that promote the rapid replacement. If the label printer 78 fails or malfunctions, the operator releases the clamp mechanisms 404, unplugs the electrical connectors, and wheels the failed label printer 78 away from the ALV machine 50 on the cart 402.

Figure 34:
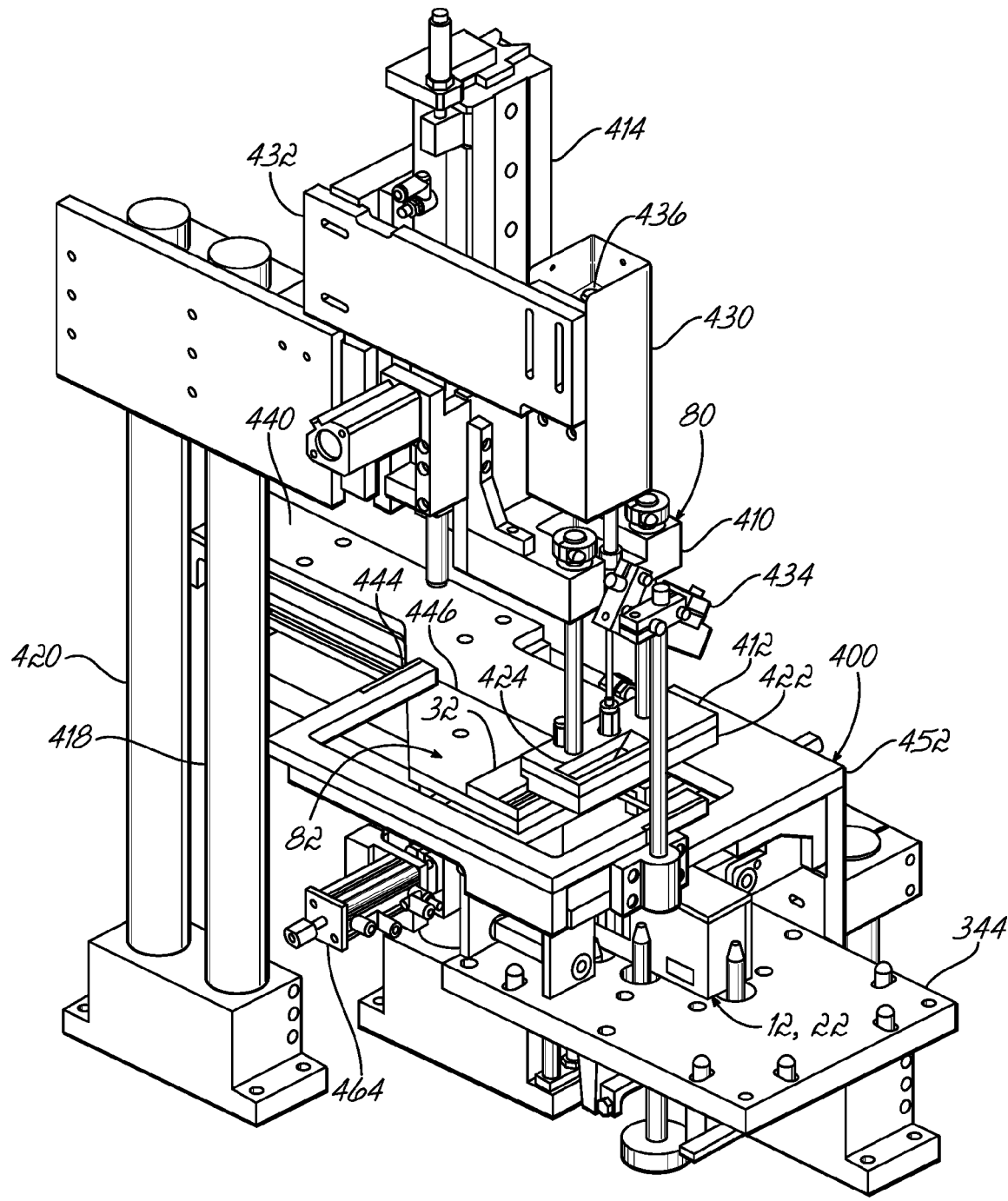
FIG. 34 is a perspective view of the components of a labeling station of the ALV machine.
Figure 35:
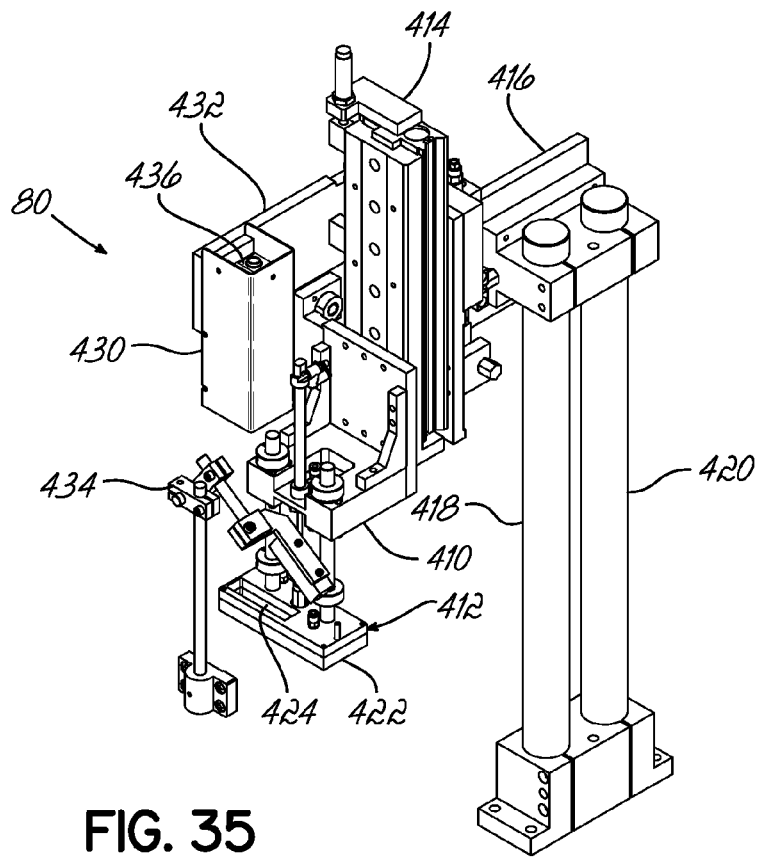
FIGS. 35 and 36 are perspective and side elevation views, respectively, of a label applicator used in the labeling station of FIG. 34.
Figure 36:
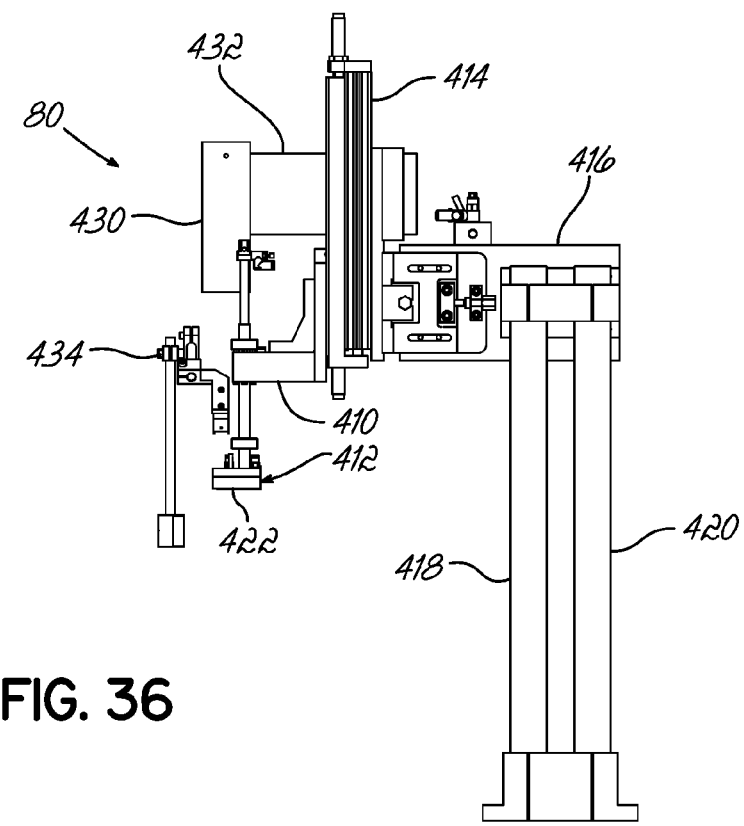
Figure 37:
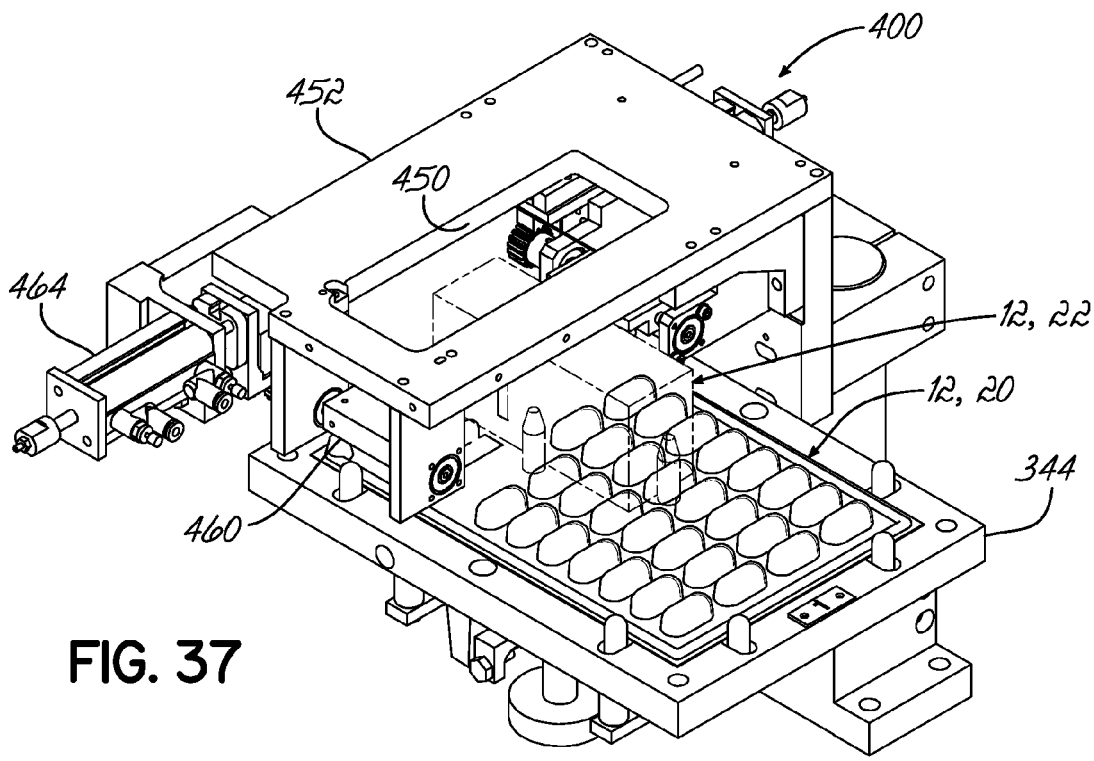
FIGS. 37 and 38 are perspective and top plan views, respectively, of a flattening device used in the labeling station of FIG. 34.
Figure 38:
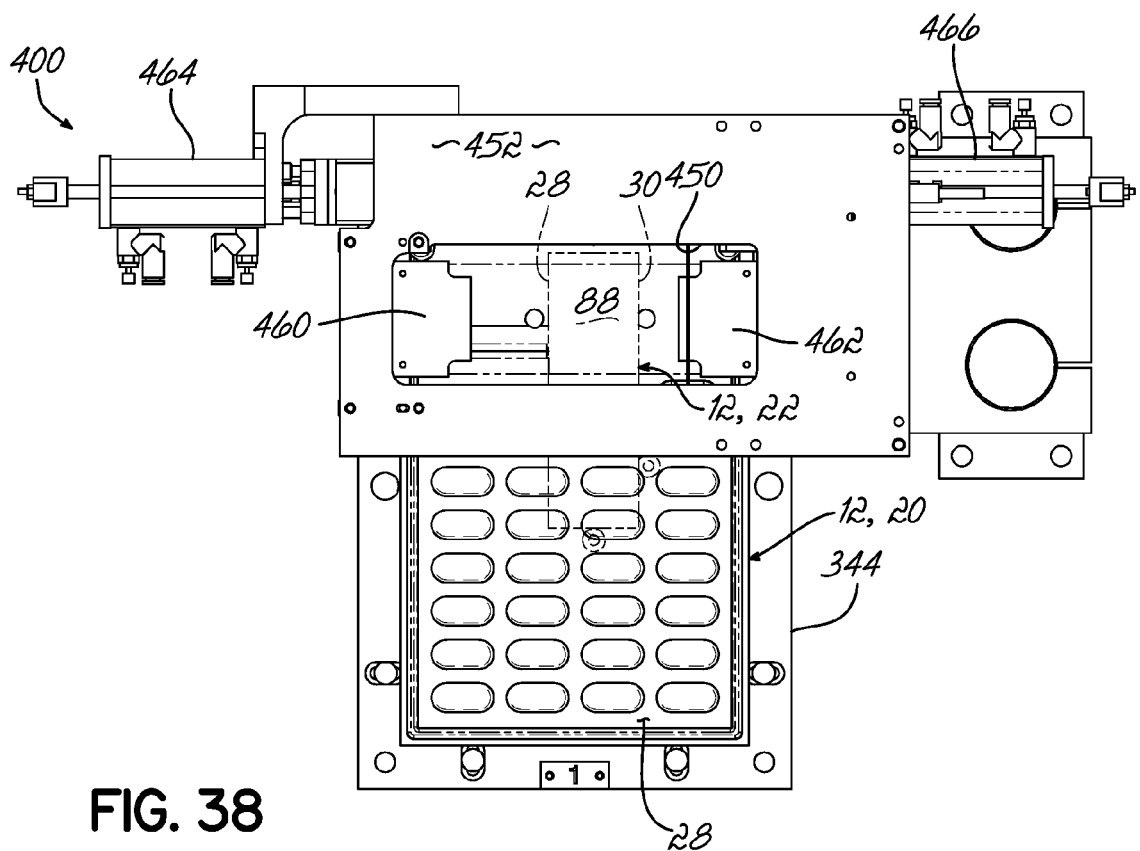
Figure 39:
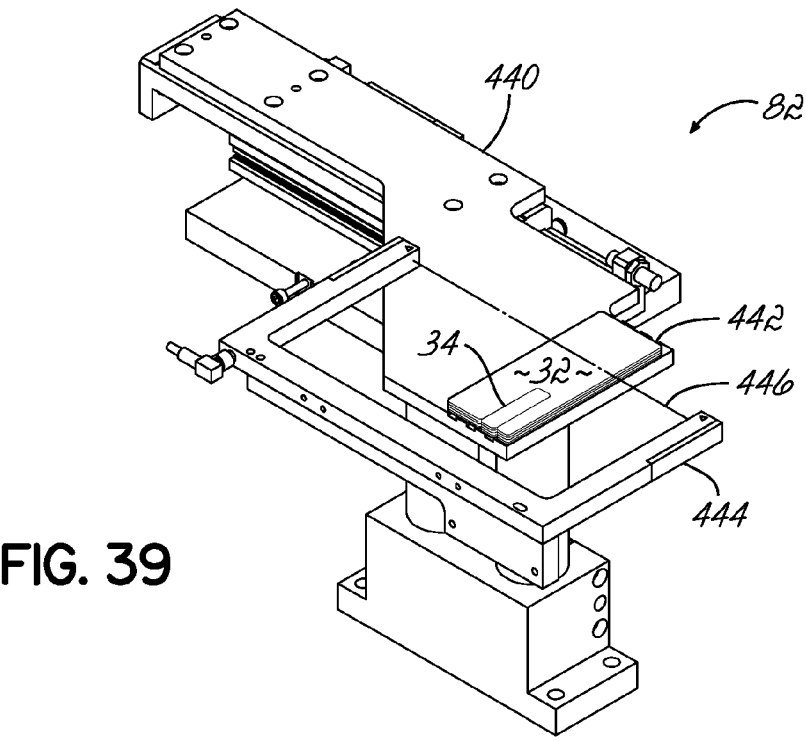
FIGS. 39 and 40 are perspective and top plan views, respectively, of a label rejection device used in the labeling station of FIG. 34.
Figure 40:
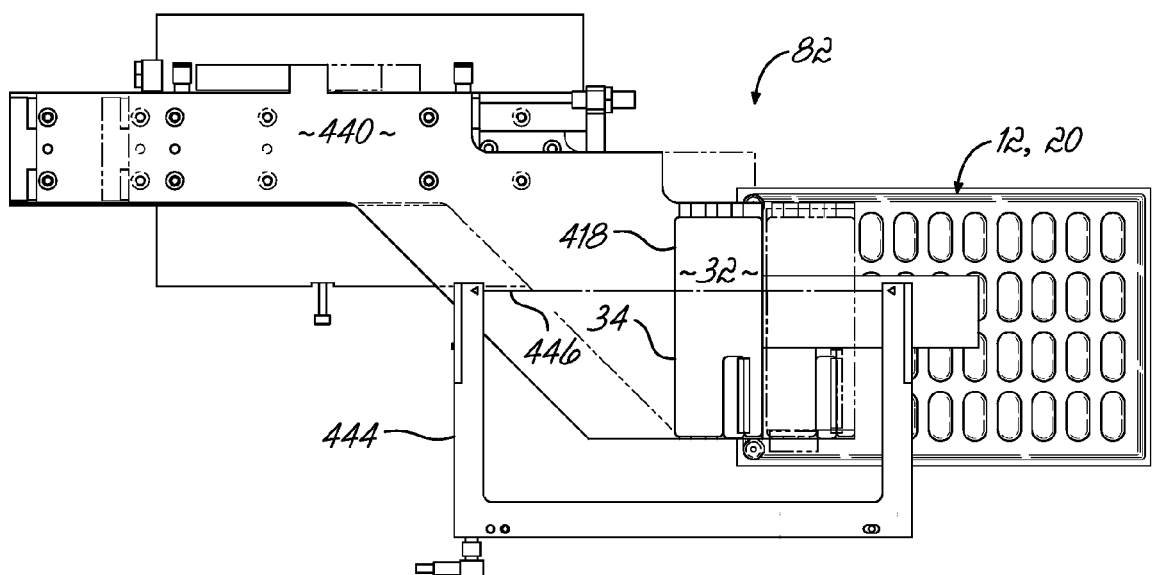

As best shown in FIGS. 34-36, the label applicator 80 of the labeling station 76 includes a tamp block 410, a vacuum tamp head 412 carried by the tamp block 410, an actuator 414 that moves the tamp block 410 vertically, a mounting arm 416 coupled to the actuator 414, and a pair of support shafts 418, 420 that elevate the mounting arm 416 above the dial conveyor 68. The tamp head 412 is configured to temporarily capture each patient label 32 (FIGS. 6 and 7) printed by the label printer 78. Specifically, the tamp head 412 is configured to apply suction to the non-adhesive side of the patient label 32 so that the patient label 32 is temporarily retained against a tamp pad 422 with the adhesive side facing downward toward the product 12. A window 424 extending through the tamp head 412 is aligned with the patient barcode 34 when the patient label 32 is retained against the tamp pad 422. The window 424 thus permits the patient barcode 34 to be viewed and verified prior to being applied on the product 12.

To this end, the label applicator 80 further includes a camera cover 430 and mounting plate 432 coupled to the mounting arm 416. The camera cover 430 is configured to support a camera 436 that captures images of the patient barcode 34 through the window 424. A lighting assembly 434 mounted to the flattening device 400 directs light toward the patient barcode 34 to supplement ambient lighting and facilitate the imaging process. Using machine vision software, the controller of the ALV system 10 analyzes the images captured by the camera 436 of the label applicator 80 to determine if the patient barcode 34 has been successfully printed on the patient label 32. If the product barcode 24 cannot be read or otherwise fails verification, the patient label 32 is flagged for application to the label reject device 82. If the patient barcode 34 is successfully read and verified, the patient label 32 is flagged for application to the product 12.

The label applicator 80 applies the patient labels 32 to the products 12 by causing the actuator 414 to move the tamp block 410 and tamp head 412 downwardly toward the product 12. The label reject device 82 includes a reject plate 440 having a portion initially positioned between the tamp head 412 and product 12 in this path of motion. When a patient label 32 has been flagged as a reject, the reject plate 440 remains in this position so that the tamp head 412 contacts the reject plate 440 rather than the product 12. The actuator 414 pushes the tamp head 412 against the reject plate 440 with sufficient force to establish an adhesive bond between the patient label 32 and the reject plate 440. As a result, the actuator 414 can then move the tamp head 412 back to its initial position with the patient label 32 remaining on the reject plate 440.

Eventually a stack 442 of patient labels 32 that fail verification will accumulate on the reject plate 440. It may be necessary to periodically replace clear the reject plate 440 of these non-verified patient labels 32. A sensor 444 associated with the label reject device 82 determines when the stack 442 has reached a maximum acceptable level (generally designated by line 446). The controller of the ALV system 10 processes signals received from the sensor 444 to notify an operator to remove the stack 442.

When a patient label 32 has been successfully verified and flagged for application to the product 12, an actuator 414 moves the reject plate 440 out of the path of motion of the tamp head 412. The tamp head 412 then moves downwardly through a window 450 provided in a support plate 452 of the flattening device 400 before reaching the product 12. When the product 12 is a box 22, the tamp head 412 presses the patient label 32 against the front surface 88 with sufficient force to establish an adhesive bond but not crush or damage the box 22. The tamp head 412 and patient label 32 have a width greater than the front surface 88, and the box 22 is centered under the tamp head 412. As a result, only a portion of the patient label 32 is adhesively bonded to the box 22 during this label application step. The actuator 414 returns the tamp head 412 to its initial position, leaving the patient label 32 extending across the front surface 88 with portions projecting outwardly from the front surface 88 above the opposed sidewalls 28, 30. These portions are flattened, or "wiped," onto the sidewalls 28, 30 at the label wipe station 90, as will be described below. The camera of the label applicator 80 may be used to verify that the patient label 32 is still not attached to the tamp head 412 prior to moving the box 22 to the label wipe station 90.

When the product 12 at the labeling station 76 is a blister card 20, the flattening device 400 stabilizes the blister card 20 on the base plate 344 when applying the patient label 32. The flattening device 400 includes a pair of fingers 460, 462 rotatably supported above opposite sides of the base plate 344 at the labeling station 76. The fingers 460, 462 are coupled to respective actuators 464, 466, which are shown in the form of air cylinders. The actuators 464, 466 rotate the fingers 460, 462 toward the blister card 20 to push the blister card 20 against the base plate 344. Thus, the blister card 20 is firmly gripped between the fingers 460, 462 and base plate 344 to prevent movement of the blister card 20 during the label application process.

The patient labels 32 are applied to the blister cards 20 in a manner similar to the boxes 22. Namely, the tamp head 412 moves downwardly through the window 450 of the support plate 452 until it presses against the front surface 26 of the blister card 20. Because the entire application area, or landing zone, for the patient label 32 is located on the front surface 26, the patient label 32 is applied entirely flat onto the front surface 26 (there are no projecting portions that must be wiped onto other surfaces). When the tamp head 412 is retracted, the camera of the label applicator 80 may again be used to verify that the patient label 32 is still not attached to the tamp head 412. The actuators 464, 466 rotate the fingers 460, 462 away from the blister card 20 when tamp head 412 is retracted, permitting the dial conveyor 68 to transfer the blister card 20 to the next processing station.

(g) Label Wipe Station

Figure 41:
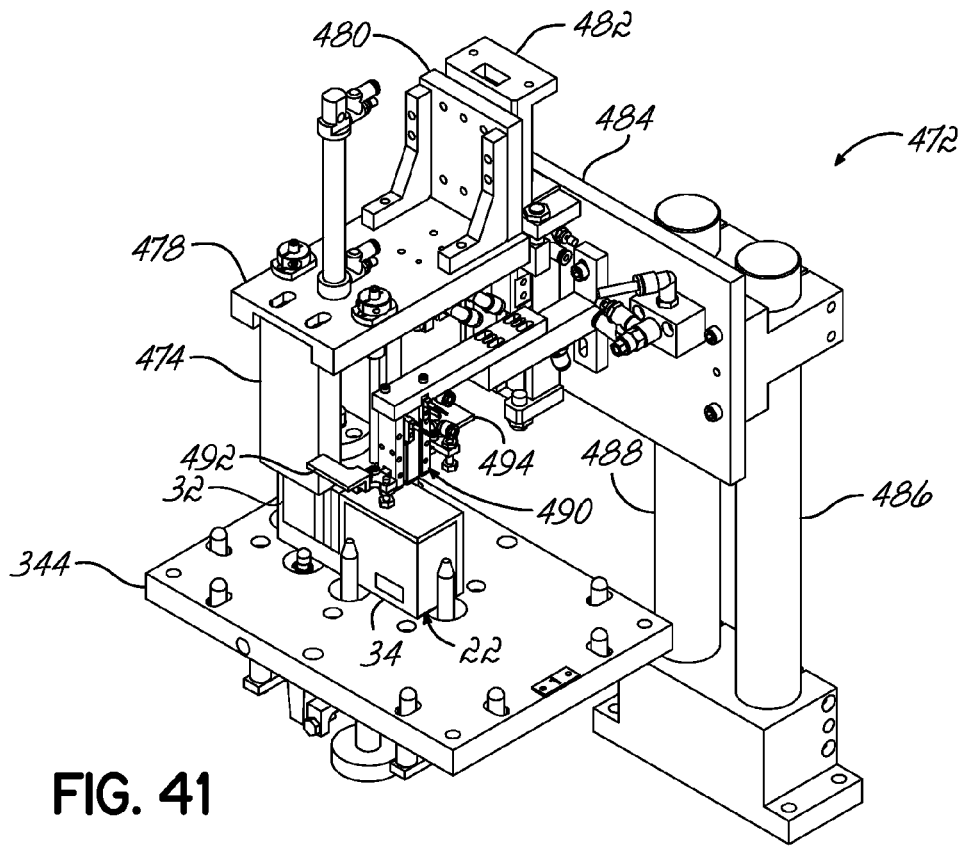
FIGS. 41 and 42 are perspective and side elevation views of a label wiping device associated with the ALV machine.
Figure 42:
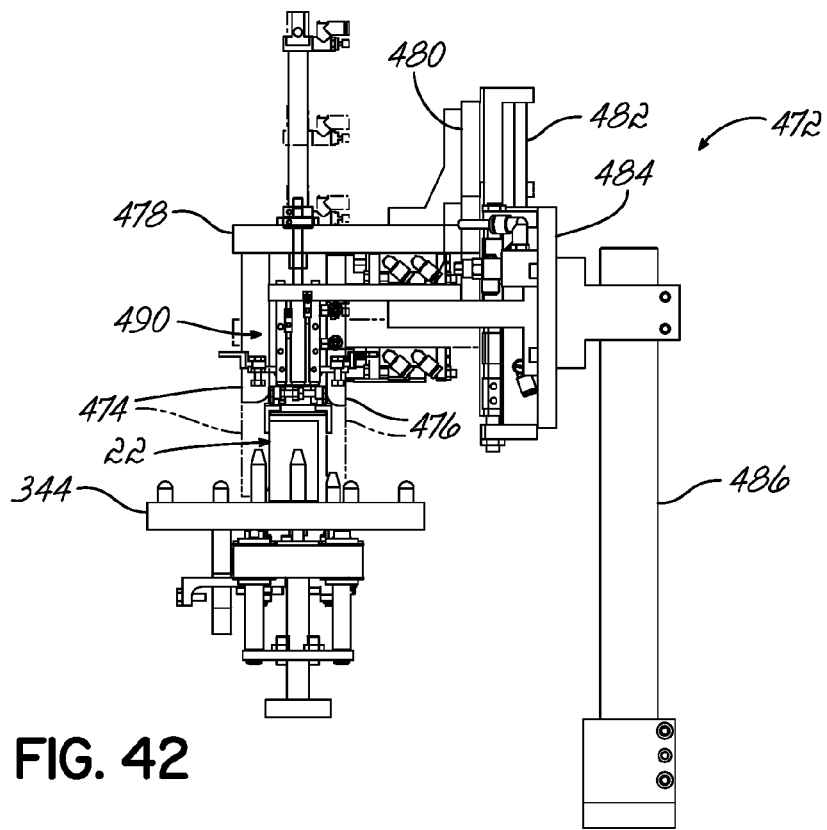

Once a patient label 32 has been applied to a product 12, the dial conveyor 68 is rotated to bring the product 12 to the label wipe station 90. As shown in FIGS. 41 and 42, the label wipe station 90 includes a label wiping device 472 having a pair of wiping fingers 474, 476 suspended above the products 12. The label wiping fingers 474, 476 are generally rectangular elements arranged parallel to each other and spaced apart by a distance approximately equal to the width of one of the boxes 22. Mounting plates 478 and 480 couple the label wiping fingers 474, 476 to a vertical motion mechanism 482, which in turn is coupled to a mounting plate 484 supported by a pair of vertical support shafts 486, 488. The label wiping device 472 also includes a gripping element 490 having gripping fingers 492, 494 that initially project in a horizontal direction.

A sensor (not shown) determines whether a blister card 20 or box 22 is located at the label wipe station 90. If a blister card 20 is present, the label wiping device 472 does not perform any processing steps. As mentioned above, the patient label 32 is initially applied flat onto the front surface 26 of the blister card 20 so that no wiping is necessary. The blister cards 20 are temporarily positioned at the label wipe station 90 without further processing until the dial conveyor 68 is further rotated to move the blister card 20 to the next indexed location in the workflow path.

Boxes 22 brought to the label wipe station 90 have the patient label 32 applied to the front surface 88 with portions of the patient label 32 projecting outwardly over the sidewalls 28, 30. When the sensor detects a box 22, the gripping fingers 492, 494 of the gripping element 490 rotate downwardly to grip the sidewalls 28, 30 of the box 22. With the box 22 stabilized by the gripping element 490, the vertical motion mechanism 482 moves the mounting plates 478, 480 and label wiping fingers 474, 476 downwardly over the box 22. The label wiping fingers 474, 476 closely receive the box 22 therebetween. Thus, during the downward movement, the label wiping fingers 474, 478 contact the projecting portions of the patient label 32 and push them downwardly to create a fold along the side edges of the front surface 88. The projecting portions of the patient label 32 are effectively "wiped"

onto the sidewalls 28, 30 of the box 22. At this point, the gripping element 490 rotates the gripping fingers 492, 494 back to their initial position and the vertical motion mechanism 482 retracts the label wiping fingers 474, 476. The box 22 is now ready to be further processed with the patient label 32 wrapped around the front surface 88 and sidewalls 28, 30.

(h) Vision Inspection Station

Figure 43:
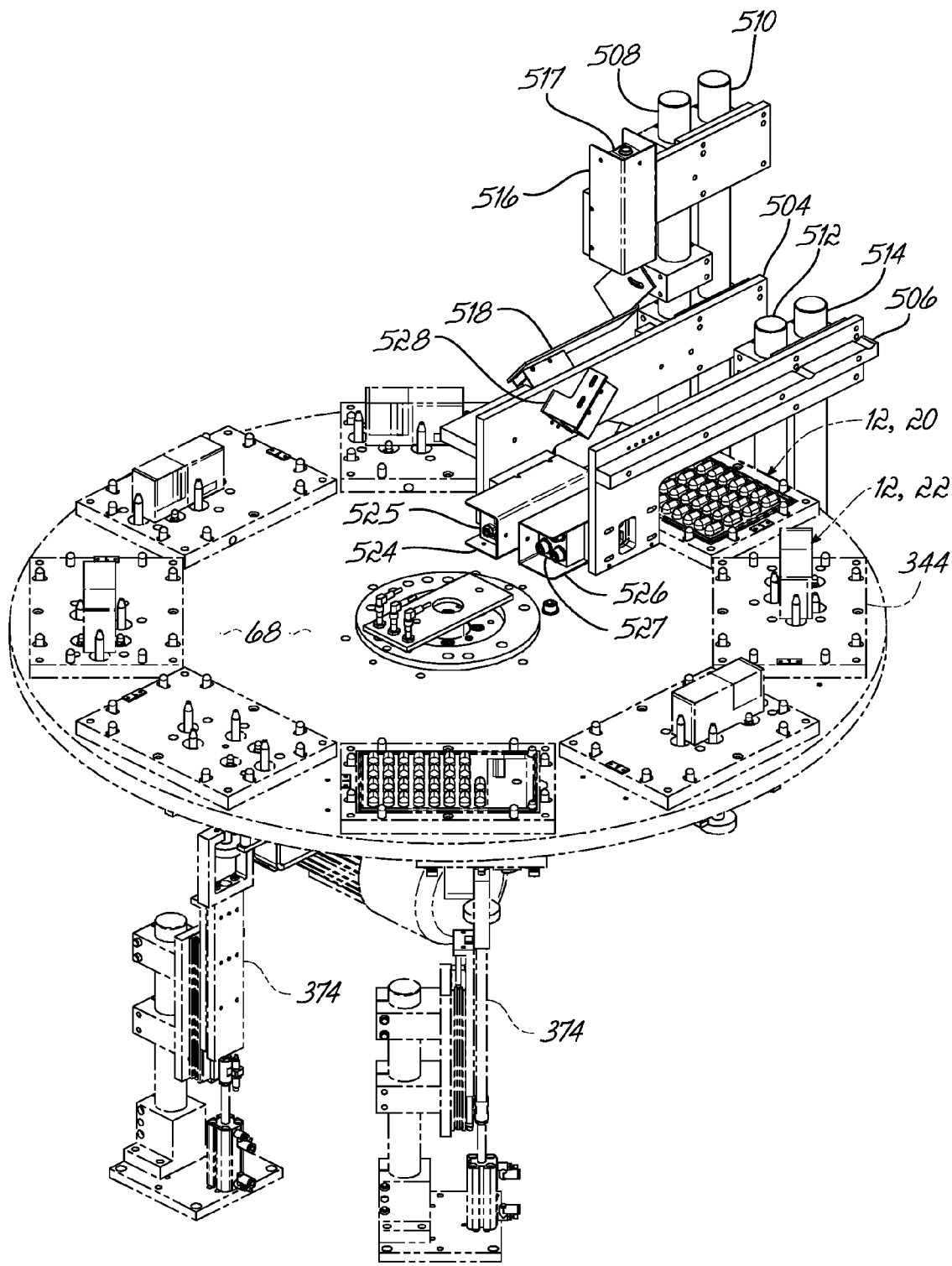
FIG. 43 is a perspective view of a vision inspection station of the ALV machine.

The next indexed location in the workflow path of the dial conveyor 68 is the vision inspection station 92. With reference to FIG. 43, the vision inspection station 92 includes various mounting plates 502, 504, 506 supported above the dial conveyor 68 by vertical support shafts 508, 510, 512, 514. A first camera guard 516 is coupled to the mounting plate 502 and aligned in a generally vertical direction. The first camera guard 516 is configured to support an overhead camera 517 that inspects both the product barcode 24 and the patient barcode 34 on the blister cards 20. Thus, both the product barcode 24 and patient barcode 34 are within the field of view of the overhead camera 517. A lighting assembly 518 may also be suspended above the dial conveyor 68 to assist with this imaging process. As such, the lighting assembly 518 is configured to direct light toward the patient barcode 34 and product barcode 24 on the blister card 20. Those skilled in the art will appreciate that separate cameras (not shown) may be used in alternative embodiments to read the product barcode 24 and patient barcode 34.

The vision inspection station 92 further includes a second camera guard 524 coupled to the mounting plate 504 and a third camera guard 526 coupled to the mounting plate 506. The second and third camera guards 524, 526 are aligned in a generally horizontal direction and suspended only slightly above the dial conveyor 68. The second camera guard 524 is configured to support a camera 525 that reads the patient barcode 24, which, as a result of the label wipe station 90, is positioned on the sidewall 28 of the box 22. The third camera guard 526 is configured to support a camera 527 that reads the product barcode 34 on the sidewall 28 of the box 22. One or more lighting assemblies 528 may be suspended above the dial conveyor 68 proximate the first and second camera guards 524, 526. The lighting assemblies 528 are configured to illuminate the patient barcode 34 and product barcode 24 to facilitate the imaging process.

The controller of the ALV system 10 analyzes the images taken by the cameras 517, 525, 527 of the vision inspection station 92. If the product barcode 24 and patient barcode 34 match, the product 12 is flagged as an accepted item. If the product barcode 24 and patient barcode 34 do not match or cannot be read, the product 12 is flagged as a reject.

(i) Unloading Station

Figure 44:
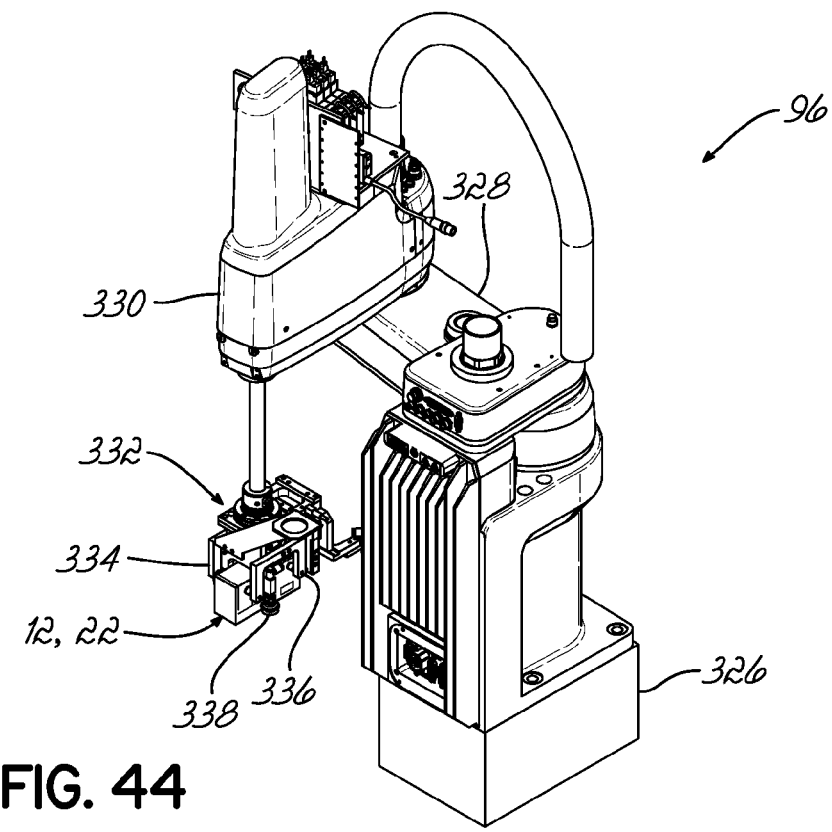
FIG. 44 is a perspective view of a robot representing an unloading station of the ALV machine.

The unloading station 94 of the ALV machine 50 is generally represented by the robot 96, as shown in FIG. 44. Like the robot 66 of the transfer station 64, the robot 96 of the unloading station 94 in the representative embodiment has a SCARA configuration. Indeed, the robot 96 may be the same model (e.g., an Adept Cobra™ robot) as the robot 66 of the transfer station 64 so as to operate in the same manner to move the blister cards 20 and boxes 22 from one location to another. Accordingly, like reference numbers are used in FIG. 44 to refer to like structure from the robot 66, and reference can be made to the description of the robot 66 for a more complete understanding of how these components operate to "pick and place" the blister cards 20 and boxes 22.

Products 12 flagged as rejects at the vision inspection station 92 are picked up by the robot 96 when they reach the unloading station 94 and placed into the second reject bin 98. The first and second reject bins 70, 98 are located in respective drawers or compartments (see FIG. 4) of the ALV machine 50. One or both of the first and second reject bins 70, 98 may be locked by a key or code. Thus, only individuals with the proper authority can access the rejected products 12, which is a safety feature of the ALV system 10.

Products 12 that have been successfully verified and flagged as accepted items at the vision inspection station 92 are picked up by the robot 96 and deposited in one of the containers 54 on the main conveyor 106 of the tote conveyor system 52. As shown in FIG. 45, the robot 96 may deposit rejected and accepted products 12 in an organized manner that makes efficient use of available space.

(j) Tote Conveyor System and Tote Handling System

FIGS. 46-53 illustrate components of the tote conveyor system 52 and tote handling system 56 in further detail. The tote conveyor system 52 includes a tote loading apparatus 540 designed to singulate stacks of the containers 54 onto the main conveyor 106. The tote loading apparatus 540 may be, for example, the Tote Tender™ handling system available from Total Tote, Inc. Such a system de-stacks large volumes of containers 54 at high rates. Thus, in use, an operator places stacks of the containers 54 on a feed conveyor 542 that supplies stacks to the tote loading apparatus 540. The tote loading apparatus 540 then de-stacks the containers 54, one at a time, and supplies them to the main conveyor 106.

The containers 54 include a container barcode (not shown) on one side so that attributes (e.g., a customer facility) can be assigned to the containers 54, and so that labeled and verified products 12 can be checked against the container 54. When loading stacks of the containers 54 onto the feed conveyor 542, an operator ensures that the container barcodes face the same direction. One or more barcode readers 550 positioned along the main conveyor 106 are configured to track the status of the containers 54 after they have been de-stacked by the tote loading apparatus 540. The main conveyor 106 may also include various sensors (not shown) to monitor the location of the containers 54. These sensors enable the main conveyor 106 to stop the containers 54 at the unloading station 94 of the ALV machine 50, where they may be filled with labeled and verified products 12 by the robot 96.

Once the containers 54 are filled, the main conveyor 106 then transports the container 54 to a secondary conveyor 552. If the container 54 has been flagged for auditing, the secondary conveyor 552 transfers the container 54 to the parallel conveyor 108 for delivery to the audit station 100. The audit station 100 includes a hand-held barcode scanner (not shown) and an operator's interface (e.g., a computer monitor). An operator at the audit station 100 scans the product barcodes 24, patient barcodes 34, and the container barcode to check whether the patient labels 32 have been applied to the correct products 12 and whether the products 12 have been placed into the correct container 54.

If the container 54 has not been flagged for auditing, the secondary conveyor 552 transfers the container 54 to the tote handling system 56. The tote handling system 56 includes a loading queue or conveyor 560 that receives the containers 54 from the secondary conveyor 552, in addition to the tote load robot 110 and the tote rack 112. In one specific embodiment, the tote load robot 110 is a six-axis Adept Viper™ robot available from Adept Technologies, Inc. The tote load robot 110 is configured to pick the containers 54 up from the loading conveyor 560 and place them either onto the tote return conveyor 114 for delivery to the audit station 100 or onto the tote rack 112 for temporary storage. The tote rack 112 includes shelves 562 divided into separate lanes 564 for storing the containers 54. The lanes 564 are inclined from the front of the tote rack 112, which is accessible by operators, to the rear of the tote rack 112, which is accessible by the tote load robot 110. Because the lanes 564 each comprise a plurality of rollers 566, containers 54 deposited by the tote load robot 110 are able to travel along the lanes 564 to the front of the tote rack 112. Stops 568 positioned at the front of the tote rack 112 prevent the containers 54 from falling off the shelves 562.

The components of the ALV system 10 described in detail above are merely representative in nature. Those skilled in the art will appreciate that other components may be used to process products 12 in a manner similar to the ALV system 10.

In summary, the ALV system 10 opportunistically relies on the two common form factors, namely blister cards 20 or boxes 22 of solid dosages, to improve efficiency and to automate a labeling and verification process. The ALV system 10 processes and optimizes pharmacy verification or post-adjudicated orders/pick requests, verifies that the correct patient label 32 is placed on the correct product 12, and verifies that the correct product 12 is placed into the correct container 54, without any damage either to the product 12 or to the patient label 32. The labeled and verified products 12 may include any combination of blister cards 20 and boxes 22, along with other potential form factors. The ALV system 10 reduces medication errors associated with manual distribution, lowers costs associated with pharmaceutical distribution, permits reductions in personnel, and improves inventory control.

While the invention has been illustrated by a description of various embodiments and while these embodiments have been described in considerable detail, it is not the intention of the applicants to restrict or in any way limit the scope of the appended claims to such detail. Additional advantages and modifications, along with component substitutions, will readily appear to those skilled in the art. For example, wherever a "camera" is discussed in this specification, those skilled in the art will appreciate that other types of barcode readers may be used by the ALV system 10. Thus, the invention in its broader aspects is therefore not limited to the specific details, representative apparatus and method, and illustrative example shown and described. Accordingly, departures may be made from such details without departing from the spirit or scope of applicants' general inventive concept.

What is claimed is:

1. An apparatus for filling a customer order with a plurality of products each containing a pharmaceutical and each marked with a product barcode, the apparatus comprising:
    a dial conveyor defining a circular workflow path for processing the products;
    a label application station arranged about the circular workflow path of the dial conveyor and configured to print and apply a patient label onto each of the products;
    a vision inspection station arranged about the circular workflow path of the dial conveyor, the vision inspection station configured to independently verify that the product barcode on each of the products matches a patient barcode on the patient label after application to the product; and
    an unloading station configured to transfer labeled and verified products away from the conveyor.

2. The apparatus of claim 1 further comprising:
    a product loading station configured to receive batches of the products, the product loading station further configured to singulate the products in each of the batches.

3. The apparatus of claim 2 wherein the product loading station includes a barcode reader configured to read the product barcode on each of the products.

4. The apparatus of claim 2 wherein the product loading station is configured to process products shaped with a card form factor, and the product loading station comprises:
    a product induction magazine defining a feed chute configured to receive a stack of the products shaped with the card form factor;
    a landing plate defining a bottom of the feed chute and configured to support the stack of the products shaped with the card form factor; and
    a gripping device movable relative to the landing plate, the gripping device configured to cooperate with the product induction magazine to successively singulate each of the products from the stack.

5. The apparatus of claim 2 wherein the product loading station is configured to process products shaped with a box form factor, and the product loading station comprises:
    a load conveyor configured to move products shaped with the box form factor that have placed on the load conveyor;
    an infeed conveyor arranged generally perpendicular to the load conveyor; and
    a transfer arm configured to move the products from the load conveyor to the infeed conveyor.

6. The apparatus of claim 5 wherein the box loading station further comprises:
    a box rotation mechanism including a bracket configured to support at least a portion of one of the products moved by the infeed conveyor, a rotary actuator coupled to the bracket, a frame supporting the rotary actuator, and a linear actuator configured to move the frame vertically.

7. The apparatus of claim 2 further comprising:
    a transfer station configured to transfer the products from the product loading station to the conveyor.

8. The apparatus of claim 7 further comprising:
    a control system operatively connected with the conveyor, the product loading station, the transfer station, the label application station, the vision inspection station, and the unloading station, the control system configured to control the filling of the customer order by the stations.

9. The apparatus of claim 7 wherein the transfer station comprises:
    at least one robot configured to pick the products up from the product loading station and place the products on the conveyor.

10. The apparatus of claim 9 further comprising:
    a reject bin positioned adjacent the conveyor, the at least one robot configured to pick the products up from the product loading station and place the products in the reject bin.

11. The apparatus of claim 1 further comprising:
    a card loading station configured to receive and singulate batches of the products shaped with a card form factor; and
    a box loading station configured to receive and singulate batches of the products shaped with a box form factor.

12. The apparatus of claim 1 wherein the label application station is configured to independently verify the patient barcode on the patient label before the patient label is applied to one of the products.

13. The apparatus of claim 1 wherein the label application station comprises:
    a label printer configured to print the patient labels;
    an applicator configured to temporarily capture the patient labels from the label printer and move the patient labels along a path of motion toward the product being processed by the label application station; and a reject plate selectively movable between a first position in the path of motion of the applicator and a second position out of the path of motion, the applicator configured to apply each of the patient labels to one of the products or to the reject plate.

14. The apparatus of claim 13 wherein the applicator includes a tamp head having a window configured to be aligned with the patient barcode on the patient label, and wherein the label application station further comprises:
a barcode reader configured to read the patient barcode through the window before the patient label is applied to one of the products being processed or the reject plate.

15. The apparatus of claim 13 wherein the products are shaped with at least two different form factors, and the applicator is configured to apply each of the patient labels to the products of the different form factors.

16. The apparatus of claim 1 further comprising:
a label wipe station including a sensor configured to detect whether the product being processed is shaped with a box form factor and a pair of wiping fingers suspended above the conveyor, the wiping fingers being generally parallel to each other and movable toward the conveyor to further apply portions of each patient label on products shaped with the box form factor.

17. The apparatus of claim 1 wherein the products are shaped with a card form factor or a box form factor, and the vision inspection station comprises:
a first barcode reader configured to read the product barcode and patient barcode on the products shaped with the card form factor;
a second barcode reader configured to read the product barcode on the products shaped with the box form factor; and
a third barcode reader configured to read the patient barcode on the products shaped with the box form factor.

18. The apparatus of claim 1 further comprising:
a tote conveyor system configured to supply containers into which labeled and verified products are placed.

19. The apparatus of claim 18 further comprising:
a tote handling system configured to manage the containers after the containers have been filled with labeled and verified products, the tote handling system including a loading conveyor configured to receive the containers from the tote conveyor system, a tote rack having shelves divided into lanes for storing the containers, and a robot configured to pick each container up from the loading conveyor and place the container in one of the lanes of the tote rack.

20. The apparatus of claim 1 wherein the unloading station further comprises:
at least one robot configured to remove the products from the conveyor after the products have been labeled and verified.

21. A method of filling a customer order with a plurality of products each containing a pharmaceutical, the products being loaded into a machine for processing, the method comprising:
automatically verifying a product barcode on each of the products with the machine;
transferring the products with a verified product barcode onto a dial conveyor that defines a circular workflow path for processing the products in the machine;
printing a patient label for each of the products processed in the machine;
applying the patient labels to the products processed in the machine; and
after the patient label is applied to each of the products, independently verifying that the product barcode matches a patient barcode on the patient label.

22. The method of claim 21 further comprising:
singulating batches of the products loaded into the machine so that the products can be individually processed by the machine.

23. The method of claim 22 wherein singulating batches of the products further comprises:
singulating batches of products shaped with a card form factor in a first product loading station; and
singulating batches of products shaped with a box form factor in a second product loading station.

24. The method of claim 21 wherein automatically verifying a product barcode on each of the products with the machine further comprises:
reading the product barcode on each of the products after each product has been loaded into a product loading station of the machine; and
comparing the product barcode to tracking data to verify that the product belongs in the customer order being filled.

25. The method of claim 24 wherein the products with the verified product barcode are transferred from the product loading station onto the dial conveyor.

26. The method of claim 24 further comprising:
transferring the products with a product barcode that fails verification from the product loading station into a reject bin positioned adjacent the dial conveyor.

27. The method of claim 24 wherein transferring the products with the verified product barcode further comprises:
picking the products up from the product loading station with a robot; and
placing the products onto a designated location on the dial conveyor.

28. The method of claim 21 wherein the patient labels are printed by a label printer, and applying the patient labels further comprises:
temporarily capturing each patient label with an applicator after the patient label has been printed, the applicator being suspended above the product being processed; and
moving the applicator and the patient label captured by the applicator along a path of motion toward the product being processed.

29. The method of claim 28 further comprising:
reading the patient barcode while the patient label is temporarily captured by the applicator to verify the patient label.

30. The method of claim 29 further comprising:
applying patient labels with a patient barcode that fails verification onto a reject plate located in the path of motion of the applicator; and
moving the reject plate out of the path of motion when the patient label captured by the applicator has a verified patient barcode so that the patient label can be applied to the product being processed.

31. The method of claim 28 wherein applying the patient labels further comprises:
retaining the patient labels on a tamp head with each patient label arranged so that the patient barcode is generally aligned with a window in the tamp head; and
reading the patient barcode through the window of the tamp head.

32. The method of claim 28 wherein applying the patient labels to at least some of the products further comprises:
applying the patient labels with the applicator to at least one of the products shaped with a card form factor; and applying the patient labels with the applicator to at least one of the products shaped with a box form factor.

33. The method of claim 31 wherein each patient label applied to the products shaped with the box form factor is applied to a front surface of the box with portions of the patient label projecting outwardly from the front surface above opposed sidewalls of the box, and the method further comprises:
wiping the projecting portions of the patient label onto the opposed sidewalls of the box with a pair of wiping fingers.

34. The method of claim 21 wherein independently verifying the product barcode and patient barcode further comprises:
reading the product barcode and the patient barcode on each product with one or more barcode readers;
comparing the product barcode read from each product to tracking data to verify that the product belongs in the customer order being filled; and
comparing the patient barcode read from each product to tracking data to verify that the correct patient label has been applied to the correct product.

35. The method of claim 34 wherein reading the product barcode and patient barcode on each product with one or more barcode readers further comprises:
reading the product barcode and the patient barcode on each product shaped with a card form factor with a first barcode reader;
reading the product barcode on each product shaped with a box form factor with a second barcode reader; and
reading the patient barcode on each product shaped with the box form factor with a third barcode reader.

36. The method of claim 21 further comprising:
transferring products with the product barcode and the patient barcode that have been independently verified after the patient label is applied from the machine into a container on a conveyor system.

37. The method of claim 36 further comprising:
transferring products with the patient barcode or the product barcode that fail verification, after the patient label is applied, into a reject bin located in the machine.

38. The method of claim 36 wherein transferring products with the product barcode and the patient barcode that have been independently verified further comprises:
picking the products up from a surface of the machine with a robot; and
placing the products into the container with a desired orientation.

39. An apparatus for filling a customer order with a plurality of products each containing a pharmaceutical, the apparatus comprising:
a product loading station configured to receive batches of the products, the product loading station further configured to singulate the products for subsequent movement along a workflow path;
a first verification station configured to receive the products singulated by the product loading station, the first verification station including a barcode reader configured to read a product barcode on each of the products and a transfer arm configured to remove the products from the workflow path;
a label printing station configured to receive the products not removed from the workflow path by the transfer arm, the label printing station including a label printer configured to print patient labels and an applicator configured to apply each patient label on one of the products; and
a second verification station configured to receive the products from the label printing station, the second verification station including a barcode reader configured to read the product barcode on each of the products and a patient barcode on each of the patient labels, the second verification station further including a transfer arm configured to remove the products from the workflow path.

40. The apparatus of claim 39 wherein the labeling station is configured to independently verify the patient barcode printed on the patient label before the patient label is applied to one of the products.

41. The apparatus of claim 39 wherein the product loading station, the first verification station, the labeling station, and the second verification station are configured to process products shaped with at least two different form factors.

42. The apparatus of claim 39 further comprising:
a dial conveyor configured to serially transfer the products to the label printing station and the second verification station along the workflow path.

43. An apparatus for processing products shaped with at least two different form factors and each containing a pharmaceutical to fulfill a customer order, the apparatus comprising:
a machine defining a workflow path for the products shaped with the at least two different form factors; and
a plurality of automated stations arranged relative to the workflow path of the machine, the automated stations configured to automatically apply a label to each of the products shaped with the at least two different form factors and to automatically verify that each of the products belongs to the customer order.

44. The method of claim 43 wherein the machine includes a dial conveyor, and the workflow path of the machine is circular as defined by the dial conveyor.

45. A method of filling a customer order with a plurality of products each containing a pharmaceutical, the method comprising:
generating pick requests for the products with a pharmacy host server;
transmitting the pick requests to an automated dispensing system;
managing the pick requests with the automated dispensing system to generate pick batches for containers to be filled with products, the pick batches representing products to be loaded into the automated dispensing system; and
operating the automated dispensing system to automatically process the products and place the products into the containers.

46. The method of claim 45 wherein managing the pick requests with the automated dispensing system further comprises:
applying sortation rules to the pick requests to generate the pick batches; and
controlling the operation of the automated dispensing system based upon the pick batches.

47. The method of claim 46 wherein controlling the operation of the automated dispensing system further comprises:
determining whether the pick batches substantially fill a shipping tote for delivery to a customer facility.

48. The method of claim 46 wherein controlling the automated dispensing system further comprises:
switching the automated dispensing system between a mode of operation wherein the products are placed into shipping totes for delivery to a customer facility, a mode of operation wherein the products are placed into processing totes that represent partial orders for the customer facility, and a mode of operation wherein the products are placed into containers representing a storage area in a pharmacy.

49. The method of claim 45 wherein operating the automated dispensing system further comprises:
   automatically verifying that the products loaded into the automated dispensing system belong in the pick batch being processed;
   automatically printing and applying a patient label to the products; and
   automatically verifying that the patient label has been applied to the correct product.

50. The method of claim 49 wherein automatically verifying that the patient label has been applied to the correct product further comprises:
   independently verifying that each product belongs in the pick batch being processed.

51. The method of claim 45 wherein operating the automated dispensing system further comprises:
   operating the automated dispensing system in a mode wherein the products are placed into shipping totes for delivery to a customer facility.

52. The method of claim 45 further comprising:
   operating the automated dispensing system in a mode wherein the products are placed into processing totes that represent partial orders for a customer facility; and
   combining the products from at least two of the processing totes filled by the automated dispensing system into a common shipping tote for delivery to a customer facility.

53. The method of claim 52 wherein combining the products from at least two of the processing totes filled by the automated dispensing system into a common shipping tote further comprises:
   a) reading a barcode on one of the processing totes with a barcode reader;
   b) reading a barcode on the shipping tote;
   c) placing the products from the one processing tote into the shipping tote; and
   d) repeating steps a-c for each additional processing tote containing additional products to be placed into the shipping tote.

54. The method of claim 53 wherein barcodes on the products are not individually scanned when combining the products of at least two of the processing totes.

* * * * *

UNITED STATES PATENT AND TRADEMARK OFFICE
CERTIFICATE OF CORRECTION

| | | |
|---|---|---|
| PATENT NO. | : 8,215,540 B2 | |
| APPLICATION NO. | : 12/235173 | |
| DATED | : July 10, 2012 | |
| INVENTOR(S) | : Michael J. Szesko et al. | |

It is certified that error appears in the above-identified patent and that said Letters Patent is hereby corrected as shown below:

At column 5, line 28, change "packaged" to --packages--.

At column 7, line 48, change "conveyors" to --conveyor-- and at line number 64, after "used" insert --to--.

At column 9, line 36, after "it" insert --is-- and at line number 61, after "in" delete "the".

At column 14, line 67, after "270" delete "is".

At column 19, line 36, after "periodically" delete "replace".

At column 24, claim 5, line 19, after "have" insert --been--.

Signed and Sealed this
Eighteenth Day of September, 2012

David J. Kappos
*Director of the United States Patent and Trademark Office*